US008524656B2

(12) United States Patent
Galipeau et al.

(10) Patent No.: US 8,524,656 B2
(45) Date of Patent: Sep. 3, 2013

(54) GM-CSF AND TRUNCATED CCL2 CONJUGATES AND METHODS AND USES THEREOF

(76) Inventors: Jacques Galipeau, Atlanta, GA (US); Moutih Rafei, Pierrefonds (CA)

(*) Notice: Subject to any disclaimer, the term of this patent is extended or adjusted under 35 U.S.C. 154(b) by 0 days.

(21) Appl. No.: 13/003,027

(22) PCT Filed: Jul. 8, 2009

(86) PCT No.: PCT/CA2009/000948
§ 371 (c)(1),
(2), (4) Date: Jan. 7, 2011

(87) PCT Pub. No.: WO2010/003240
PCT Pub. Date: Jan. 14, 2010

(65) Prior Publication Data
US 2011/0124552 A1   May 26, 2011

Related U.S. Application Data

(60) Provisional application No. 61/079,012, filed on Jul. 8, 2008, provisional application No. 61/143,536, filed on Jan. 9, 2009.

(51) Int. Cl.
*A61K 38/00* (2006.01)
*C12N 15/62* (2006.01)
*C07K 14/00* (2006.01)

(52) U.S. Cl.
USPC .......... 514/1.1; 514/16.6; 514/17.9; 514/21.2; 530/350; 435/69.7

(58) Field of Classification Search
None
See application file for complete search history.

(56) References Cited

U.S. PATENT DOCUMENTS

| | | | |
|---|---|---|---|
| 5,532,144 | A | 7/1996 | Yoshimura et al. |
| 5,714,578 | A | 2/1998 | Yoshimura et al. |
| 6,090,795 | A | 7/2000 | Yoshimura et al. |
| 6,869,924 | B1 | 3/2005 | Yoshimura et al. |
| 7,157,418 | B1 | 1/2007 | McDonald et al. |
| 7,166,702 | B1 | 1/2007 | McDonald et al. |
| 7,192,736 | B2 | 3/2007 | McDonald et al. |
| 7,319,091 | B2 | 1/2008 | Yoshimura et al. |
| 2002/0168370 | A1 | 11/2002 | McDonald et al. |
| 2003/0215421 | A1 | 11/2003 | McDonald et al. |
| 2004/0157253 | A1 | 8/2004 | Xu et al. |
| 2004/0185450 | A1 | 9/2004 | Heavner et al. |
| 2005/0053579 | A1* | 3/2005 | Galipeau et al. ............ 424/85.1 |
| 2006/0198820 | A1 | 9/2006 | McDonald et al. |
| 2007/0031833 | A1 | 2/2007 | Kotani et al. |
| 2007/0037794 | A1 | 2/2007 | Ungashe et al. |
| 2007/0197590 | A1 | 8/2007 | DeMong et al. |
| 2007/0219245 | A1 | 9/2007 | Hou et al. |
| 2007/0270329 | A1 | 11/2007 | Yoshimura et al. |

FOREIGN PATENT DOCUMENTS

| | | |
|---|---|---|
| WO | 9008777 | 8/1990 |
| WO | 9008778 | 8/1990 |
| WO | 0004926 | 2/2000 |
| WO | 03035105 | 5/2003 |
| WO | 2005060665 | 7/2005 |
| WO | 2006031931 | 3/2006 |
| WO | 2006083798 | 8/2006 |
| WO | 2007027661 | 3/2007 |
| WO | 2007130712 | 11/2007 |
| WO | 2008036966 | 3/2008 |
| WO | 2010003240 | 1/2010 |

OTHER PUBLICATIONS

Ngo et al., 1994, The Protein Folding Problem and Tertiary Structure Prediction, Merz et al., eds., Birkhauser, Boston, pp. 491-495.*
Wells, 1990, Biochemistry 29:8509-8517.*
Adhikari et al. ("Cell Mediated Immunity" at www.antimicrobe.org/history/Cell%20mediated%20immunity-Mietzner%203-2-08.pdf; accessed Feb. 19, 2013).*
Gura (Science, v278, 1997, pp. 1041-1042).*
Freshney (Culture of Animal Cells, A Manual of Basic Technique, Alan R. Liss, Inc., 1983, New York, p. 4).*
Dermer (Bio/Technology, 1994, 12:320).*
Fischer et al., 2011, J. Cranio-Maxillo-Facial Surgery 39:54-64.*
McQuibban, G.A., et al., "Inflammation Dampened by Gelatinase A Cleavage of Monocyte Chemoattractant Protein-3", Science Aug. 18, 2000, vol. 289, pp. 1202-1206.
McQuibban, G.A., et al., "Matrix metalloproteinase processing of monocyte chemoattractant proteins generates CC chemokine receptor antagonists with anti-inflammatory properties in vivo", Blood, Aug. 12, 2002, vol. 100, No. 4, pp. 1160-1167.
Robinson, E.A., et al. "Complete amino acid sequence of a human monocyte chemoattractant, a putative mediator of cellular immune reactions", Proc Natl Acad Sci U S A, Mar. 1989, vol. 86, pp. 1850-1854.
Rafei, M. and Galipeau, J., "A CCL2-Based Fusokine as a Novel Biopharmaceutical for the Treatment of CCR2-Driven Autoimmune Diseases", Critical Reviews in Immunology, 2010, vol. 30, pp. 447-459.
Rafei, M., et al., "Selective inhibition of CCR2 expressing lymphomyeloid cells in experimental autoimmune encephalomyelitis by a GM-CSF-MCP1 fusokine", The Journal of Immunology, Mar. 1, 2009, vol. 182, No. 5, pp. 2620-2627.
Mirzadegan, T., et al., "Identification of the binding site for a novel class of CCR2b chemokine receptor antagonists", The Journal of Biological Chemistry, Apr. 17, 2000, vol. 275, No. 33, pp. 25562-25571.
Proost, P., et al., "Posttranslational modifications affect the activity of the human monocyte chemotactic proteins MCP-1 and MCP-2: identification of MCP-2(6-76) as a natural chemokine inhibitor", The Journal of Immunology, Apr. 15, 1998, vol. 160, No. 8, pp. 4034-4041.
Rafei, M. et al., "A GMCSF and IL-15 fusokine leads to paradoxical immunosuppression in vivo via asymmetrical JAK/STAT signaling through the IL-15 receptor complex", Blood, Nov. 2, 2006, vol. 109, No. 5, pp. 2234-2242.
Rodriguez-Frade, J.M., et al., "The chemokine monocyte chemoattractant protein-1 induces functional responses through dimerization of its receptor CCR2", Proceedings of the National Academy of Science USA, Mar. 30, 1999, vol. 96, No. 7, pp. 3628-3633.
Rafei, M. et al., "An Engineered GM-CSF-CCL2 Fusokine Is a Potent Inhibitor of CCR2-Driven Inflammation As Demonstrated in a Murine Model of Inflammatory Arthristis", The Journal of Immunology, 2009, vol. 183, pp. 1759-1766.

* cited by examiner

*Primary Examiner* — Elizabeth C Kemmerer

(57) ABSTRACT

A conjugate protein comprising a GM-CSF or a fragment thereof and a truncated CCL2 is described. The conjugate protein has unexpected immune suppressive, anti-obesity and tumoricidal properties and is useful in a variety of therapeutic applications.

6 Claims, 25 Drawing Sheets

GM-CSF AND TRUNCATED CCL2 CONJUGATES AND METHODS AND USES THEREOF

CROSS REFERENCE TO RELATED APPLICATIONS

This is a national stage application of PCT/CA2009/000948 filed on Jul. 8, 2009 which claims priority from U.S. provisional application 61/079,012 filed on Jul. 8, 2008, and U.S. provisional application 61/143,536 filed on Jan. 9, 2009, all of which are incorporated herein by reference in their entirety.

INCORPORATION OF SEQUENCE LISTING

A computer readable form of the Sequence Listing "17498NP SequenceListing.txt" (6,544 bytes), submitted via EFS-WEB and created on Jan. 6, 2011, is herein incorporated by reference.

FIELD OF THE DISCLOSURE

The disclosure relates to conjugates useful in the modulation of the immune response, in treating cancer and treating CCR2-mediated conditions or diseases, such as obesity. In particular, the disclosure relates to the conjugate of GM-CSF with truncated CCL-2 and methods and uses thereof.

BACKGROUND OF THE DISCLOSURE

Immune stimulatory cytokines can be exploited to treat human ailments including cancer. Amongst cytokines identified for such use, Granulocyte-Macrophage-Colony Stimulating Factor (GM-CSF) has been under much scrutiny since it acts directly on the adaptive immune system by enhancing antigen presentation as well as costimulation (Dranoff et al. 1993). Furthermore, second generation strategies linking innate and adaptive immunity using GM-CSF delivered as a fusion cytokine (fusokine) with other immune stimulatory proteins such as Interleukin-2 (IL-2) and IL-3 have been developed (Stagg et al 2004). GM-CSF was first described as a growth factor for granulocyte and macrophage progenitor cells. However, GM-CSF is also an important mediator for inflammatory reactions produced by T lymphocytes, macrophages and mast cells present at sites of inflammation (Demetri and Griffin, 1991). GM-CSF is a strong chemoattractant for neutrophils. It enhances microbicidal activity, phagocytotic activity and cytotoxicity of neutrophils and macrophages. An important feature of GM-CSF is that it greatly enhances the state of antigen presentation on dendritic cells, known to be crucial mediators of acquired immunity. The DNA and protein sequences of GM-CSF have been protected under PCT application WO8600639 and the derived patents.

CCL2, a chemokine of the CC family, was first characterized as a monocyte-chemoattracting protein. Its expression is promoted after exposure to inflammatory stimuli such as IL-1, TNF-alpha or IL-4. CCR2, the receptor for CCL2, is a $G_i$-coupled receptor highly expressed on monocytes, dendritic cells, T and B cells. Subsequent studies showed that CCR2 is also expressed on activated and memory T cells, including both $T_H1$ and $T_H2$ cells. Both CCL2- and CCR2-deficient mice show defects in monocyte recruitment. Animals that lack CCL2 show diminished T cell responses. In contrast, CCR2 deficient mice have markedly reduced T cell IFN-gamma responses, defects in clearance of intracellular pathogens and increased resistance to the $T_H1$-mediated disease, such as experimental autoimmune encephalomyelitis (EAE).

The success of inflammatory reactions rely on the coordination and control of immune cell trafficking, which is mediated by chemokines, a large group of chemotactic molecules divided in four groups (Luther and Cyster, 2001). These small polypeptides usually bind to their cognate G protein-coupled receptors (GPCRs) mediating various physiological processes including inflammation, allograft rejection, autoimmunity, viral infections and lymphopoeisis (Campbell and Butcher, 2000; Lee et al. 2003; Sallusto et al. 2000; Ansari et al. 2007; Fife et al. 2000). As such, numerous approaches have been employed to modulate GPCRs activities ranging from blocking antibodies to small molecule inhibitors (Loberg et al. 2007; Onai et al. 2000; Coffield et al. 2003). Unfortunately however, most of these strategies failed or had multiple limitations such as toxicity, lack of target specificity, paracrine bystander effects or in vivo inefficacy (Onai et al. 2000; Coffield et al. 2003; Engel et al. 2000).

A novel approach for GPCR modulation could be combinatorial fusokines. In other words, the fusion of 2 different cytokine cDNAs as one open reading frame that might lead to a new compound with unanticipated pharmacological properties as previously reported (Rafei et al. 2006). Recently, it was found that a 4-amino acid (aa) truncation at the N-terminus of CCL2 (mpCCL2) leads to the generation of MCP-1 (5-76) which can completely reverse the biochemical property of the molecule from agonist to antagonist (McQuibban et al. 2002). The present inventors have previously demonstrated the inhibitory influence of mpCCL2 on both humoral and cellular pathologies by blocking the generation of inhibitory antibodies following recombinant factor VIII immunization in haemophilic hosts (Rafei et al. 2008), and for the alleviation of EAE disease score (Rafei et al. 2009 a and b).

Chemokines and their receptors are involved in normal physiological responses but they can, under certain circumstances, exacerbate pathological immune reactions (Luther et al. 2001). For example, CCR2 is largely implicated in the pathophysiology of graft-versus host disease, EAE, inflammatory bowel disease and many more pathologies (Israel et al. 2004; Cheung et al. 2008; Terwey et al. 2005; Huang et al. 2001; Uguccioni et al. 1999; Shahrara et al. 2008). As a result, GPCRs have generated considerable interest in the pharmaceutical industry as drug targets. Various difficulties, however, were encountered in generating compounds that can specifically target CCRs without side effects. For instance, the development of intrakine (Onai et al. 2000) or degrakine molecules (Coffield et al. 2003), which are specific chemokines linked to an endoplasmic reticulum (ER) retention signal sequence (KDEL) on their carboxy termini, have been shown to sequester target GPCRs in the ER to prevent their transport to the cell surface or induce their degradation. Even though efficient in preventing or reducing chemokine stimulation, these molecules were linked to intracellular toxicity not to mention their passive diffusion outside of the cell (Coffield et al. 2003). Nevertheless, transducing target cells is required for the success of this strategy, an approach that is unfeasible in the context of ubiquitous expression of target GPCR.

SUMMARY OF THE DISCLOSURE

The present inventors have combined GMCSF and truncated CCL2 and found that the generated molecule, referred to as GMME1, triggered dramatic $Ca^{2+}$ influx and apoptosis by disrupting normal CCR2 behaviour on target cells. In addition, GMME1 allowed the xenograft of human cells in immunocompetent mice with noticeable lymphocyte-depletion in the spleen.

Accordingly, in one aspect, the present disclosure provides a conjugate protein comprising a GM-CSF or fragment thereof linked to a truncated CCL2. In one embodiment, the GM-CSF or fragment thereof is linked to the truncated CCL2 by a peptide linker. In another embodiment, the linker has 1 to 15 amino acids. In yet another embodiment, the GM-CSF lacks the last 11 carboxy terminal amino acids. In another embodiment, the truncated CCL2 lacks the first 5 amino acids at the N-terminal end. In a further embodiment, the conjugate protein has the amino acid sequence shown in SEQ ID NO:2 or 4 or a homolog or analog thereof.

In another aspect, the present disclosure provides a nucleic acid molecule comprising a nucleic acid sequence encoding a conjugate protein comprising a GM-CSF or fragment thereof linked to a truncated CCL2. In one embodiment, the nucleic acid molecule encoding the conjugate protein has the nucleotide sequence shown in SEQ ID NO:1 or 3 or a homolog or analog thereof. In a further embodiment, the disclosure provides an expression vector comprising the nucleic acid operably linked to an expression control sequence. In yet another embodiment, the present disclosure provides a cell comprising the expression vector or progeny of said cell wherein said cell expresses the conjugate protein.

In a further aspect, the disclosure provides a method of suppressing an immune response comprising administering an effective amount of a conjugate protein comprising a GM-CSF or fragment thereof linked to a truncated CCL2 or a nucleic acid encoding the conjugate protein to an animal or cell in need thereof. In one embodiment, graft rejection of a transplanted organ, tissue or cell is prevented or inhibited. The organ, tissue or cell can be xenogeneic or allogeneic. In another embodiment, an autoimmune disease is prevented or inhibited. In one embodiment, the autoimmune disease is multiple sclerosis, inflammatory bowel disease, rheumatoid arthritis or systemic lupus erythematosus. In yet another embodiment, graft versus host disease is prevented or inhibited. In a further embodiment, CCR2 homodimerization is inhibited.

In yet another aspect, the disclosure provides a method of enhancing or promoting cell death comprising administering an effective amount of a conjugate protein comprising a GM-CSF or fragment thereof linked to a truncated CCL2 or a nucleic acid encoding the conjugate protein to an animal or cell in need thereof. In one embodiment, the disclosure provides a method of treating cancer comprising administering an effective amount of a conjugate protein comprising a GM-CSF or fragment thereof linked to a truncated CCL2 or a nucleic acid encoding the conjugate protein to an animal or cell in need thereof. In a particular embodiment, the cancer cells express CCR2. In another embodiment, the disclosure provides a method of treating a CCR2-mediated condition or disease comprising administering an effective amount of a conjugate protein comprising a GM-CSF or fragment thereof linked to a truncated CCL2 or a nucleic acid encoding the conjugate protein to an animal or cell in need thereof. In one embodiment, the CCR2-mediated condition is obesity.

In a further aspect, the disclosure provides a pharmaceutical composition comprising an effective amount of a conjugate protein comprising a GM-CSF or fragment thereof linked to a truncated CCL2 or a nucleic acid encoding the conjugate protein in admixture with a suitable diluent or carrier.

In yet further aspect, the disclosure provides a screening assay for determining whether or not a compound is an immune suppressant, anti-obesity agent or tumoricidal agent comprising a) incubating the compound with cells that express CCR2; and b) determining the effect of the compound on the homodimerization of CCR2 in the cells; wherein a decrease in homodimerizaton as compared to a control indicates that the compound is an immune suppressant, anti-obesity agent or tumoricidal agent.

In another embodiment, the disclosure provides a screening assay for determining whether or not a compound is an immune suppressant, anti-obesity agent or tumoricidal agent comprising a) incubating the compound with cells that express CCR2 in the presence of GMME1; and b) determining whether the compound competes with GMME1; wherein competition with GMME1 indicates that the compound is an immune suppressant, anti-obesity agent or tumoricidal agent.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION OF THE DISCLOSURE

Figure 1:
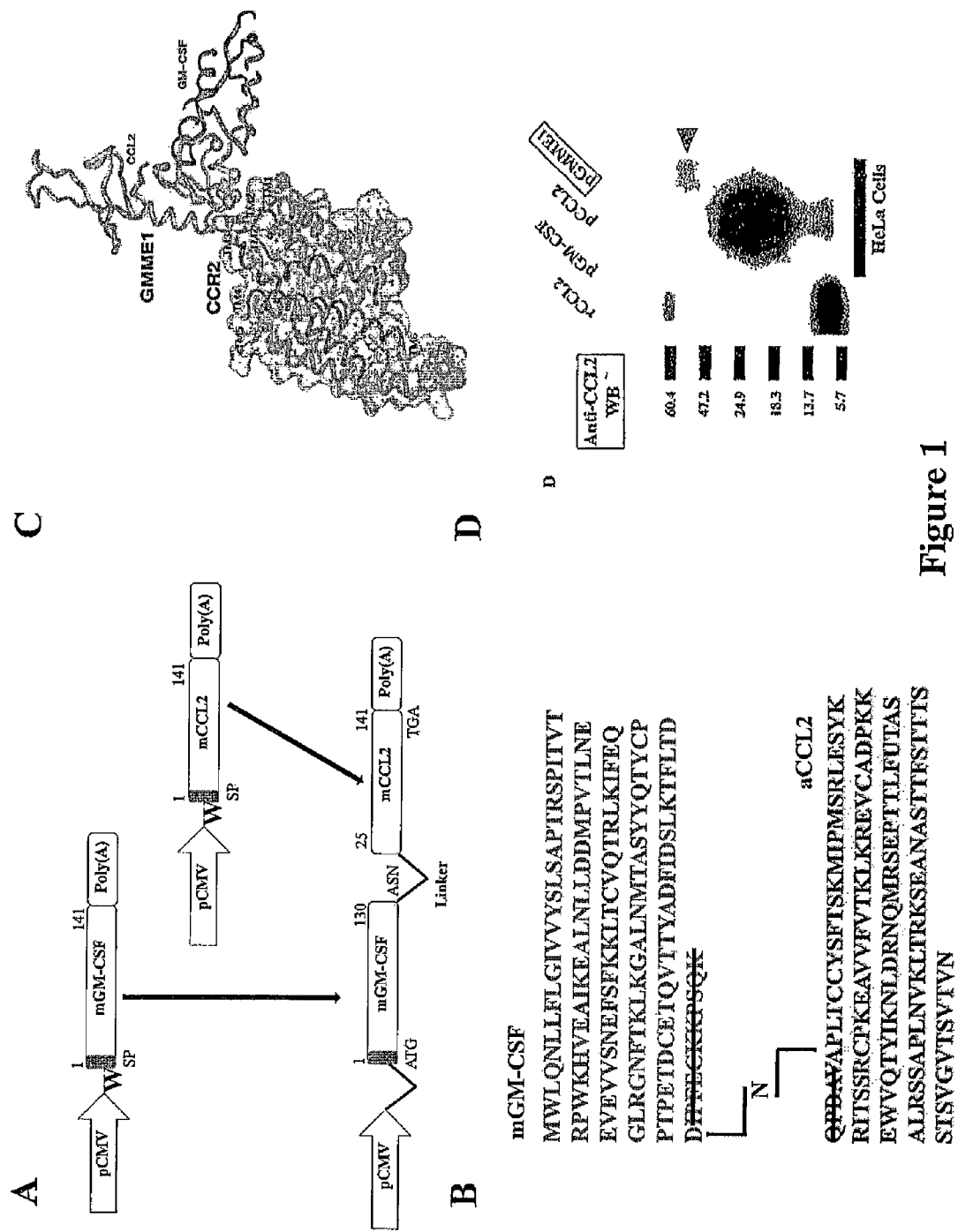
FIG. 1 shows the construction and expression of murine GMME1. (A) Schematic representation of the GMME1 engineering. (B) Schematic representation of the GMME1 amino acid sequence (SEQ ID NO:2). (C) Predicted structural model of GMME1. (D) Expression of GMME1 in conditioned media (CM) collected from transiently transfected HeLa cells and demonstrated by denaturing immunoblotting and detection with anti-CCL2 and anti-GM-CSF polyclonal antisera. GM-CSF and CCL2 were used as positive control.

The present inventors have developed a novel fusokine, called GMME1, with the capacity of specifically targeting and inducing apoptosis in CC-chemokine receptor 2 or CCR2-expressing cells. This novel fusokine allows cellular xenograft of somatic cells and can be used as a recombinant protein systemically in autoimmune diseases where it can induce apoptosis of lymphocytes and macrophages or for local treatment of tumors where it can induce apoptosis of cancer cells that express CCR2.

A. GM-CSF and Truncated CCL2 Conjugates

The present disclosure relates to conjugates of GM-CSF and truncated CCL2 that can be used in various therapeutic applications as described in Section B.

Accordingly, the present disclosure provides a conjugate protein comprising a GM-CSF or a fragment thereof linked to a truncated CCL2.

The term "CCL2" as used herein refers to Chemokine (C-C motif) ligand 2 from any species or source. CCL2 is also known as MCP-1 (monocyte chemotactic protein 1), MCAF (monocyte chemotactic and activating factor), Smc-cf (smooth muscle cell chemotactic factor), HC11, LDCF (lymphocyte derived chemotactic factor), GDCF-2 (glioma derived monocyte chemotactic factor), and TDCF (tumor-derived chemotactic factor). Mouse CCL2 has the Genbank accession number NM_011333 and human CCL2 has the Genbank accession number NM_002982. CCL2, a chemokine of the CC family, was first characterized as a monocyte-chemoattracting protein. Mouse CCL2 cDNA encodes a 148 amino acid (aa) residue with a putative 23 aa signal peptide that is cleaved to generate the mature protein with a molecular weight of 8525 Da. The truncation of most of the C-terminal extension could be due to post-translational modification. Human CCL2 cDNA encodes a 99 amino acid (aa) residue with a putative 23 aa signal peptide that is cleaved to generate the mature protein with a molecular weight of 11030 Da (calculated with an internet based tool). CCL2 can be produced by many cells, including macrophages, DCs, endothelial cells and fibroblasts.

The term "truncated CCL2" as used herein refers to a CCL2 protein which lacks at least one residue from the N-terminus and which acts as an antagonist as compared to full length CCL2. The truncated CCL2 optionally is also processed at the C-terminal end, for example, in a manner similar to native CCL2. In an embodiment, the truncated CCL2 comprises murine CCL2 lacking the first 5 amino acids at the N-terminal end of the mature protein. In another embodiment the truncated CCL2 comprises murine CCL2 lacking the first 4 amino acids at the N-terminal end of the mature protein. In yet another embodiment, the truncated CCL2 comprises amino acids 6-76 of murine CCL2. In another embodiment, the truncated CCL2 comprises human CCL2 lacking the first 5 amino acids at the N-terminal end of the mature protein. In another embodiment, the truncated CCL2 comprises human CCL2 lacking the first 4 amino acids at the N-terminal end of the mature protein. In yet another embodiment, the truncated CCL2 comprises amino acids 6-76 of human CCL2.

The term "GM-CSF" as used herein refers to granulocyte macrophage colony stimulating factor from any species or source and includes the full-length protein as well as fragments or portions of the protein. Mouse GM-CSF has the Genbank accession number NM 009969 and human GM-CSF has the Genbank accession number BC108724. In one embodiment, the GM-CSF is from human or mouse. The term "GM-CSF fragment" as used herein means a portion of the GM-CSF peptide that contains at least 10%, 20%, 30%, 40%, 50%, 60%, 70%, 80%, 90%, 95%, or more of the entire length of the GM-CSF polypeptide that when conjugated to truncated CCL2 provides for the inhibition of CCR2 homodimerization probably via additional steric hindrance and/or increased biological availability. In another embodiment, the GM-CSF protein lacks the last 11 carboxy terminal amino acid sequences as compared to full length GM-CSF.

The term "conjugate protein" as used herein means a conjugate that comprises GM-CSF or a fragment thereof physically linked to a truncated CCL2 and which is able to inhibit CCR2 homodimerization. In a specific embodiment, the conjugate is a fusion protein (or fusokine) wherein a nucleic acid sequence encoding GM-CSF or a fragment thereof is operably linked to a nucleic acid sequence encoding a truncated CCL2 and the chimeric sequence is transfected or transduced into a host cell and produced as a recombinant fusion protein.

In an embodiment, the GM-CSF or fragment thereof and the truncated CCL2 are linked by a peptide linker. The peptide linker can be any size provided it does not interfere with the function of the conjugate protein. In one embodiment, the peptide linker is from about 1 to about 15 amino acids in length, more specifically from about 1 to about 10 amino acids, and most specifically from about 1 to about 6 amino acids. In a specific embodiment, the peptide linker forms an intercytokine bridge.

One of skill in the art can appreciate that the conjugate protein can also be formed by linking the two proteins in vitro, for example, using chemical cross-linkers. For example, the proteins may be coupled using heterobifunctional thiol-containing linkers as described in WO 90/10457, N-succinimidyl-3-(2-pyridyldithio-proprionate) or N-succinimidyl-5 thioacetate.

In an embodiment, GM-CSF is linked to CCL2 lacking the first 5 N-terminal amino acids. This conjugate protein is abbreviated GMME1 in the present disclosure. In one embodiment, the conjugate protein is murine and has the amino acid sequence shown in SEQ ID NO:2 or an analog or homolog thereof. This fusion protein is abbreviated mGMME1 in the present disclosure. In another embodiment, the conjugate protein is human and has the amino acid sequence shown in SEQ ID NO:4 or an analog or homolog thereof. This fusion protein is abbreviated hGMME1 in the present disclosure.

The disclosure also includes nucleic acid molecules that encode the conjugate proteins described herein. The nucleic acid molecule is preferably a chimeric nucleic acid sequence that comprises a) a nucleic acid sequence encoding GM-CSF or a fragment thereof linked to b) a nucleic acid sequence encoding a truncated CCL2.

The chimeric sequence optionally also includes a sequence encoding a peptide linker. Accordingly, the present disclosure also includes a chimeric nucleic acid sequence that comprises a) a nucleic acid sequence encoding GM-CSF or a fragment thereof linked to b) a nucleic acid sequence encoding a peptide linker linked to c) a nucleic acid sequence encoding a truncated CCL2.

In one embodiment, the chimeric nucleic acid sequence is murine and has the nucleotide sequence shown in SEQ ID NO:1, or a homolog or analog thereof. In another embodiment, the chimeric nucleic acid sequence is human and has the nucleotide sequence shown in SEQ ID NO:3, or a homolog or analog thereof.

The term "homolog" means those amino acid or nucleic acid sequences which have slight or inconsequential sequence variations from the sequences in SEQ ID NOs:1-4, i.e., the sequences function in substantially the same manner. The variations may be attributable to local mutations or structural modifications. Sequences having substantial homology include nucleic acid sequences having at least 65%, more preferably at least 85%, and most preferably 90-95% identity with the sequences as shown in SEQ ID NOs:1-4. Sequence identity can be calculated according to methods known in the art. Nucleic acid sequence identity is most preferably assessed by the algorithm of BLAST version 2.1 advanced search. BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schaffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

In one embodiment, the CCL2 used is a mutein of CCL2 as described in US20040185450, incorporated herein in its entirety, covering MCP-1 mutant proteins, antibodies, compositions and methods. The muteins contain at least one of the following substitutions: Tyr13His, Asn14Asp or Asn14Gln, Phe15Tyr, Thr16Val, Glu39Asp, Ala40Ser, Val41Ile, Phe43Tyr, Thr45Val, Ile51Val, Ala53Ser, Trp59His, His66Trp, or Leu67Ile with a length of at least 15 contiguous amino acids between the substituted amino acids, having 90 to 99% homology (which corresponds to 81% of homology if all locations are mutated but 98% if only one is mutated).

The term "analog" means an amino acid or nucleic acid sequence which has been modified as compared to the sequence of SEQ ID NOs:1-4 wherein the modification does not alter the utility of the sequence (e.g. as immune suppressant) as described herein. The modified sequence or analog may have improved properties over the sequences shown in SEQ ID NOs:1-4. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules shown in SEQ ID NO:1 or 3. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The disclosure also includes sequences that hybridize to the sequences shown in SEQ ID NO:1 or 3 or a fragment thereof and maintain the property of inhibiting CCR2 homodimerization. The term “sequence that hybridizes” means a nucleic acid sequence that can hybridize to a sequence of SEQ ID NO:1 or 3 under stringent hybridization conditions. Appropriate “stringent hybridization conditions” which promote DNA hybridization are known to those skilled in the art, or may be found in Current Protocols in Molecular Biology, John Wiley & Sons, N.Y. (1989), 6.3.1-6.3.6. The term “stringent hybridization conditions” as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.−16.6(Log 10[Na+])+0.41(% (G+C)−600/I). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5× sodium chloride/sodium citrate (SSC)/5×Denhardt’s solution/1.0% SDS at Tm (based on the above equation)−5° C., followed by a wash of 0.2×SSC/0.1% SDS at 60° C.

It will be appreciated that analogs/homologs of the conjugate proteins described herein can also be prepared by first preparing or using an analog or homolog of GM-CSF or truncated CCL2 or both prior to preparing the chimeric nucleic acid sequence.

The conjugate proteins described herein may be modified to contain amino acid substitutions, insertions and/or deletions that do not alter the inhibition of CCR2 homodimerization properties of the protein. Conserved amino acid substitutions involve replacing one or more amino acids of the conjugate protein with amino acids of similar charge, size, and/or hydrophobicity characteristics. When only conserved substitutions are made the resulting analog should be functionally equivalent to the conjugate protein. Non-conserved substitutions involve replacing one or more amino acids of the conjugate protein with one or more amino acids which possess dissimilar charge, size, and/or hydrophobicity characteristics.

The conjugate proteins described herein may be modified to make it more therapeutically effective or suitable. For example, the conjugate protein or peptides of the present disclosure may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesulphonic acids.

The disclosure also includes expression vectors comprising a chimeric nucleic acid sequence comprising a) a nucleic acid sequence encoding GM-CSF or a fragment thereof linked to b) a nucleic acid sequence encoding a truncated CCL2. In a specific embodiment, the chimeric nucleic acid sequence includes a sequence that encodes a peptide linker as described above.

Possible expression vectors include but are not limited to cosmids, plasmids, artificial chromosomes, viral vectors or modified viruses (e.g. replication defective retroviruses, adenoviruses and adeno-associated viruses), so long as the vector is compatible with the host cell used. The expression vectors are “suitable for transformation of a host cell”, which means that the expression vectors contain a nucleic acid molecule of the disclosure and regulatory sequences selected on the basis of the host cells to be used for expression, which is operatively linked to the nucleic acid molecule. Operatively linked or operably linked is intended to mean that the nucleic acid is linked to regulatory sequences in a manner which allows expression of the nucleic acid.

The disclosure therefore contemplates a recombinant expression vector of the disclosure containing a nucleic acid molecule of the disclosure, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (for example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the GM-CSF or CCL2 sequences and/or their flanking regions.

The recombinant expression vectors of the disclosure may also contain a selectable marker gene which facilitates the selection of host cells transformed or transfected with a recombinant molecule of the disclosure. Examples of selectable marker genes are genes encoding a protein such as G418 and hygromycin which confer resistance to certain drugs, (β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the disclosure and in particular to determine the effect of a mutation on expression and phenotype. It will be appreciated that selectable markers can be introduced on a separate vector from the nucleic acid of interest.

The recombinant expression vectors may also contain genes which encode a moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins of the disclosure may be expressed in yeast cells or mammalian cells. Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as *Escherichia coli* (Zhang et al., Science 303(5656): 371-3 (2004)).

Mammalian cells suitable for carrying out the present disclosure include, among others: B16FO cells, 293T cells, Mesenchymal Stromal Cell (MSCs), COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) NS-1 cells, and U87 (human glioma cell line).

The mammalian cells can also be derived from a human or animal and include stem cells (including hematopoietic stem cells), somatic cells, progenitor cells (including endothelial progenitor cells), fibroblasts, lymphocytes, and mesenchymal stem cells (MSCs) that have been genetically engineered to express the conjugate proteins described herein. Such cells can be used in the therapeutic applications described in Section B.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, Calif., U.S.A.).

Alternatively, the conjugate proteins of the disclosure may also be expressed in non-human transgenic animals such as, rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866). The disclosure also includes tissues and cells derived from such animals.

B. Therapeutic Methods

The disclosure includes all applications of the conjugate proteins described herein, some of which are described below.

1. Immune Suppression

CCR2 homodimerization was inhibited following GMME1 binding and blockade of β-arrestin recruitment to the receptor impeding therefore CCR2 recycling and desensitization of the cell to external stimuli. As a result, strong calcium ($Ca^{2+}$) influx is triggered inducing the activation of pro-caspase 3 and thus lymphocyte and macrophage cell death in vitro.

Accordingly, in one aspect, the present disclosure provides a method of suppressing an immune response comprising administering an effective amount of a conjugate protein comprising a GM-CSF or fragment thereof linked to a truncated CCL2 or a nucleic acid sequence encoding the conjugate protein to an animal or cell thereof in need of such treatment. The disclosure includes a use of an effective amount of a conjugate protein comprising a GM-CSF or fragment thereof linked to a truncated CCL2 or a nucleic acid sequence encoding the conjugate protein to suppress an immune response. The disclosure includes a use of an effective amount of a conjugate protein comprising a GM-CSF or fragment thereof linked to a truncated CCL2 or a nucleic acid sequence encoding the conjugate protein to prepare a medicament to suppress an immune response. In another embodiment, the disclosure provides a conjugate protein comprising a GM-CSF or fragment thereof linked to a truncated CCL2 for use in suppressing an immune response. In one embodiment, suppressing the immune response comprises depleting lymphocytes and/or macrophages.

The term "administering a conjugate protein" includes both the administration of the conjugate protein as well as the administration of a nucleic acid sequence encoding the conjugate protein to an animal or to a cell in vitro or in vivo. The term "administering" also includes the administration of a cell that expresses the conjugate protein.

The term "a cell" includes a single cell as well as a plurality or population of cells. Administering to a cell includes administering in vitro (or ex vivo) as well as in vivo.

Administration of an "effective amount" of the conjugate protein and nucleic acid of the present disclosure is defined as an amount effective, at dosages and for periods of time necessary to achieve the desired result. The effective amount of the conjugate protein or nucleic acid of the disclosure may vary according to factors such as the disease state, age, sex, and weight of the animal. Dosage regimens may be adjusted to provide the optimum therapeutic response. For example, several divided doses may be administered daily or the dose may be proportionally reduced as indicated by the exigencies of the therapeutic situation. The mode of administration (e.g. in vivo by injection or ex vivo in culture) will also impact the dosage regime.

The term "animal" as used herein includes all members of the animal kingdom including humans.

Once a particular conjugate protein or analog or homolog is prepared, one of skill in the art can readily determine whether or not it can suppress an immune response. For example, determining whether a particular conjugate protein or fragments thereof can suppress an immune response can be assessed using known in vitro immune assays including, but not limited to, inhibiting a mixed leukocyte reaction (MLR); inhibiting a cytotoxic T cell response; inhibiting interleukin-2 production; inhibiting IFN-γ production; inhibiting a Th1 cytokine profile; inhibiting immunoglobulin production; and any other assay that would be known to one of skill in the art to be useful in detecting immune suppression or lymphocyte or macrophage depletion. And known apoptotic assays, including but not limited to, calcium influx assay, induction of pro-caspase 3, chemotaxis assay, annexin V/PI costaining, and TUNEL assays can also be readily used.

(i) Graft Rejection

In vivo, all GMME1-expressing cellular xenografts implanted in immunocompetent C57Bl/6 mice survived due to lymphocyte-depletion occurring in the spleen without any noticeable changes in circulating white blood cell (WBC) numbers. However, in vitro analysis of cell death using, for example, HEK293T cells expressing CCR2 or macrophages was performed using a western blot directed against cleaved caspase-3, or by performing a flow cytometry analysis using Annexin-V/Propidium iodine (PI) co-staining and one can see clearly the percentage of dead cells, or cells undergoing apoptosis.

Accordingly, in another aspect, the present disclosure provides a method of suppressing an immune response to a transplanted organ, cell or tissue in a recipient animal comprising administering an effective amount of a conjugate protein comprising a GM-CSF or fragment thereof linked to a truncated CCL2 or a nucleic acid sequence encoding the conjugate protein to the recipient animal, optionally prior to the transplantation of the organ or tissue. The disclosure includes a use of an effective amount of a conjugate protein comprising a GM-CSF or fragment thereof linked to a truncated CCL2 or a nucleic acid sequence encoding the conjugate protein to suppress an immune response to a transplanted organ, cell or tissue. The disclosure also includes a use of an effective amount of a conjugate protein comprising a GM-CSF or fragment thereof linked to a truncated CCL2 or a nucleic acid sequence encoding the conjugate protein to prepare a medicament to suppress an immune response to a transplanted organ, cell or tissue. The disclosure further includes a conjugate protein comprising a GM-CSF or fragment thereof linked to a truncated CCL2 or a nucleic acid sequence encoding the conjugate protein for use in suppressing an immune response to a transplanted organ, cell or tissue.

The recipient can be any member of the animal kingdom including rodents, pigs, cats, dogs, ruminants, non-human primates and preferably humans. The organ, cell or tissue to be transplanted can be from the same species as the recipient (allograft or allogeneic) or can be from another species (xenograft or xenogeneic). The tissues, cells or organs can be any tissue or organ including heart, liver, kidney, lung, pancreas, pancreatic islets, brain tissue, cornea, bone, intestine, skin and haematopoietic cells and stem cells.

In one embodiment, the organ, cells or tissue to be transplanted may be transduced with a nucleic acid construct encoding the conjugate protein prior to transplantation into the graft recipient.

One of skill in the art can determine whether or not a particular conjugate protein or fragment thereof is useful in preventing graft rejection. As mentioned above, one of skill in the art can readily test a conjugate protein or fragment thereof for its ability to suppress an immune response using known in vitro assays. In addition the conjugate protein or fragment thereof can also be tested for its ability to prevent graft rejection in an animal model. For example, one could use the xenotransplant animal model described above.

The method of the disclosure may be used to prevent graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and enzyme or immune deficiencies, for example.

Accordingly, in another embodiment, the present disclosure provides a method of preventing or inhibiting graft versus host disease in a recipient animal receiving an organ or tissue transplant comprising administering an effective amount of a conjugate protein comprising a GM-CSF or fragment thereof linked to a truncated CCL2 or a nucleic acid sequence encoding the conjugate protein to the organ or tissue, optionally prior to the transplantation in the recipient animal. The disclosure also includes a use of an effective amount of a conjugate protein comprising a GM-CSF or fragment thereof linked to a truncated CCL2 or a nucleic acid molecule encoding the conjugate protein to prevent or inhibit graft versus host disease. The disclosure also includes a use of an effective amount of a conjugate protein comprising a GM-CSF or fragment thereof linked to a truncated CCL2 or a nucleic acid sequence encoding the conjugate protein to prepare a medicament to prevent or inhibit graft versus host disease. The disclosure further includes a conjugate protein comprising a GM-CSF or fragment thereof linked to a truncated CCL2 or a nucleic acid sequence encoding the conjugate protein for use in preventing or inhibiting graft versus host disease in a recipient animal receiving an organ or tissue transplant.

(ii) Autoimmune Disease

Due to the immune suppressive properties of the conjugate protein, the method of the present disclosure may be used to treat or prevent autoimmune disease. In an autoimmune disease, the immune system of the host fails to recognize a particular antigen as "self" and an immune reaction is mounted against the host's tissues expressing the antigen.

Normally, the immune system is tolerant to its own host's tissues and autoimmunity can be thought of as a breakdown in the immune tolerance system.

Accordingly, in a further embodiment, the present disclosure provides a method of preventing or treating an autoimmune disease comprising administering an effective amount of a conjugate protein comprising a GM-CSF or fragment thereof linked to a truncated CCL2, or a nucleic acid sequence encoding the conjugate protein to an animal having, suspected of having, or susceptible to having an autoimmune disease. The disclosure includes a use of an effective amount of a conjugate protein comprising a GM-CSF or fragment thereof linked to a truncated CCL2 or a nucleic acid molecule encoding the conjugate protein to prevent or treat an autoimmune disease. The disclosure also includes a use of an effective amount of a conjugate protein comprising a GM-CSF or fragment thereof linked to a truncated CCL2 or a nucleic acid molecule encoding the conjugate protein to prepare a medicament to prevent or treat an autoimmune disease. The disclosure further includes a conjugate protein comprising a GM-CSF or fragment thereof linked to a truncated CCL2 or a nucleic acid molecule encoding the conjugate protein for use in preventing or treating an autoimmune disease.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

Autoimmune diseases that may be treated or prevented according to the present disclosure include, but are not limited to, arthritis, type 1 insulin-dependent diabetes mellitus, adult respiratory distress syndrome, inflammatory bowel disease, Crohn's disease, ulcerative colitis, atopic dermatitis, dermatitis, meningitis, thrombotic thrombocytopenic purpura, Sjögren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease. In one embodiment, the autoimmune disease is multiple sclerosis or rheumatoid arthritis. In another embodiment, the autoimmune disease is rheumatoid arthritis, psoriasis, psoriatic arthritis, atopic dermatitis, multiple sclerosis, Crohn's disease, ulcerative colitis or type I diabetes.

One of skill in the art can determine whether or not a particular conjugate protein or fragment thereof is useful in preventing autoimmune disease. As mentioned previously, one of skill in the art can readily test a conjugate protein or fragment thereof for its ability to suppress an immune response using known in vitro assays. In addition the conjugate protein or fragment thereof can also be tested for its ability to prevent autoimmune in an animal model. For example, one could use the experimental allergic encephalomyelitis (EAE) model described below wherein the ability of a conjugate protein to inhibit IFN-γ secretion is assessed. The EAE model is an animal model for multiple sclerosis. Further, many other autoimmune animal models are available, including, but not limited to, animal models of inflammatory bowel disease (induced by immunization, or developing in cytokine-knockout mice), and models of autoimmune myocarditis and inflammatory eye disease.

2. Promoting Cell Death

Human and mouse GMME1 have been shown to be tumoricidal upon their addition on the human multiple myeloma cell line U266 and on the mouse lymphoma cell line EG7, respectively.

Accordingly, the conjugate proteins disclosed herein can be used to promote the death of a cell. In one embodiment, the present disclosure provides a method of enhancing or promoting cell death comprising administering an effective amount of a conjugate protein or a nucleic acid sequence encoding the conjugate protein to an animal or cell in need thereof. The disclosure includes the use of an effective amount of conjugate protein comprising a GM-CSF or fragment thereof linked to a truncated CCL2 or a nucleic acid molecule encoding the conjugate protein to enhance or promote cell death. The disclosure also includes a use of an effective amount of a conjugate protein comprising a GM-CSF or fragment thereof linked to a truncated CCL2 or a nucleic acid sequence encoding the conjugate protein to prepare a medicament to enhance or promote cell death. The disclosure further includes a conjugate protein comprising a GM-CSF or fragment thereof linked to a truncated CCL2 or a nucleic acid sequence encoding the conjugate protein for use in enhancing or promoting cell death.

The cell may be any cell for which it is desired to promote programmed cell death. Non-limiting examples include cancer cells as well as any cell type that expresses CCR2. The conjugate protein may be administered in vivo or ex vivo to a cell which is then administered. The conjugate protein may be provided alone or with a pharmaceutically acceptable carrier. The carrier may include a diluent. The carrier may include an appropriate adjuvant, a herpes virus, a liposome, a microencapsule, a neuronal cell receptor ligand, a neuronal-specific virus, a polymer encapsulated cell or a retroviral vector. The pharmaceutically acceptable carrier may include an aerosol, intravenous, oral or topical carrier.

Another embodiment of the present disclosure is a method for treating cancer comprising administering an effective amount of a conjugate protein comprising a GM-CSF or fragment thereof linked to a truncated CCL2 or a nucleic acid sequence encoding the conjugate protein to an animal or cell in need thereof. The disclosure includes the use of an effective amount of a conjugate protein comprising a GM-CSF or fragment thereof linked to a truncated CCL2 or a nucleic acid molecule encoding the conjugate protein to treat cancer. The disclosure also includes a use of an effective amount of a conjugate protein comprising a GM-CSF or fragment thereof linked to a truncated CCL2 or a nucleic acid sequence encoding the conjugate protein to prepare a medicament to treat cancer. The disclosure further includes a conjugate protein comprising a GM-CSF or fragment thereof linked to a truncated CCL2 or a nucleic acid sequence encoding the conjugate protein for use in treating cancer. In one embodiment, the cancer cells are known to express CCR2. Non-limiting examples include solid tumors and cancers, multiple myeloma, lymphoma, chronic lymphocytic leukemia, chronic myelocytic leukemia, malignant myeloma, Hodgkin's disease, bladder cancer, cervical cancer, colon cancer, lung cancer and stomach cancer. In one embodiment, the cancer is multiple myeloma, lymphoma, breast or prostate cancer.

Another embodiment of the present disclosure is a method for treating a CCR2-mediated condition or disease comprising administering an effective amount of a conjugate protein comprising a GM-CSF or fragment thereof linked to a truncated CCL2 or a nucleic acid sequence encoding the conjugate protein to an animal or cell in need thereof. The disclosure includes the use of an effective amount of a conjugate protein comprising a GM-CSF or fragment thereof linked to a truncated CCL2 or a nucleic acid molecule encoding the conjugate protein to treat a CCR2-mediated condition or disease. The disclosure also includes a use of an effective amount of a conjugate protein comprising a GM-CSF or fragment thereof linked to a truncated CCL2 or a nucleic acid sequence encoding the conjugate protein to prepare a medicament to treat a CCR2-mediated condition or disease. The disclosure further includes a conjugate protein comprising a GM-CSF or fragment thereof linked to a truncated CCL2 or a nucleic acid sequence encoding the conjugate protein for use in treating a CCR2-mediated condition or disease. In one embodiment, the CCR2-mediated condition or disease is an ophthalmic disorder, uveitis, atherosclerosis, nephritis, organ allograft rejection, fibroid lung, renal insufficiency, type II diabetes and diabetic complications, diabetic nephropathy, diabetic retinopathy, diabetic retinitis, diabetic microangiopathy, obesity, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders or glomerulonephritis. In one embodiment, the CCR2-mediated condition or disease is obesity.

It will be appreciated that the conjugates of the disclosure can generally be used for treating other symptoms that can be alleviated by promoting death in the affected organs or tissues.

In all of the above therapeutic applications, the conjugate protein can be administered as a protein or as a nucleic acid molecule encoding the protein. In one embodiment, as noted above, expression of the conjugate protein occurs as a result of the administration of nucleic acid encoding the conjugate protein to an organism. Thus, the conjugate protein will be produced endogenously in the organism, rather than administered in a protein form. The therapy may be done at an embryonic stage of the organism, such that the germ cells of the organism contain the conjugate protein nucleic acid, resulting in a transgenic organism, or at a later stage of development to specific somatic cells, such that only a particular tissue or portion of a tissue contains the conjugate protein nucleic acid. Techniques for nucleic acid therapy are well known in the art, as are the techniques for the creation of transgenic organisms (Carl A. Pinkert. Transgenic Animal Technology: A Laboratory Handbook. Academic Press; 1st edition (1994)).

For example, pigs and goats can be used as potential transgenic animals producing the conjugate protein. In one embodiment pigs are used in view of the fact that they possess high homology to humans in terms of MHC molecules and they are considered as a potential source of tissue and organs, in particular pancreas, heart, kidney and cornea amongst others.

It is to be understood that the administration of the conjugate protein nucleic acid in gene therapy may take several forms, all of which are included in the scope of the present disclosure. The nucleic acid encoding the conjugate protein may be administered in such a manner as to add the conjugate protein nucleic acid to the genome of the cell or the organism. For example, administering a nucleic acid encoding the conjugate protein, under the control of a promoter which results in an increase in expression of the conjugate protein, results in the incorporation of the nucleic acid into the genome of the cell or the organism, such that increased levels of the conjugate protein are made.

Construction of appropriate expression vehicles and vectors for therapeutic applications will depend on the organism to be treated and the purpose of the gene therapy. The selection of appropriate promoters and other regulatory DNA will proceed according to known principles, based on a variety of known gene therapy techniques. For example, retroviral mediated gene transfer is a very effective method for therapy, as systems utilizing packaging defective viruses allow the production of recombinants which are infectious only once, thus avoiding the introduction of wild-type virus into an organism. Alternative methodologies for therapy include non-viral transfer methods, such as calcium phosphate coprecipitation, mechanical techniques, for example microinjection, membrane fusion-mediated transfer via liposomes, as well as direct DNA uptake and receptor-mediated DNA transfer.

C. Compositions

The disclosure also includes pharmaceutical compositions containing the conjugate proteins or nucleic acids disclosed herein. Such pharmaceutical compositions can be used in the therapeutic applications described in Section B, for example, in immune suppression, cancer, obesity and promoting cell death.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the disclosure can be intended for administration to humans or animals or cells or tissue in culture. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003—$20^{th}$ Edition) and in The United States Pharmacopeia: The National Formulary (USP 24 NF19) published in 1999).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as immunosuppressive drugs or antibodies to enhance immune tolerance or chemotherapeutic drugs.

In one embodiment, the pharmaceutical composition comprises an effective amount of a conjugate protein comprising a GM-CSF or fragment thereof linked to a truncated CCL2 in admixture with a pharmaceutically acceptable diluent or carrier.

Figure 2:
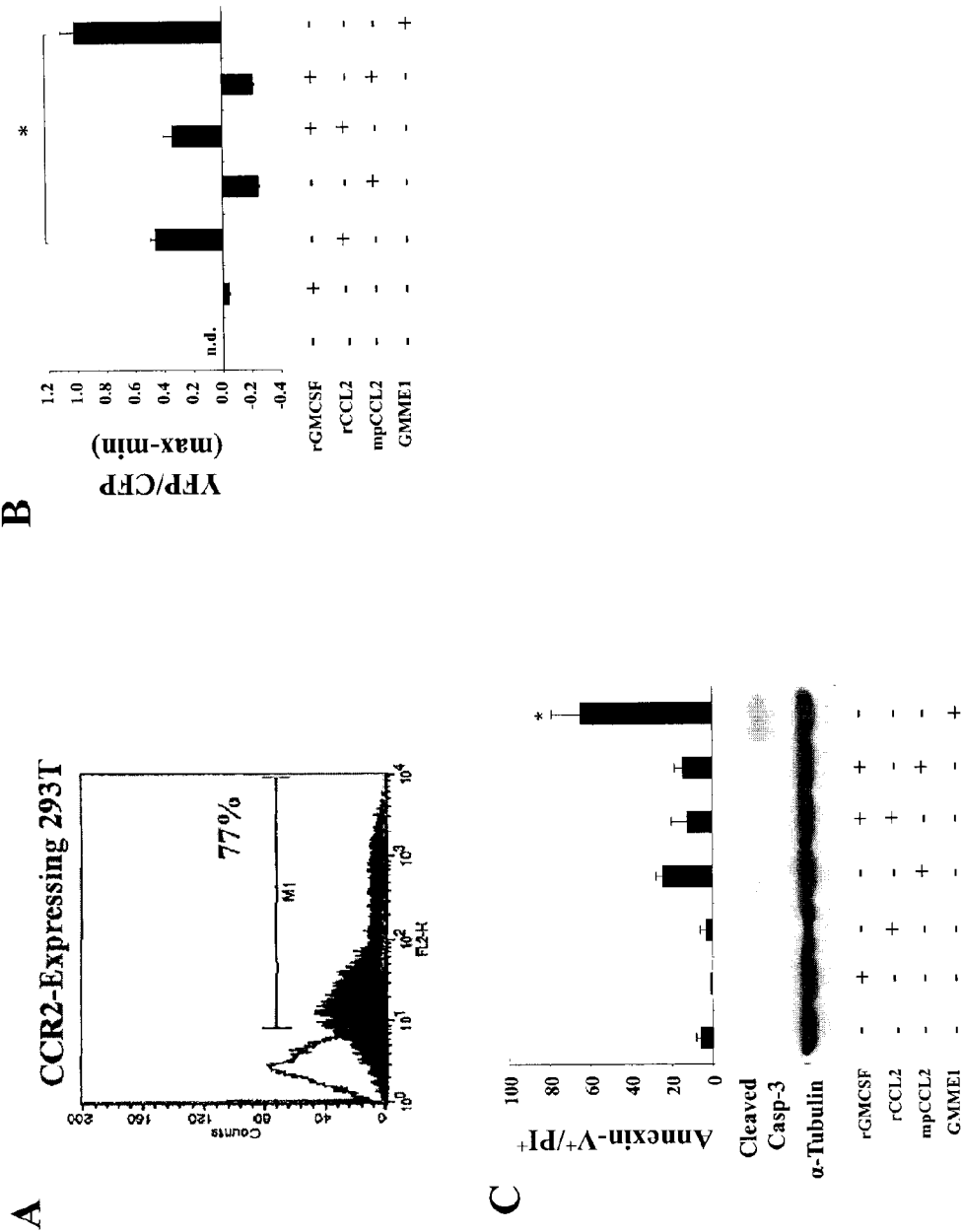
FIG. 2 shows GMME1-induced biochemical responses. (A) Murine CCR2 expression in HEK293T-cells 48 hrs after transient transfection, monitored by flow cytometry. (B) $Ca^{2+}$ mobilization by GMME1. Schematic cameleon diagram showing the binding of 4 $Ca^{2+}$ cations to the calmodulin moiety in between CFP (cyan fluorescence protein) and YFP (yellow fluorescence protein) and subsequent conformational change triggering electron transfer from CFP to YFP leading to different emission wavelength. The results are shown as differences in CFP/YFP ratios between the basal state and following ligand stimulation. (C) GMME1-induced apoptosis (upper panel). CCR2 expressing HEK293T-cells cultured for 48 hrs in the presence of equimolar concentrations of the conditions under (C) were stained for PI and Annexin-V. GMME1 induced caspase-3 cleavage (lower panel). Cell lysates from $10^6$ CCR2 expressing HEK293T-cells cultured for 48 hrs with 1 pmol of recombinant (r) GMCSF, rCCL2, mpCCL2, rGMCSF/rCCL2, rGMCSF/mpCCL2 or with GMME1, were tested for cleaved caspase-3. α-tubulin protein was used as loading control.

In another embodiment, the pharmaceutical composition comprises an effective amount of a nucleic acid molecule encoding a conjugate protein comprising a GM-CSF or fragment thereof linked to a truncated CCL2 in admixture with a pharmaceutically acceptable diluent or carrier.

D. Screening Assay

As mentioned previously, the conjugate protein described herein exerts its effect through inhibition of CCR2 homodimerization. The identification of the mechanism by which the conjugate exerts its effects allows the development of screening assays that could be used to test other compounds for immune suppressive, anti-obesity and/or tumoricidal activity.

Accordingly, the present disclosure also provides a screening assay for determining whether or not a compound is an immune suppressant, anti-obesity agent or tumoricidal agent comprising a) incubating the compound with cells that express CCR2; and b) determining the effect of the compound on the homodimerization of CCR2 in the cells; wherein a decrease in homodimerization as compared to a control indicates that the compound may be an immune suppressant, anti-obesity agent or tumoricidal agent.

CCR2 homodimerization can be determined using techniques known in the art including isothermal titration calorimetry, analytical ultrafiltration, nuclear magnetic resonance, mass spectrometry, size exclusion chromatography, electrophoresis, surface Plasmon resonance as well as bioluminescence resonance electron transfer.

In another embodiment, the disclosure provides a screening assay for determining whether or not a compound is an immune suppressant, anti-obesity agent or tumoricidal agent comprising a) incubating the compound with cells that express CCR2 in the presence of a conjugate protein of the disclosure; and b) determining whether the compound competes with the conjugate protein of the disclosure; wherein competition with GMME1 indicates that the compound is an immune suppressant, anti-obesity agent or tumoricidal agent.

Competition assays are known in the art. Competitive assays are widely used for different purposes such as agonist/antagonist interactions with a receptor or for concentration analysis for a drug of interest. In one example, an affinity-purified capture antibody pre-coated onto a microplate is used, to which a limited concentration of enzyme-linked analyte along with the non-labeled sample analyte are added simultaneously. Both analytes will then compete for the limited number of binding sites on the primary antibody. Substrate is added and hydrolyzed by the enzyme, thereby producing a color product that can be measured (exactly like an ELISA). The amount of labeled analyte bound is inversely proportional to the amount of unlabeled analyte presenting the sample (signal decreases as analyte concentration increases).

The test compound can be any compound which one wishes to test including, but not limited to, proteins, peptides, nucleic acids (including RNA, DNA, antisense oligonucleotide, peptide nucleic acids), carbohydrates, organic compounds, small molecules, natural products, library extracts, bodily fluids and other samples that one wishes to test for immune suppressive, anti-obesity or tumoricidal activity.

The cells can be any cells that either naturally express CCR2 or are transduced or transfected to express CCR2.

Once it has been determined that a test compound or conjugate does decrease the homodimerization of CCR2 or competes with the conjugate protein of the disclosure, it can be further tested for immune suppressive or tumoricidal activity using techniques known in the art including the assays described herein for the conjugate proteins of the disclosure.

The screening methods of the disclosure include high-throughput screening applications. For example, a high-throughput screening assay may be used which comprises any of the methods according to the disclosure wherein aliquots of cells transfected with CCR2 are exposed to a plurality of test compounds within different wells of a multi-well plate. Further, a high-throughput screening assay according to the disclosure involves aliquots of transfected cells which are exposed to a plurality of candidate conjugates in a miniaturized assay system of any kind. Another embodiment of a high-throughput screening assay could involve exposing a transduced cell population simultaneously to a plurality of test compounds.

The method of the disclosure may be "miniaturized" in an assay system through any acceptable method of miniaturization, including but not limited to multi-well plates, such as 24, 48, 96 or 384-wells per plate, micro-chips or slides. The assay may be reduced in size to be conducted on a micro-chip support, advantageously involving smaller amounts of reagent and other materials. Any miniaturization of the process which is conducive to high-throughput screening is within the scope of the disclosure.

EXAMPLES

Design and Characterization of Murine and Human GMME1

The murine fusokine was created by cloning a modified cDNA of mGMCSF missing the nucleotides coding for the last 11 carboxy terminal aa in frame to the 5' end of a 5 aa truncated mCCL2 cDNA (FIG. 1A). The final fusokine GMME1 cDNA encodes for a single polypeptide chain (FIG. 1B). Computer-based analysis of the theoretical three-dimensional structure revealed that there is a 1 aa peptidic bridge consisting of asparagine that forms an intercytokine bridge and predicts a direct and stable interaction of the CCL2 domain of GMME1 with CCR2 (FIG. 1C). This asparagine can come from the original CCL2 protein, or it can be an asparagine peptide linker linked to the seventh amino acid of CCL2. Denaturing immunoblotting performed on the supernatant from HeLa cells transiently transfected to express GMME1 showed that the chimeric protein is efficiently secreted in the extracellular space and has a molecular weight of 50 KDa (FIG. 1D).

The human fusokine was created by cloning a cDNA of human GMCSF or hGMCSF in frame to the 5' end of a 5 aa truncated hCCL2 cDNA. The final fusokine hGMME1 cDNA encodes for a single polypeptide chain (FIG. 21A). Denaturing immunoblotting performed on the supernatant from HeLa cells transiently transfected to express hGMME1 showed that the chimeric protein is efficiently secreted in the extracellular space and has a molecular weight of 50 KDa (FIG. 21B).

Ligand-Induced Modulation of the CCR2BRET Signal

CCR2 has been previously demonstrated to homodimerize following its interaction with its agonist ligand CCL2. The incubation of CCR2-RLuc/CCR2-YFP expressing HEK cells with CCL2 induced a robust BRET increase, monitoring the conformational change induced in the CCR2 homodimer by its ligand. This effect is significantly attenuated upon prior digestion of CCL2 with MMP1 (mpCCL2), due to changes in the receptor that are different from those induced by full-length chemokine. Incubation with GMME1 induced a slight BRET decrease, significantly distinct from the signals induced by both full length CCL2 and mpCCL2, suggestive of distinct conformational effects of GMME1 upon CCR2 following binding. (FIG. 2A). Based on rCCL2 as positive control, it was found that increasing concentrations of GMME1 led to the opposite effect by decreasing the BRET ratio suggesting an inhibition of CCR2 homodimerization. Finally, the involvement of β-arrestin for GPCRs is important since it plays primordial roles in cellular desensitization to reciprocal ligands by recycling the receptor. To determine signalling downstream of CCR2 induced by GMME1, CCL2 and mpCCL2, respectively, the recruitment of β-arrestin 2 to CCR2 was investigated using BRET. As opposed to CCL2 which robustly recruits β-arrestin 2 to CCR2, GMME1 and MMP-processed mpCCL2 failed to produce such a response. A robust decrease of BRET signal following GMME1 stimulation was found suggesting the inhibition of β-arrestin recruitment to CCR2 whereas rCCL2 addition recruited it as anticipated (FIG. 2C).

Figure 3:
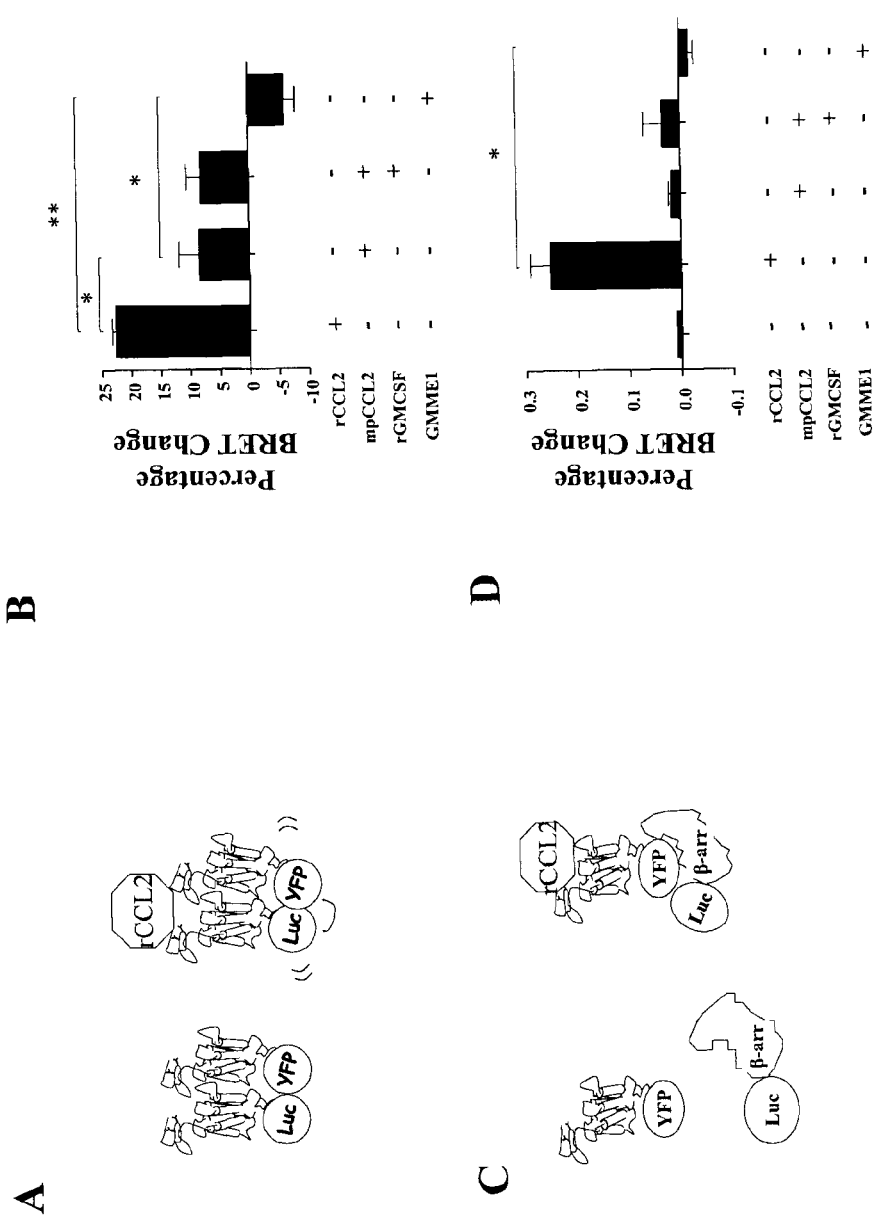
FIG. 3 shows the effect of GMME1 on normal CCR2 interactions. (A) Cartoon presentation of the BRET study analyzing CCR2 homodimerization. (B) GMME1 inhibits CCR2 homodimerization. CCR2 homodimerization was monitored in CCR2 expressing HEK293T-cells stimulated with increasing concentrations of rCCL2 or GMME1 in a BRET assay. (BC) Cartoon presentation of the BRET study analyzing Beta-arrestin recruitment to the receptor. (D) GMME1 blocks the recruitment of β-arrestin. BRET assay of GMME1 added to CCR2 expressing HEK293T-cells. Results are the average of three independent experiments performed in triplicate.

GMME1 induces Calcium Mobilisation and Apoptosis in CCR2-Expressing HEK293T-Cells The mechanism of action underlying GMME1 was analysed by looking for potential differences in the conformational rearrangements of homodimeric CCR2 following GMME1 and CCL2 binding to the receptor. HEK293T-cells were transfected with a plasmid encoding human CCR2 and its expression was confirmed by flow cytometry (FIG. 3A). To study the consequence of GMME1 distinct signalling on intracellular $Ca^{2+}$ mobilization, CCR2-expressing HEK-293T cells were further modified using the Premo™ calcium sensor reagent to allow the expression of cameleon, a calmodulin molecule fused to cyan fluorescent protein (CFP) and yellow fluorescent protein (YFP). If $Ca^{2+}$ molecules are mobilized, they will bind to cytoplasmic calmodulin and allow a change in the conformation of the entire protein leading to changes in the emitted wavelengths. Upon the addition of the different chemokine test conditions, $Ca^{2+}$ mobilization was observed as the BRET ratio increased following stimulation with rCCL2 or the combination of rGMCSF/rCCL2. Interestingly, the use of mpCCL2 or its combination with rGMCSF led to a negative BRET signal suggesting inhibition of basal $Ca^{2+}$ activity within the cell as opposed to GMME1, which induced robust $Ca^{2+}$ mobilization (FIG. 3B).

Apoptosis was determined by annexin-V/propidium iodine (PI) co-staining in flow cytometry. A substantial and significant proportion of GMME1 treated cells were dead (55% annexin-V/PI positive) compared to controls (1% for rGMCSF; 11% rCCL2, 17% mpCCL2; 12% for rGMCSF/rCCL2; and 14% rGMCSF/mpCCL2) (FIG. 3C, upper panel).

$Ca^{2+}$ influx is known to trigger cytochrome C release from mitochondria and pro-caspase 3 activation. To test whether GMME1 induces caspase 3 activation, CCR2-expressing HEK293T-cells were cultured with the same chemokine test conditions as previous for 48 hrs and whole cell lysates were probed for cleaved caspase 3. Only mpCCL2 induced a slight increase compared to the robust caspase 3 activation seen with GMME1 (FIG. 3C, lower panel).

Effects of GMME1 on Lymphomyeloid Cells

Figure 4:
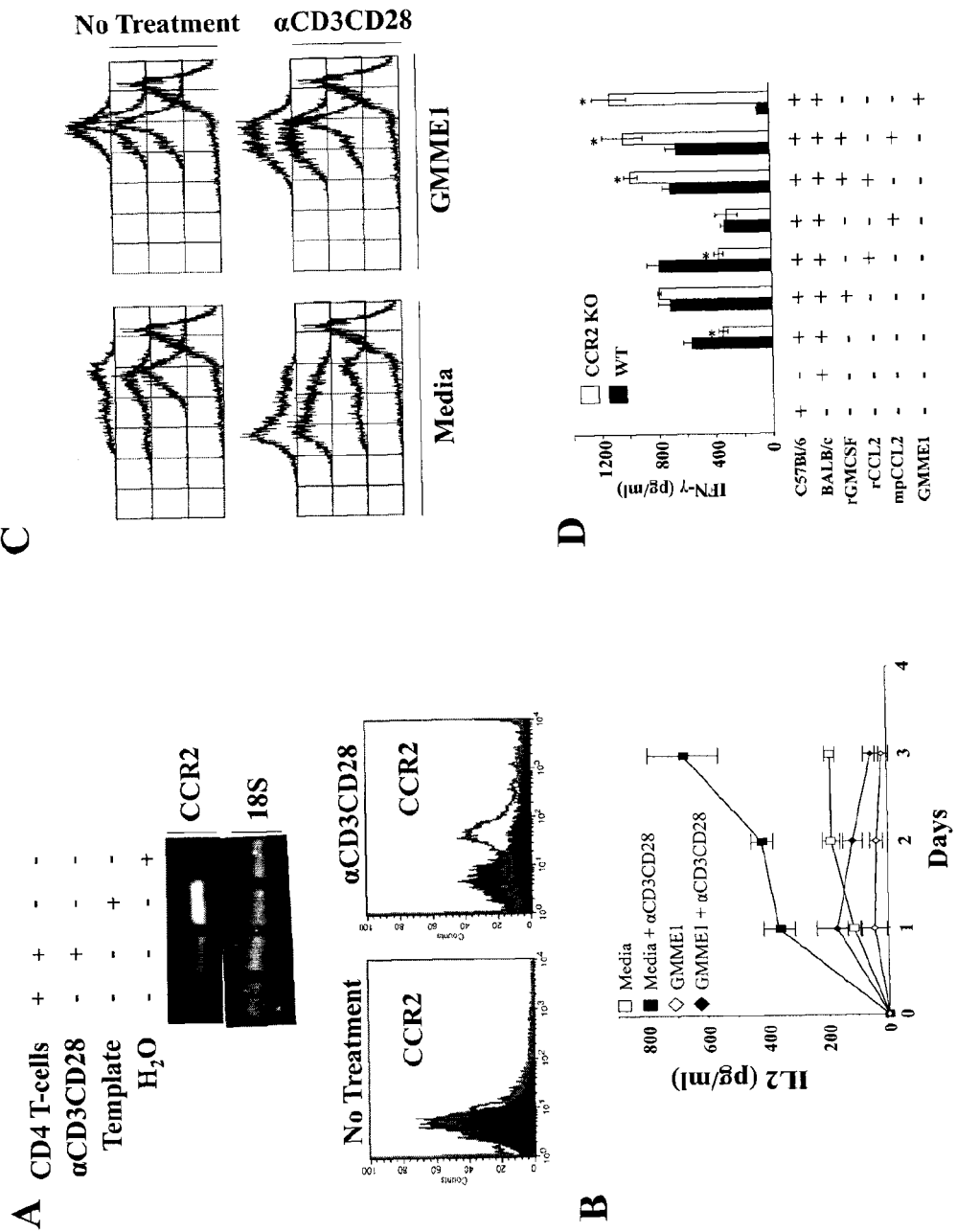
FIG. 4. Shows the effects of GMME1 on CCR2 expressing lymphoid cells. (A) CCR2 expression on activated T cells confirmed by qRT-PCR and flow cytometry. (B) GMME1 inhibits the proliferation of CD4 T-cells stimulated by CD3/CD28 beads and labelled with CFSE. (C) GMME1 prevents the production of IL-2 in CD4 T-cells stimulated by CD3/CD28 beads. (D) GMME1 does not affect $CCR2^{-/-}$ cells in a 1 way mixed lymphocyte reaction (MLR) whereas GMME1 prevents the production of IFN-gamma in a 2 way mixed lymphocyte reaction performed with wild type splenocytes CCR. IFN-gamma was tested by ELISA.

Following stimulation, activated T-cells are known to induce the expression of CCR2 de novo. To confirm this notion, naïve CD4 T-cells were purified and cultured with media alone or supplemented with beads containing anti-CD3/CD28 antibodies to induce CCR2 expression as shown by RT-PCR and flow cytometry analysis (FIG. 4A). To determine the functional impact of GMME1 on CD3/CD28 activated CD4 T-cells, CFSE-labelled CD4 lymphocytes were cultured in the presence of splenocyte conditioned media only or supplemented with GMME1. Interestingly, a strong proliferation of lymphocytes occurred under CD3/CD28 stimulation whereas the addition of GMME1 robustly inhibited it as seen with the CFSE peak profiles (FIG. 4B). Since IL-2 secretion accompanies lymphocyte activation, IL-2 levels in the supernatant of CFSE-labelled cells were analyzed and demonstrated to be strongly reduced following GMME1 treatment even after CD3/CD28 stimulation (FIG. 4C). To confirm these observations, the effect of GMME1 on physiologically activated lymphocytes was investigated. A mixed lymphocyte reaction (MLR) was performed with splenocytes derived from wild-type (WT) C57BL/6 mice or $CCR2^{-/-}$ C57BL/6 mice as responders and paraformaldehyde fixed BALB/c splenocytes as stimulators. The up-regulation of interferon (IFN)-γ production was measured as a surrogate marker of allo-activation of the C57BL/6 responders. Wild type cells produced significantly less IFN-γ production when exposed to GMME1, whereas $CCR2^{-/-}$ responder lymphocytes were unaffected by GMME1 treatment (FIG. 4D).

Figure 5:
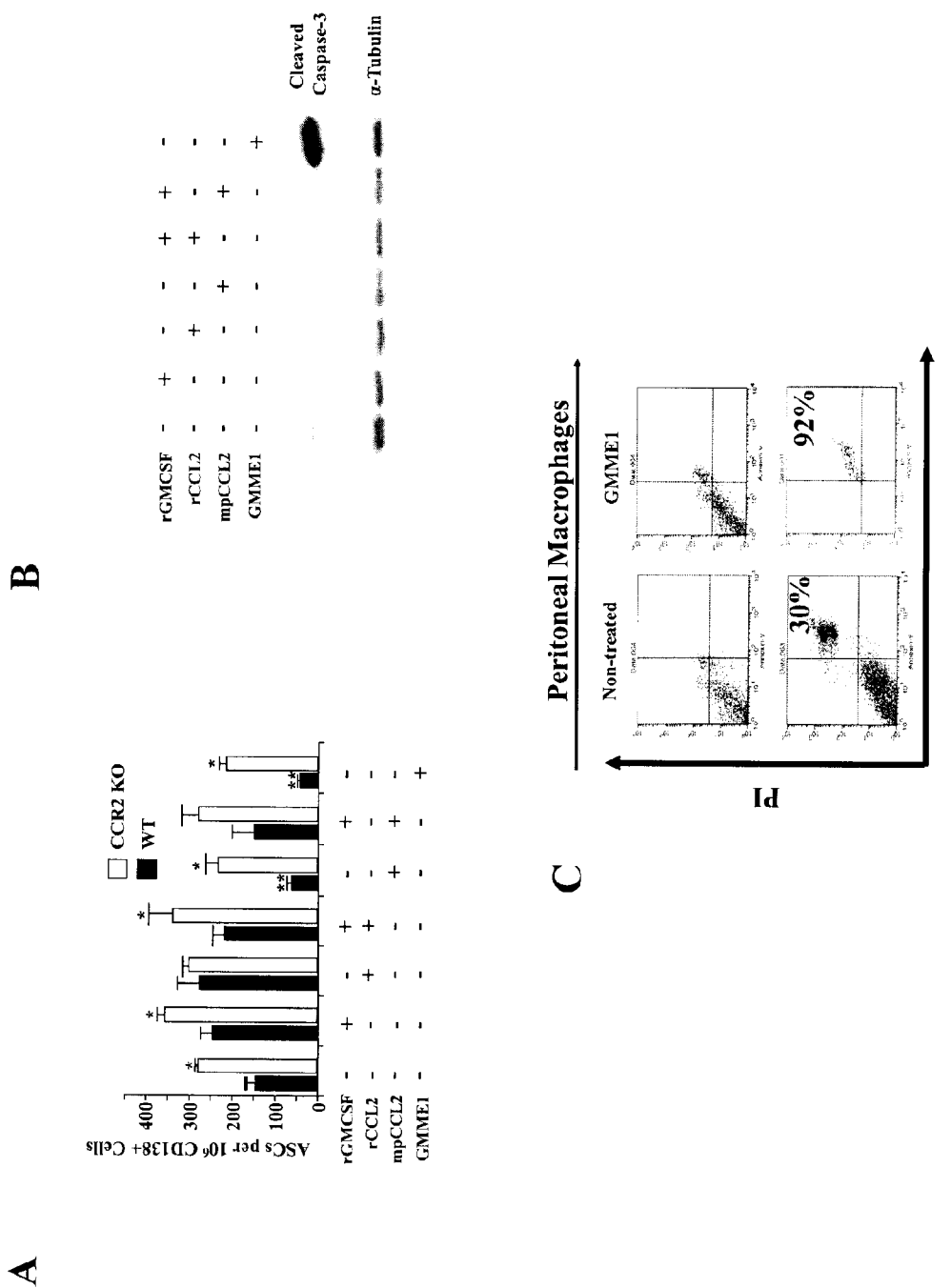
FIG. 5 shows effects of GMME1 on macrophages and B cells. (A) GMME1 and mpCCL2 decrease antibody production in antibody secreting cells (ASC). Sorted $CD138^+$ plasma cells cultured with different chemokines were assessed for antibody production by ELISPOT assay (n=3 per group with a P<0.05). Results are shown as mean±S.E.D. (B-C) GMME1 induces apoptosis in macrophages as demonstrated in (B) Caspase-3 levels assessed by western-blotting in lysates of peritoneal C57BL/6 macrophages cultured for 24 hrs in the presence of different chemokines. (C) Apoptosis confirmed for media or GMME1 treatment by PI and Annexin-V co-staining.

Along with the same idea, an ELISPOT was performed to study the effect of GMME1 on plasma cells. Even though a strong inhibition of antibody secretion was noticed using either mpCCL2 or GMME1, no major significance was observed between the two groups. Following the immunization of WT or $CCR2^{-/-}$ C57Bl/6 mice with recombinant ovalbumin (rOVA) to induce an OVA-specific humoral response, splenocytes were cultured in the presence of GMME1 before performing an OVA-specific ELISPOT assay. A robust inhibition of antibody production was observed after treatment with both mpCCL2 (rCCL2+hMMP1) and GMME1 on WT antibody-secreting cells (ASCs) only suggesting that the fusokine is as potent as the antagonistic form of CCL2 (mpCCL2) in suppressing plasma cells expressing CCR2 (FIG. 5A). In addition to B and T lymphocytes, macrophages are known to heavily express CCR2, therefore it is conceivable to investigate their response to GMME1. Peritoneal macrophages harvested from C57BL/6 mice and exposed to GMME1 died by apoptosis 24 hrs later as demonstrated by the strong activation of caspase-3 (FIG. 5B). These observations were confirmed by flow cytometry as shown by Annexin-V/PI co-staining; 92% with GMME1 as opposed to 30% with media (FIG. 5C).

GMME1 Allows Xenotransplantation of HeLa Cells in Immunocompetent Mice

Figure 6:
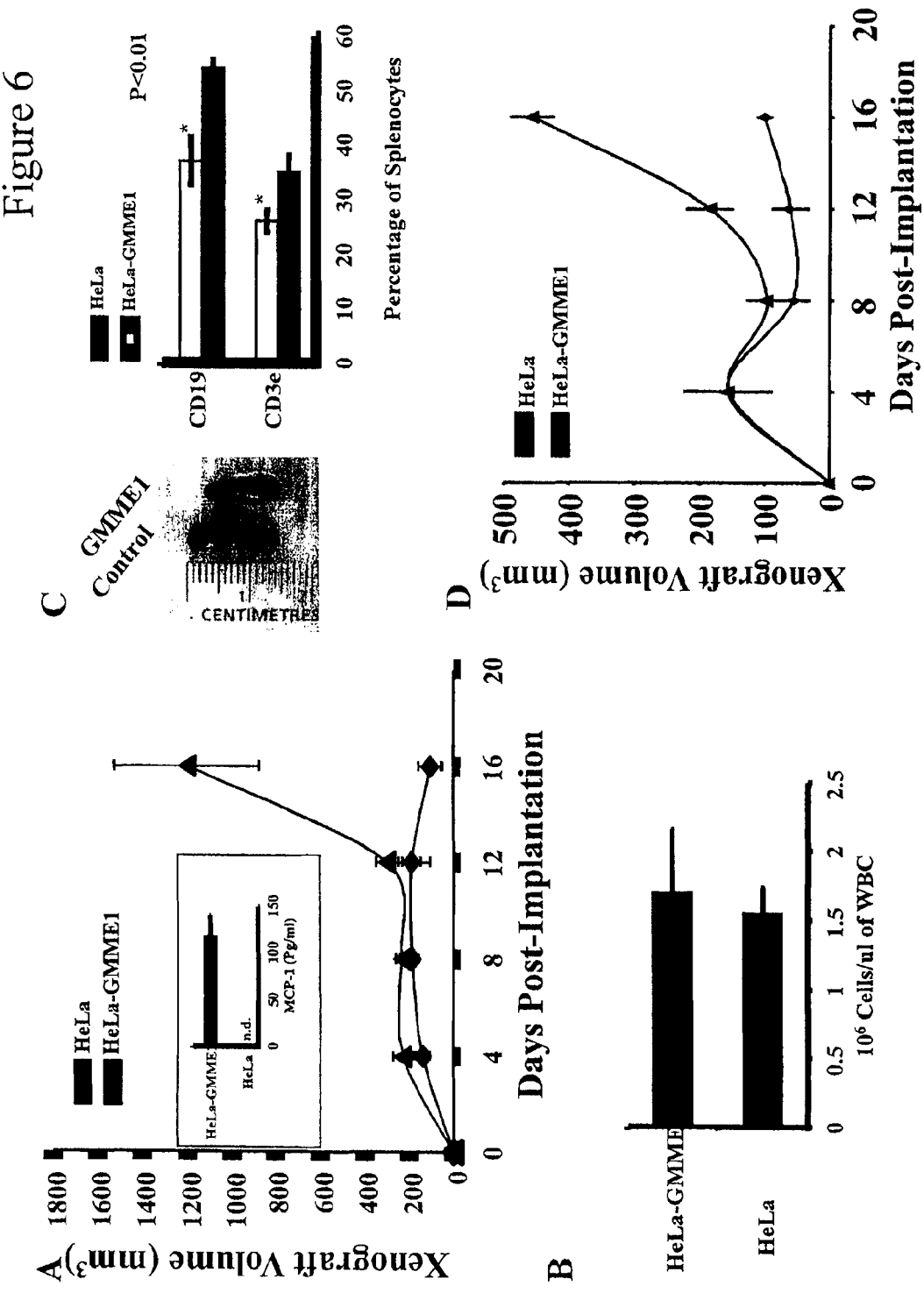
FIG. 6 shows GMME1 effect on HeLa xenotransplantation (A). Immunocompetent C57BI/6 mice (n=5) were grafted with $10^6$ live HeLa-null (♦) or HeLa GMME1/transfected HeLa cells (▲) subcutaneously and implant volumes were monitored. CCL2 ELISA was performed on serum collected at day 16 from both mice groups. (B) Circulating White Blood Cell (WBC) Count. Before the mice were sacrificed, 20 μl of blood was collected to perform a general WBC count. (C) Spleen Analysis. A representative spleen from both groups was measured and flow cytometry analysis was performed on $CD3e^+$ and $CD19^+$ cells (P<0.01 between HeLa-null and HeLa-GMME1). (D) Xenograft graft analysis over time in immunocompetent mice. Results are shown as mean tumour volume±S.E.D.

The limits of GMME1-mediated tolerance were tested in the context of xenotransplantation using the human HeLa cell line stably transfected to secrete the fusokine ($10^6$ HeLa-null or GMME1 cells were injected subcutaneously in C57Bl/6 mice). GMME1-expressing xenografts were accepted in all mice whereas null HeLa cells were rejected by day 16 post-transplantation in the control group (FIG. 6A). No major differences were found at the level of circulating WBC (FIG. 6B) as opposed to the spleen, where a reduction in both in size and percentages of T and B-lymphocytes was observed (FIG. 6C). In summary, GMME1 protects the xenograft through lymphocyte-depletion in vivo.

Use of Mesenchymal Stromal Cells for Delivery of Conjugate Protein

Figure 7:
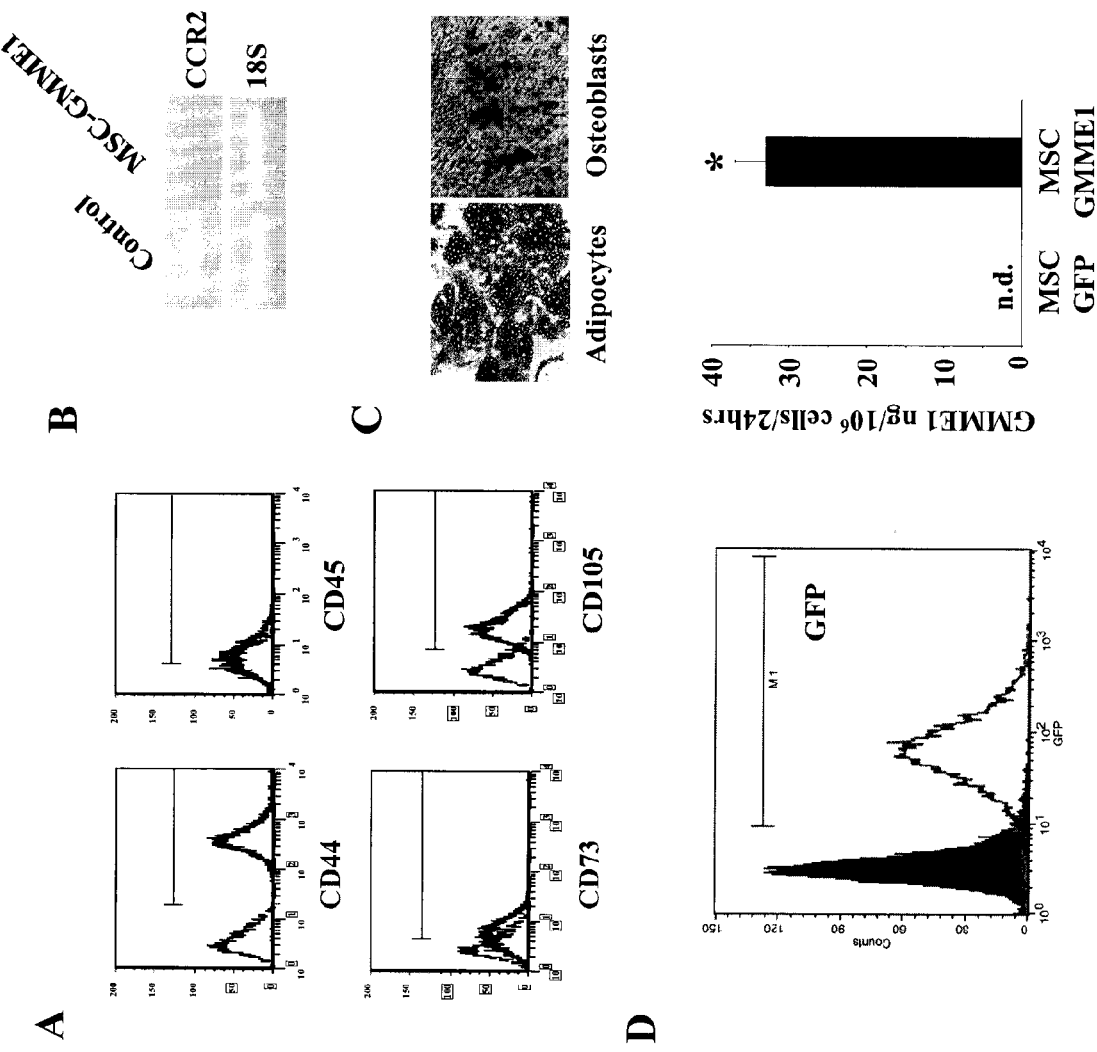
FIG. 7 shows phenotype analysis. (A) The phenotype of expanded C57BL/6 MSCs was analyzed by flow cytometry for various cell surface markers. (B) An RT-PCR analysis demonstrates that MSC do not express CCR2. (C) MSC culture under adipogenic or osteogenic conditions lead to their differentiation. Photographs were taken under light microscopy using a Contax167MT camera (Kyocera) with a 400 ISO film attached to an Axiovert25 Zeiss microscope (Carl Zeiss). (D) Following the retroviral transduction of MSC, the GFP expression levels was monitored by flow cytometry with GMME1 secretion levels of 33 $ng/10^6$ ng/24 hrs as detected by ELISA (P<0.05; n=3/group).

Several studies have shown that Mesenchymal Stromal Cells (MSCs) could be exploited for the delivery of proteins with pharmacological properties (Rafei et al. 2009a; Eliopoulos et al. 2004; Kucic et al. 2008). Gene-engineered MSCs can deliver therapeutic proteins as part of a neo-organoid composed of human compatible FDA-approved collagen matrix (Eliopoulos et al. 2004). The advantage of this delivery method is that it allows for stable transgene expression over a long period of time and permits removal of the implant when desired. Using MSCs isolated from CCL2$^{-/-}$ C57Bl/6 mice, a polyclonal population secreting GMME1 was gene-engineered without affecting the phenotype of these cells. As such, MSCs expressing GMME1 were still CD44, 73 and 105 positive with no detectable expression of CD45 (FIG. 7A) or CCR2 (FIG. 7B) while retaining their capacity to differentiate into adipocytes or osteoblasts (FIG. 7C). Supernatant analysis of these cells revealed a GMME1 secretion level of 30 ng per 1 million cells every 24 hrs (FIG. 7D).

GMME1 is Tumoricidal for EG7

Figure 8:
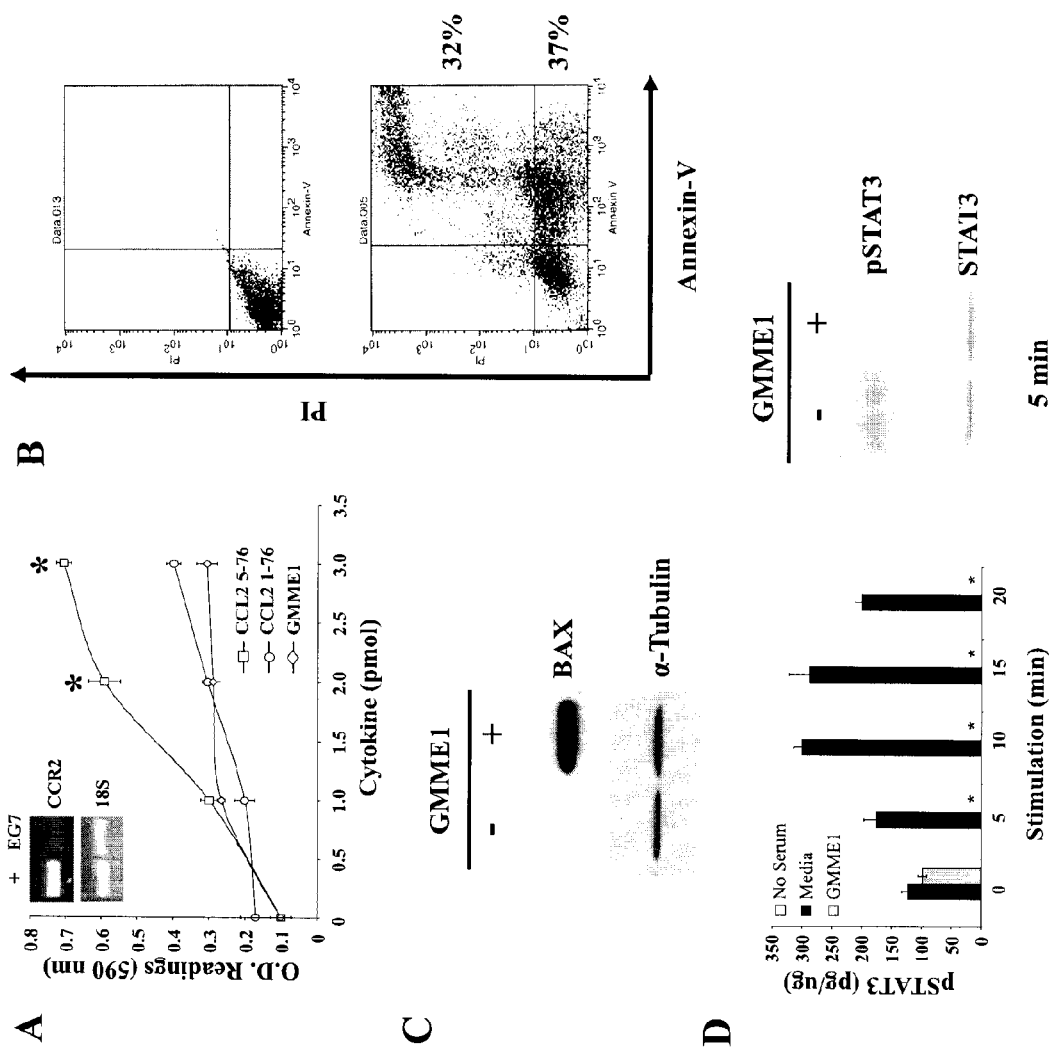
FIG. 8 shows pharmacological properties of GMME1 on EG7 tumor cells. (A) Following the confirmation that EG7 cells express CCR2 by RT-PCR, $10^5$ EG7 cells/well were cultured with increasing amounts of CCL2 5-76, CCL2 1-76 or GMME1 and the proliferative response measured by MTT. mpCCL2, and to a lesser extent, CCL2 1-76 were capable of inducing the proliferation of EG7 cells as opposed to GMME1 (P<0.05; n=6/group). (B) Following the addition of 1.5 pmol of GMME1 on EG7 cells for 48 hrs, a PI/Annexin-V co-staining demonstrates that GMME1 leads to apoptosis induction (32% dead cells). (C) EG7 cells cultured with GMME1 for 48 hrs induce de novo expression of the pro-apoptotic BAX protein. (D) Following the stimulation of EG7 cells for different time points, cell lysate was analyzed by a pSTAT3 ELISA (P<0.05; n=6/group). The experiment was repeated using the 5 min time point then lysate was probed by WB. Total STAT3 was used as loading control.

Since GMME1 exerts powerful pro-apoptotic effects on cells expressing CCR2 both in vitro and in vivo, the effect of the fusokine directly on the mouse lymphoma cell line EG7 was investigated. No proliferative response was observed upon GMME1 treatment as is seen with the use of CCL2 1-76 completely opposite to CCL2 5-76 which seems to work as a mitogen (FIG. 8A). A hallmark of GMME1 is its capacity to induce cell death in CCR2 positive cells (Rafei et al. 2009a) and thus, the observed suppression of EG7 in vitro proliferation was attributed to apoptosis induction. In a test for this hypothesis, PI/Annexin-V co-staining revealed that 30% of EG7 cells died following a 48-hour treatment with GMME1 (FIG. 8B) and was associated with de novo expression of the pro-apoptotic BAX protein (FIG. 8C). CCR2 is known to induce STAT3 phosphorylation; a signalling molecule heavily involved in survival, proliferation, angiogenesis as well as immunosuppression (Mellado et al. 2001; Xie et al. 2006). Thus, GMME1 was tested for its ability to inhibit STAT3 activation. Complete blocking was obtained within 5 min following treatment, an observation that was confirmed by Western Blot (FIG. 8D).

Figure 9:
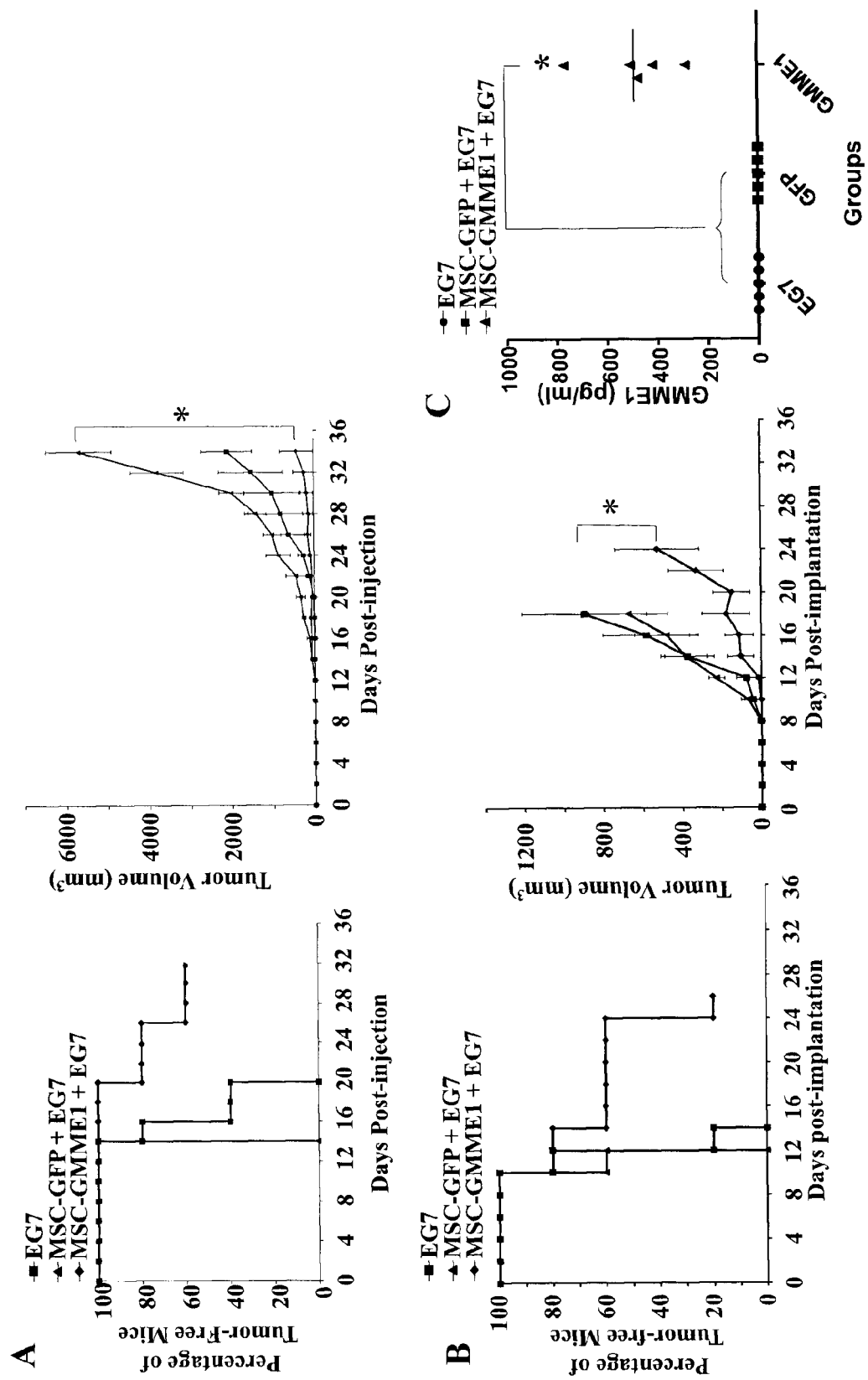
FIG. 9 shows anti-tumor effect of GMME1-expressing $CCL2^{-/-}$ MSCs. (A) The subcutaneous injection of immunocompetent C57BI/6 mice (n=5/group) with $10^6$ EG7 cells alone or in combination with $2\times10^6$ MSC-GFP leads to the development of large tumors in all mice. The admix of GMME1-expressing MSC with EG7 tumor cells led to a significant delay in EG7 growth with 60% of mice that remained tumor-free for over a month. (B) To assess the growth of EG7 cells in mice implanted with a neo-organoid expressing GFP vs the GMME1 fusokine, immunocompetent C57BI/6 mice (n=5/group) were injected on one flank with contigen containing $2\times10^6$ MSC engineered to express GFP or GMME1 followed by $10^6$ EG7 cells on the opposite flank. Tumor volume and appearance was assessed every 48 hrs. A significant delay in tumor growth was noticed. (C) Three weeks post-contigen implantation, mice were bled and the sera tested using the CCL2 ELISA for GMME1. All mice implanted with MSC expressing the fusokine GMME1 showed detectable levels if the fusokine systemically as opposed to control MSC-GFP or mice implanted with EG7 cells only.

The anti-tumor efficacy of GMME1 in vivo was assessed by admixing 2×10$^6$ MSC-GFP or GMME1 with 10$^6$ EG7 lymphoma cells which were subcutaneously implanted in immunocompetent C57Bl/6 mice. All mice implanted with MSC-GFP and EG7 developed tumors by day 14 (FIG. 9A upper left panel) with larger volumes when compared to EG7 tumor cells alone (FIG. 9A upper right panel). In contrast, when GMME1-expressing MSCs were transplanted with EG7 cells, a significant delay in tumor growth was observed with 60% tumor-free mice after 32 days (FIG. 9A). A more clinically relevant approach however, consists of delivering GMME1 systemically rather than peritumorally. Therefore, immunocompetent C57Bl/6 mice were injected subcutaneously using human compatible FDA-approved collagen containing GMME1-secreting MSCs on one flank of the animal and the tumor cells on the opposite flank. A substantial anti-tumor effect was obtained with GMME1 since 60% of mice were tumor-free with a significant tumor growth delay up to 3 weeks post-implantation of the neo-organoid (FIG. 9B). This therapeutic effect correlates with the systemic detection of GMME1 at this time point (FIG. 9C). Such observation suggests that a sustained production of GMME1 is achievable directly in vivo, and could be readily applied in the setting of advanced metastatic tumors expressing CCR2. Mice treated with GMME1 did not display evident off-target toxicity as ascertained by normal weight and behaviour.

GMME1 is Tumoricidal for U266

Figure 10:
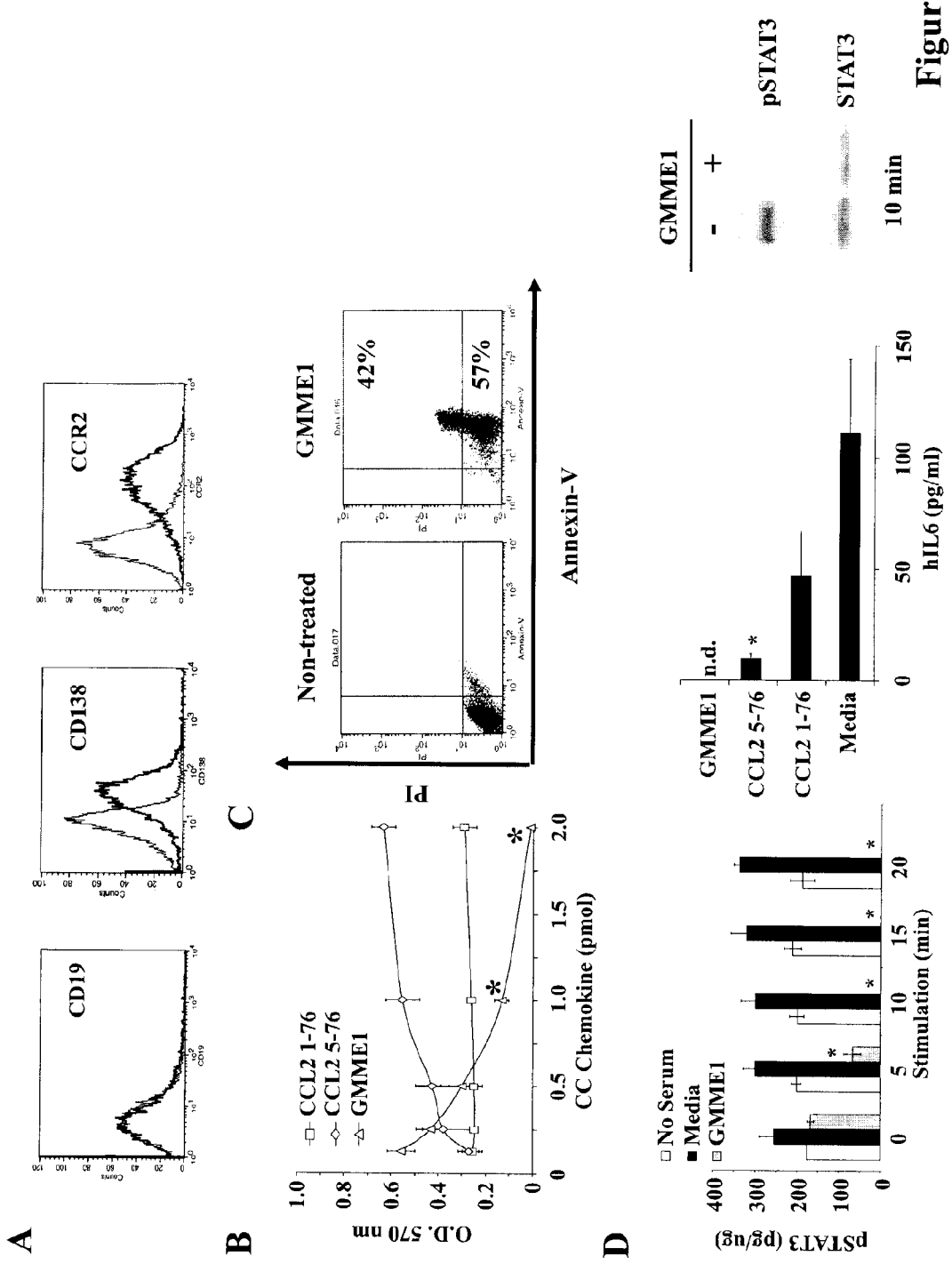
FIG. 10 shows pharmacological properties of GMME1 on human 0266 tumor cells. (A) U266 cells were analyzed by flow cytometry and were negative for the expression of CD19 while CD138 and CCR2 were detected. (B) $10^5$ U266 were cultured with increasing amounts of CCL2 5-76, CCL2 1-76 or GMME1 and the proliferative response measured by MTT. CCL2 5-76 was capable of inducing U266 proliferation whereas GMME1 completely suppressed the proliferative response (P<0.05; n=6/group). (C) Using 1.5 pmol of GMME1 on U266 cells for 48 hrs, a PI/Annexin-V co-staining demonstrates that GMME1 leads to apoptosis (42% cell death). (D) A similar set-up was used for the assessment of STAT3 activation on U266. Following the stimulation of U266 cells using different time points, cell lysate was analyzed by a pSTAT3 ELISA. Since STAT3 is inhibited as of 10 min following GMME1 addition on U266 cells, the experiment was repeated at this time point then the lysate was probed by WB. Total STAT3 was used as loading control. To further confirm the inhibitory effect of GMME1 on these cells, the U266 conditioned-media was collected following 48 hrs post-treatment with the different test conditions and analyzed using a hIL6 ELISA. No detectable levels of hIL6 could be observed in the GMME1 group as opposed to the remaining test conditions (P<0.05; n=6/group).

Mouse CCL2 is biologically active on human CCR2-expressing cells (Luini et al. 1994). As such, the pharmacological properties of mouse GMME1 was further assessed on the human multiple myeloma cell line U266; a CD19$^{-/-}$ human cell line known to express the plasma cell marker CD138 and CCR2 (FIG. 10A). Recombinant 1-76 CCL2 had no effect on U266 proliferation whereas increasing mpCCL2 concentrations acted like a mitogen (FIG. 10B). However, GMME1 induced cell death of U266 starting at 1 pmol with no metabolically active cells detected once GMME1 reached a concentration of 2 pmol. Growth and proliferation of U266 depend on the autocrine stimulation by hIL6, which leads to pSTAT3 (Luini et al. 1994). Therefore, supernatants of U266 cultured under the above conditions were screened for hIL6 by ELISA. mpCCL2 or 5-76 CCL2 induces proliferation, whereas no detectable hIL6 was found with GMME1. As confirmation of this observation, PI/Annexin-V analysis following 48 hrs GMME1 treatment revealed about 40% cell death by apoptosis (FIG. 10C). Since it has been previously shown that GMME1 inhibits STAT3 phosphorylation in EG7 lymphoma cells, the level of STAT3 activation was assessed first by ELISA at different time points and documented a complete loss of activation following 10 min of GMME1 treatment, an observation that was confirmed by immunoblot (FIG. 10D left panels). These data correlate with the loss of hIL6 secretion by U266 (FIG. 10D right panel) due to cell death induced by GMME1.

The use of innovative chimeric CC-ligand polypeptides could serve as a prototype strategy seeking to selectively deplete cancers whose proliferation and survival depends upon CCR-driven signalling.

Biochemical Effects of GMME1 on Pathogenic Lymphoid Cells

Figure 11:
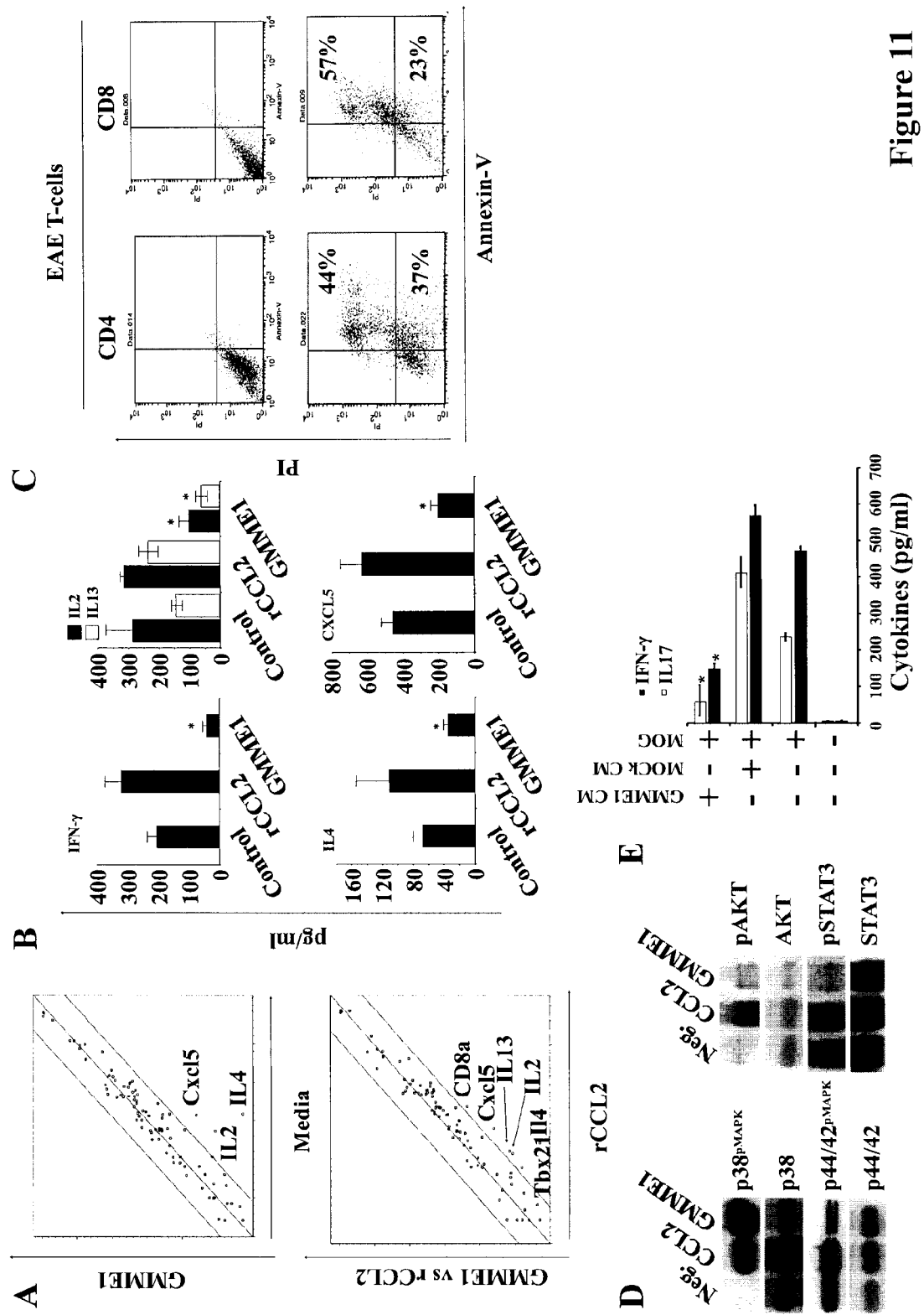
FIG. 11 shows the biochemical effects of GMME1 in experimental autoimmune encephalitis (EAE). (A) Modulation of the expression of genes encoding pro-inflammatory proteins tested by qRT-PCR and confirmed by ELISA (B). (C) Induction of apoptosis in EAE CD4 and CD8 T cells by GMME1 demonstrated by PI/Annexin co-staining. (D) Asymmetrical phosphorylation profiles after GMME1 treatment, increased activation of p38 reduced activation of p44/42 and inhibition of AKT phosphorylation. (E) Reduction of IFN-γ and IL-17 expression in EAE CD4 T cells by GMME1.

The molecular mechanism of the effect of GMME1 on lymphocytes involved in the pathogenesis of EAE was subsequently analysed. Splenocytes collected from EAE mice were stimulated in vitro with MOG alone, in the presence of rCCL2 or a combination of rCCL2 and GMME1 to examine the effect of the fusokine under competitive conditions. A quantitative RT-PCR (qRT-PCR) array was then performed on isolated RNA to identify modulated inflammatory genes. As shown in FIG. 11A, GMME1 led to the downregulation of interleukin (IL)$_2$, IL4, IL13, CXCL5 as well as the transcription factor T-box 21 involved in IFN-γ induction even in the presence of rCCL2 in a 1:1 molar ratio to GMME1. All identified factors were then confirmed by ELISA (FIG. 11B). Interestingly, following CD4 and CD8 T-cells purification from EAE mice and GMME1 treatment for 48 hrs, almost 80% of both cell populations were seen undergoing apoptosis (FIG. 11C). To determine GMME1's effect on molecular pathways in purified CD4 T-cells the latter were stimulated for 5 min with GMME1 or rCCL2. An asymmetrical activation of the MAPK pathway was demonstrated after GMME1 treatment which induces hyper-activation of p38 while leading to the inhibition of p44/42 phosphorylation (FIG. 11D). Furthermore, GMME1 was capable of completely blocking both AKT and STAT3 activation as opposed to rCCL2. This clearly shows that GMME1 antagonizes the AKT and JAK-STAT pathways (FIG. 11D). The significance of CD4 lymphocytes in the induction of EAE pathology based on the established mechanisms was further analysed in purified EAE CD4 T-cells cultured in the presence of fixed syngeneic peritoneal macrophages presenting MOG$_{35-55}$ under different test conditions. As such, macrophages act as stimulators without the capacity of secreting soluble factors that might interfere with the assay. As expected, CCL2$^{-/-}$ MSC conditioned medium (CM) significantly induced both IL17 and IFN-γ, pro-inflammatory cytokines implicated in promoting EAE. However, GMME1 significantly inhibited their secretion from responder CD4 T-cells and thus interferes with the induction of EAE pathology (FIG. 11E).

Delivery of GMME1 to EAE Mice Ameliorates Pathology

Figure 12:
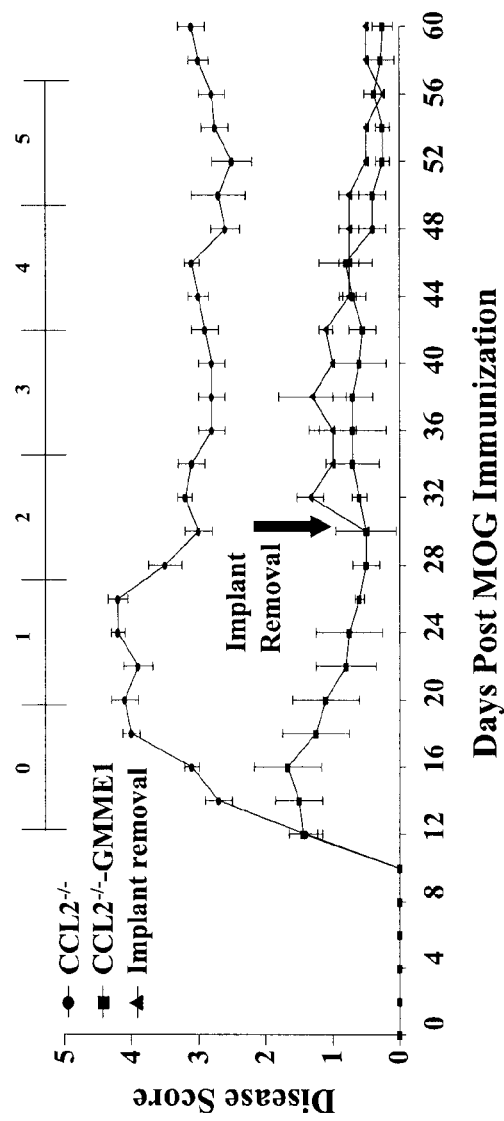
FIG. 12 shows the course of EAE with and without GMME1. GMME1 gene-engineered mesenchymal stromal cells (MSCs) derived from $CCL2^{-/-}$ mice, embedded in biomatrix, implanted subcutaneously, and used as an in vivo continuous delivery platform led to a progressive and stable recovery of EAE disease score.

Gene-engineered Mesenchymal Stromal Cells (MSCs) were used as an in vivo delivery platform. MSCs were embedded in biomatrix and implanted subcutaneously form a neo-organoid—in essence a synthetic ectopic endocrine tissue—which allows for long term delivery of proteins such as GMME1 as described above. Since MSCs are known to secrete CCL2 and its cleaved variant, they were derived from $CCL2^{-/-}$ mice as a cell-based platform to deliver GMME1 in vivo, in order to avoid any bias arising from contemporaneous CCL2 secretion. For the evaluation of the in vivo efficacy of GMME1 under pathological conditions, C57Bl/6 mice with pre-established EAE received a neo-organoid contigen implant containing $CCL2^{-/-}$ MSCs gene-engineered to secrete GMME1. The continual delivery of the fusokine led to a progressive and stable recovery of EAE disease score up to 2 months with no apparent relapse (FIG. 12). One advantage of using neo-organoid implants is the possibility to surgically remove the implant with full reversal of in vivo protein delivery as previously shown. Even the removal of the implant containing GMME1 expressing MSC did not lead to remission.

In Vitro Analyses of the Effect of GMME1 in EAE Pathology

Figure 13:
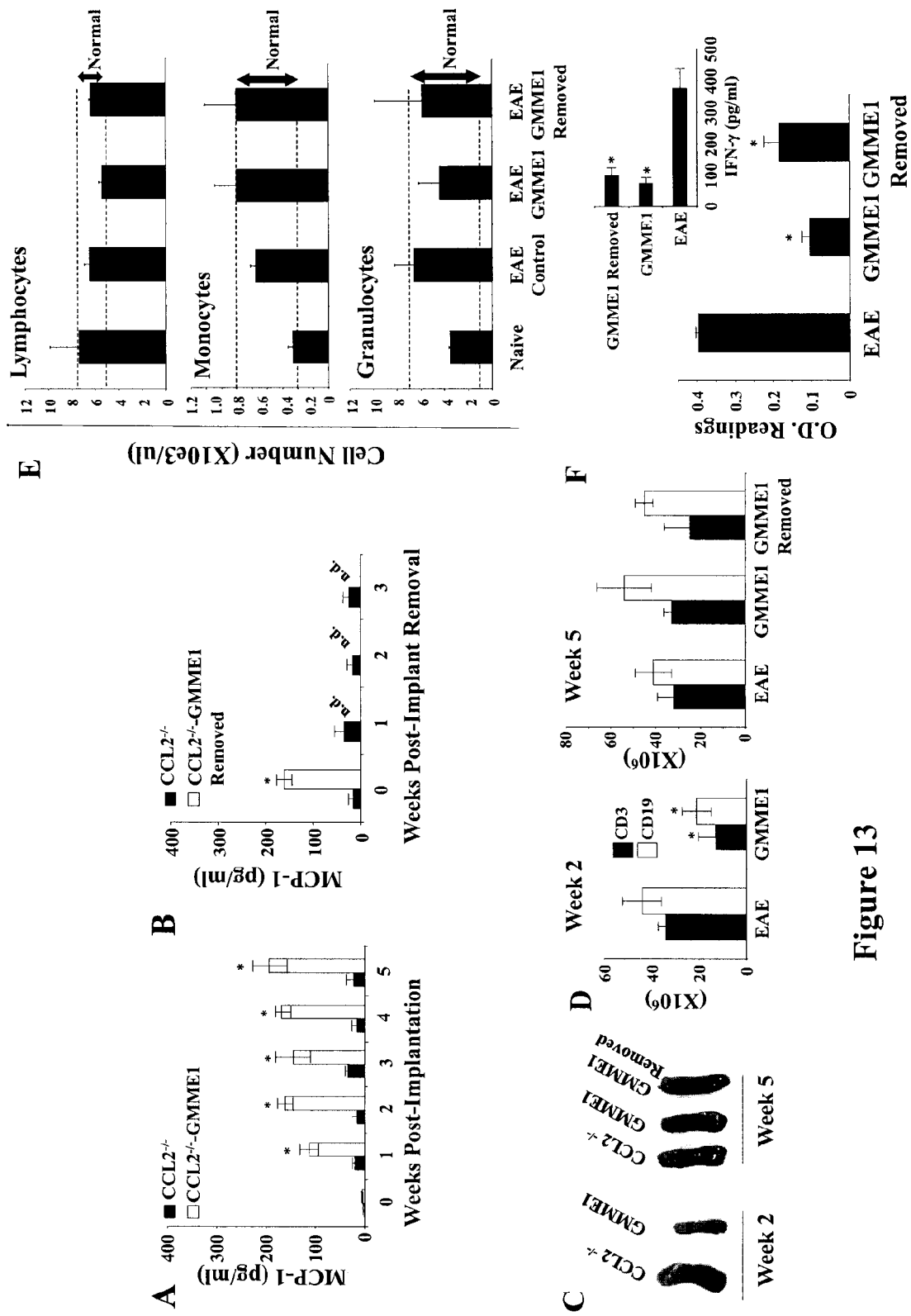
FIG. 13 shows in vitro analyses accompanying the EAE disease progression in FIG. 10. (A) Detection of CCL2 in $CCL2^{-/-}$ mice with and without GMME1 implants during weeks after implantation. (B) Detection of CCL2 in $CCL2^{-/-}$ mice with and without GMME1 implants during weeks after implant removal. (C) Splenic atrophy during inflammation (week 2) resolved after 5 weeks due to reduction of CD3 positive T cells and CD19 positive B cells and their recovery in CCL2$^{-/-}$ mice with or without GMME1 implants (D). (E) No systemic depletion of peripheral blood leukocyte count in CCL2$^{-/-}$ EAE mice with or without or after extraction of GMME1 implants at week 5. (F) In vitro restimulation of splenocytes derived from CCL2$^{-/-}$ EAE with or without GMME1 implants.

ELISA analyses performed on mice sera at different time points before and after implant removal confirmed that GMME1 levels were present before (FIG. 13A) but absent after (FIG. 13B) removal of the implant. GMME1 levels were detected starting in the first week post-implantation and persisted up to the fifth week in mice bearing the contigen implant (FIG. 13A), whereas no detectable levels of the fusokine were observed 1 week post-removal (FIG. 13B). Despite the removal of the GMME1 implants mice remained in EAE remission for the residual observation period of 9 weeks. Spleens from control or GMME1 implanted mice were analyzed at weeks 2 and 5. Splenic atrophy was observed in the GMME1 group early during inflammation (week 2) but resolved to full size at week 5 (FIG. 13C). Furthermore, the spleens of mice whose GMME1 implants were removed looked similar to those of the remaining control groups (FIG. 13C). The flow cytometric analysis of the atrophied spleens of GMME1-treated mice demonstrated a lympho-depletion of $CD3^+$ and $CD19^+$ cells occurring at week 2 with normal levels at week 5 once the pathology was resolved (FIG. 13D). However, peripheral blood leukocyte counts over the same period were not significantly affected (FIG. 13E). In vitro re-stimulation of splenocytes derived from treated or control EAE mice demonstrate a weak proliferation in the GMME1 or GMME1 removed implant group with a robust decrease in levels of IFN-γ (FIG. 13F).

Hematological Analysis of EAE Mice Treated with GMME1

Figure 14:
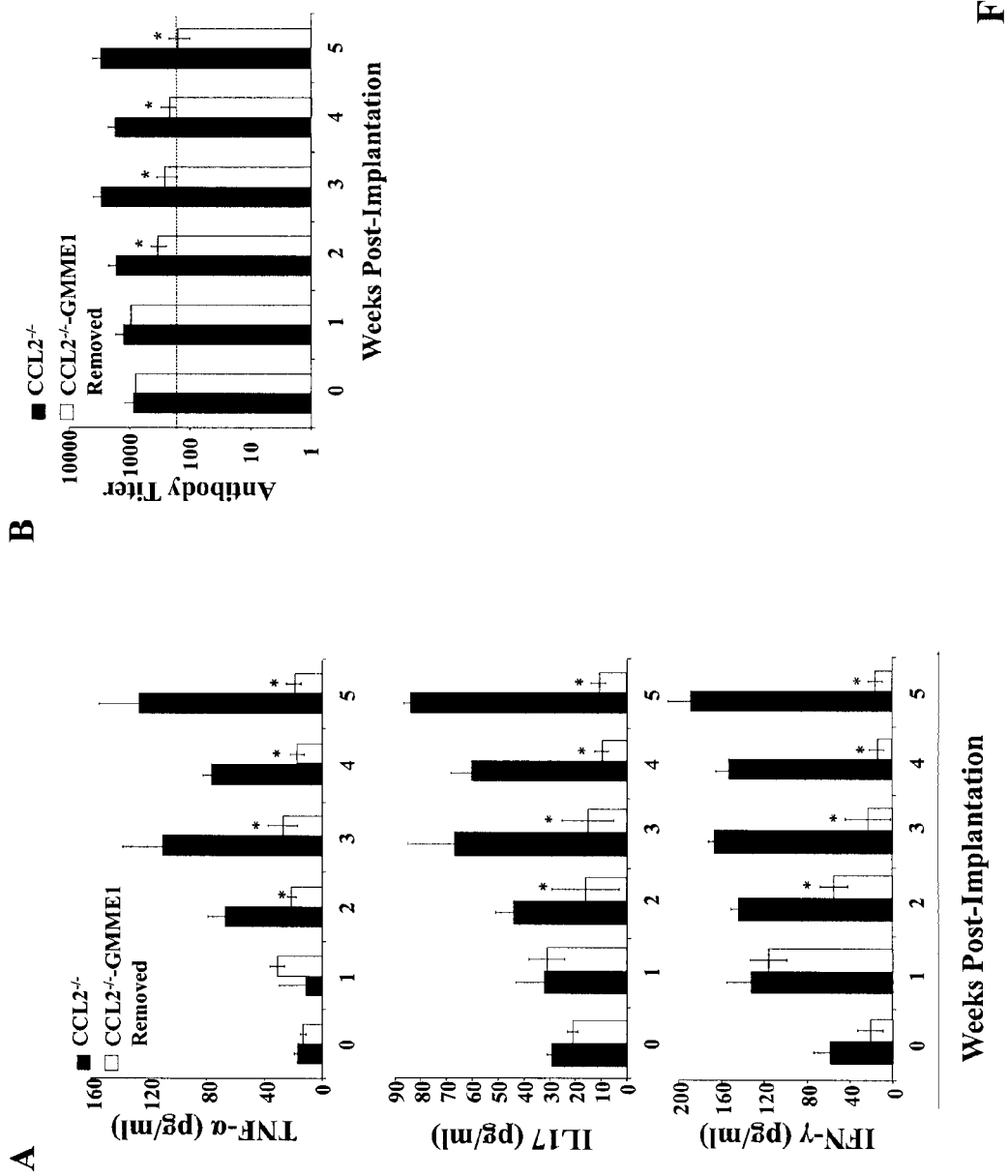
FIG. 14 shows hematological analysis of EAE mice treated with GMME1. (A) Reduced serum levels of proinflammatory cytokines TNF-α, IFN-γ, and IL-17 after exposure to GMME1. (B) Reduced serum levels of MOG specific antibodies.

Plasma cytokine analysis show that the presence of the fusokine correlates well with the decrease in levels of pro-inflammatory cytokines such as TNF-α, IFN-γ, and IL17 in circulation (FIG. 14A). A noticeable improvement was also obtained at the humoral level since MOG antibody titer decreased significantly in GMME1-treated mice (FIG. 14B).

Pathological Analysis of EAE Mice Treated with GMME1

Figure 15:
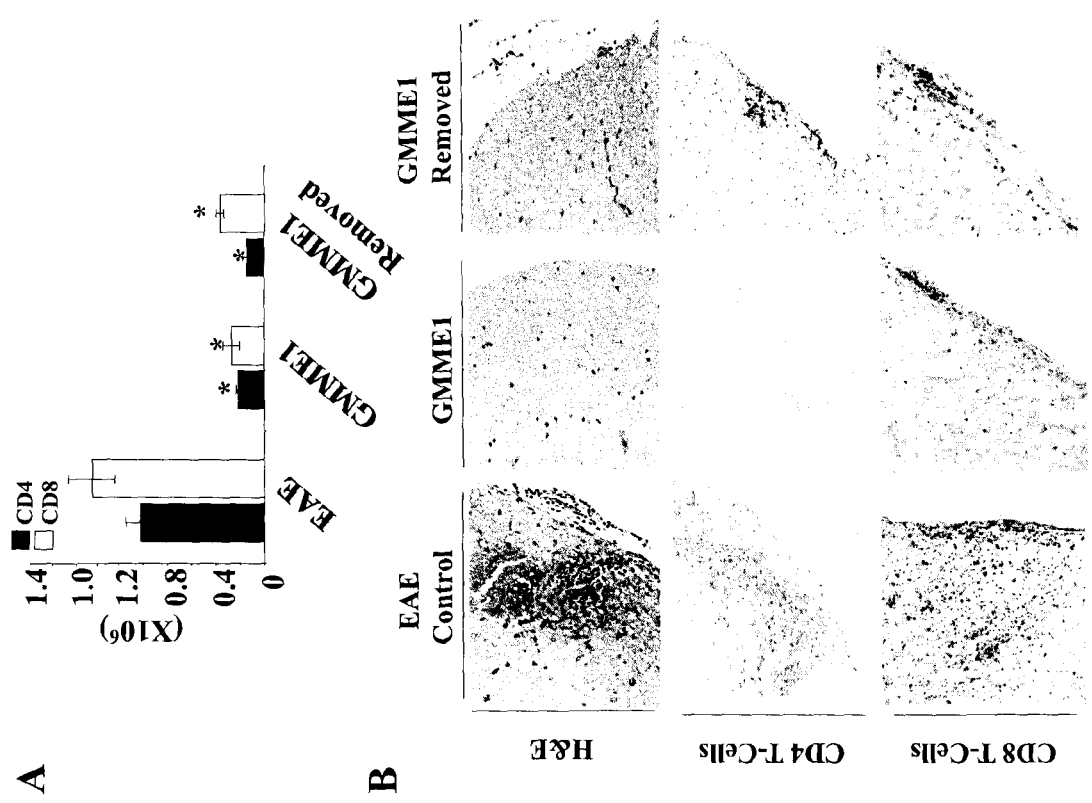
FIG. 15 shows the pathological analysis of EAE mice treated with GMME1. (A) CD4/CD8 T cells counted by flow cytometry in spinal cord of EAE mice with and without GMME1 transplants. (B) Reduction of CD4/CD8 T cell infiltrates in EAE mice before and after GMME1 implant removal.

One of the most important hallmarks of EAE is spinal cord infiltration by MOG-specific CD4 T-cells. Once they have crossed the blood-brain barrier, CD4 T-cells get reactivated by microglia cells presenting the MOG peptide leading to the induction of pro-inflammatory cytokines and chemokines, which in turn will amplify inflammation, neuronal damage and recruitment of further effector immune cells. Analysis of absolute cell numbers of CD4 and CD8 T-cells in the spinal cord demonstrate a large infiltration of immune cells in the EAE control group as opposed to the two groups that received GMME1 implants which was later removed in one of these groups (FIG. 15A). The same outcome was obtained by H&E staining of spinal cord samples or through immunohistology identifying CD4 and CD8 lymphocytes (FIG. 15B) demonstrating the potency of GMME1 in robustly blocking inflammatory cell migration to the CNS most likely due to their cell death in the periphery.

Biochemical Effects of GMME1 on RA-Derived CD4 T-Cells

Figure 16:
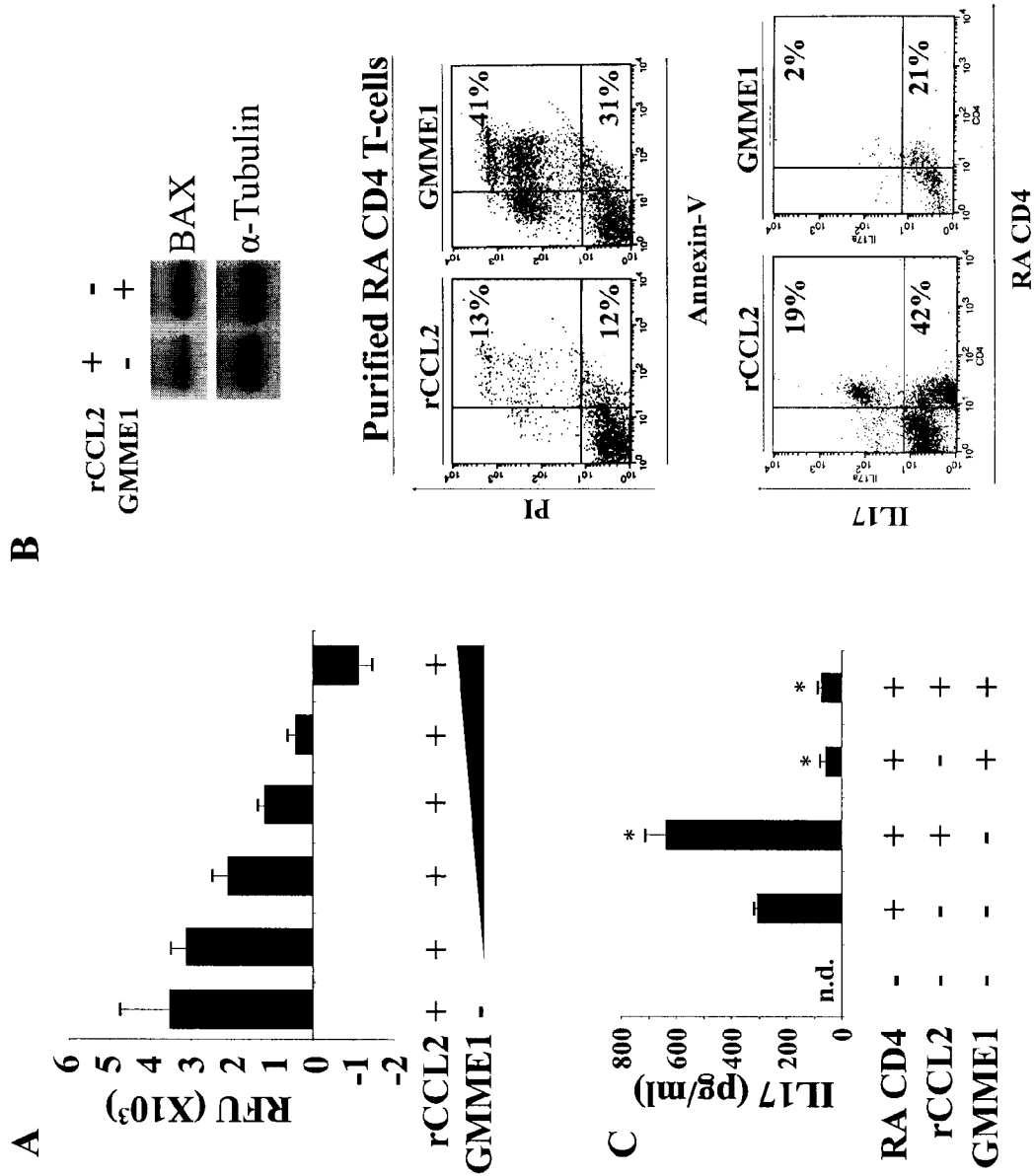
FIG. 16 shows biochemical effects of GMME1 in collagen induced rheumatoid arthritis (CI RA). (A) Inhibition of CD4 T cell migration by GMME1. B) Induction of apoptosis in CD4 T cells by GMME1. (C) Suppressed production of pro-inflammatory cytokines in the presence of CCL2.

The major biochemical response of CCL2 on target cells is the induction of a chemotactic response. Since the GMME1 C-terminus moiety is composed of a truncated variant of CCL2 missing 5 amino acids at its N-terminus, the chemotactic effect of the fusokine was investigated in the setting of a competitive assay using rCCL2 on purified RA-derived CD4 T-cells. rCCL2 can trigger CD4 T-cell migration, whereas the addition of increased concentrations of GMME1 inhibited such reaction until a complete migration blockade was achieved (FIG. 16A). Since the NF-κB and MAPK pathways are implicated in chemotaxis in addition to RA pathogenesis, the potential effects of the fusokine on these pathways were investigated. Interestingly, GMME1 does not lead to any noticeable effect on the phosphorylation of IκB-α, representative of NF-κB activation, whereas p38 was hyperphosphorylated, demonstrating a direct modulatory effect on the MAPK signalling pathway. Due to the fact that GMME1 induces apoptosis, all pro-apoptotic proteins (Bcl-2 pro-apoptotic family) were confirmed by western blot analysis of RA-derived CD4 T-cells cultured with rCCL2 or GMME1 for 48 hrs by an increased expression of the BAX protein (FIG. 16B upper panel). This observation was confirmed by an increased cell death percentage as shown by PI/Annexin-V co-staining (80% cell death in the GMME1 group as opposed to 15% in the rCCL2 control group; FIG. 16B lower panel). The effect of GMME1 on the secretion of IL17, a pro-inflammatory cytokine involved in RA exacerbation, was investigated in purified CD4 T-cells which were cultured in the presence of fixed syngeneic peritoneal macrophages presenting CII with or without rCCL2 in the presence of GMME1. In this context, macrophages act only as stimulators without secreting soluble factors interfering with the assay. As expected, the addition of rCCL2 exacerbated the secretion of IL17 from responder CD4 T-cells, whereas the addition of GMME1 in concentrations equimolar to rCCL2 robustly interrupted it (FIG. 16C, left panel). Intracellular staining of CD4 T-cells for IL17 demonstrated that about 19% of responding T-cells are indeed secreting IL17 in the presence of rCCL2 as opposed to about only 2% when GMME1 is present (FIG. 16C, right panel).

GMME1 Leads to RA Recovery and Depletion of Pathological Lymphomyeloid Cells

Figure 17:
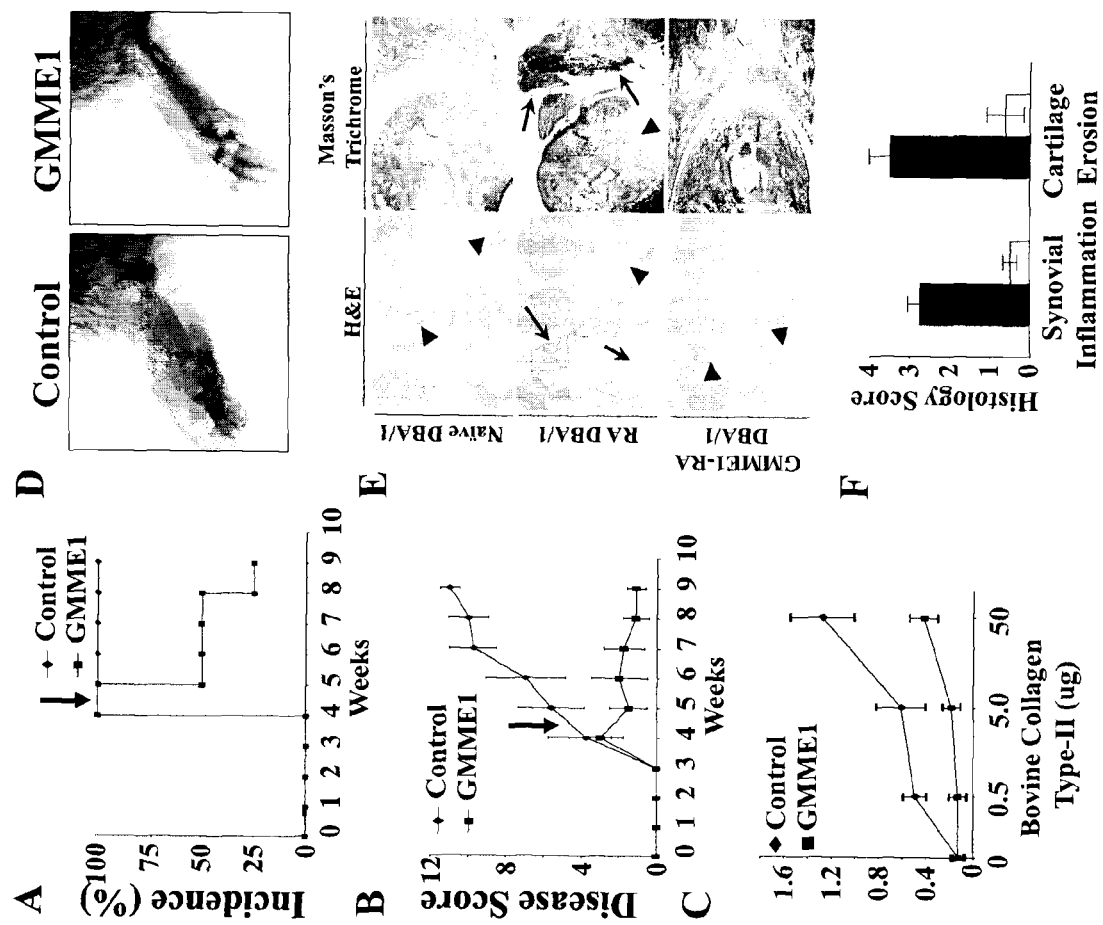
FIG. 17 shows CI RA progression with and without GMME1. (A) Reduction of RA incidence by GMME1. (B) Reduction of RA disease score by GMME1 according to paw scores. 0: no signs; 1: slight swelling; 2: moderate swelling; 3: pronounced edema with limited joint usage; and 4: excess edema with joint rigidity. (C) Reduction of paw size after GMME1 implantation. (D and E) Histopathological evaluation of RA mice with and without GMME1 implants. Hematoxylin/Eosin and trichrome masson's staining (D) and histology score (E). (F) Reduction of proliferation of splenocytes derived from CI RA mice treated with GMME1 and challenged with collagen.

The RA mouse model was chosen to test the efficacy of GMME1 since $CCR2^+$ lymphocytes, granulocytes and macrophages are implicated simultaneously in the physiopathology of this ailment. The in vivo delivery occurred as described in the EAE model. For the evaluation of the in vivo efficacy of GMME1 under pathological conditions, CII-treated BDA/1 mice with pre-established RA received GMME1 expressing MSC implants. Disease onset was 4 weeks after immunization, and one week after implantation a decrease in RA incidence (FIG. 17A) in addition to a robust decrease of the disease score, i.e. improvement of the disease, in the GMME1 group (FIG. 17B) was observed. Paw thickness of both RA mice treated or not treated with GMME1 was analysed and a substantial and significant decrease in size to normal range (FIG. 17C) was noticed after GMME1 treatment. Histological and quantitative analyses of the joints demonstrated great similarities between normal and GMME1-treated DBA/1 RA mice, whereas a robust infiltration of immune cells and bone erosion were observed in RA mice not treated with GMME1 (FIG. 17D). Similar results were obtained with the masson's trichrome staining (FIG. 17E). The H&E staining (left panel in E) led to a more quantitative analysis depicted in FIG. 17F. The obtained in vivo data correlates with the weak splenocyte recall response in the GMME1 group (FIG. 17F) as well as with the secretion of LIX.

In Vitro Analyses of the Effects of GMME1 on Disease Parameters

Figure 18:
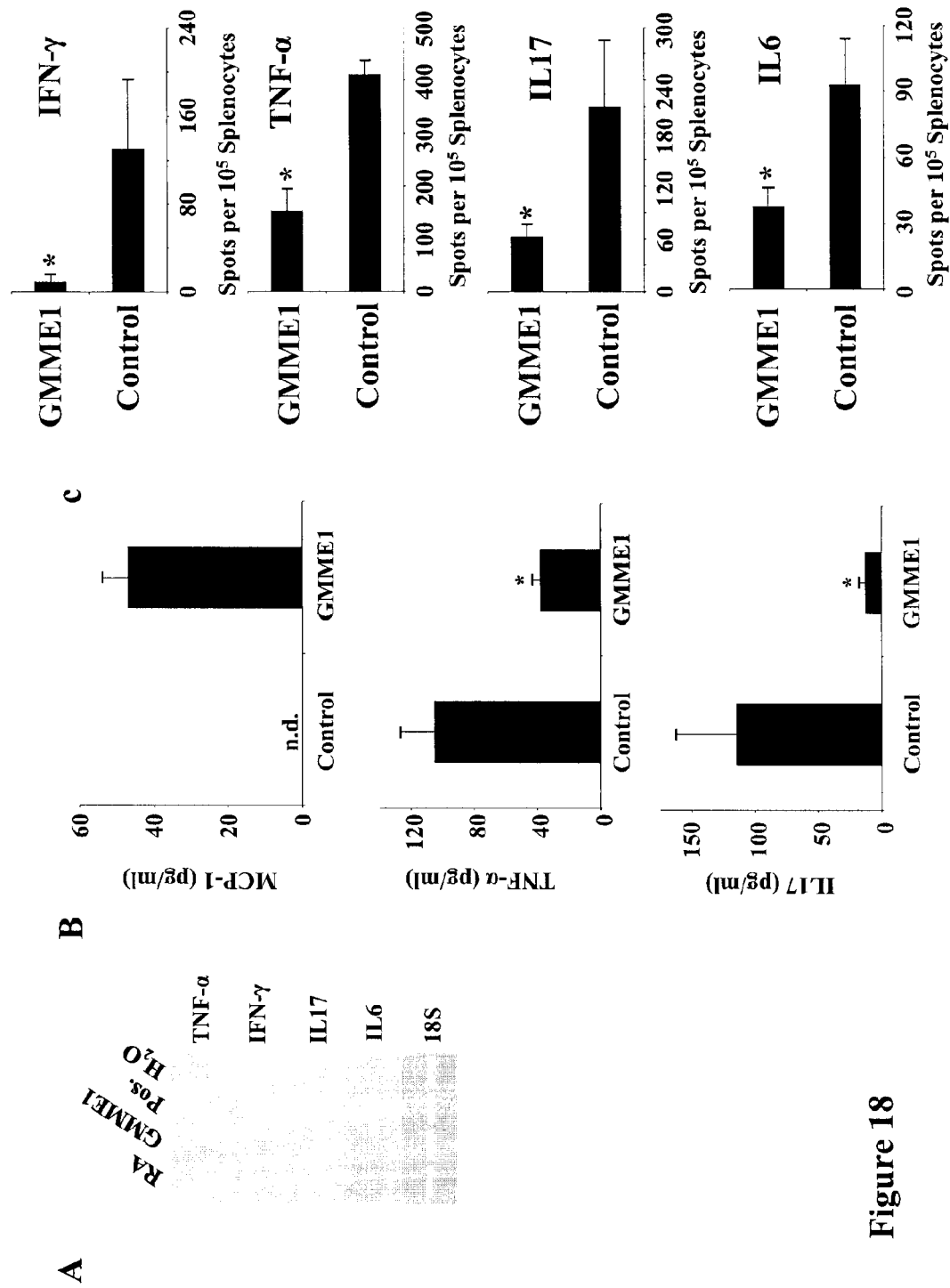
FIG. 18 shows the in vitro analysis of the effects of GMME1 on disease parameters. (A) Reduction of pro-inflammatory cytokines released into the synovial fluid of RA mice treated with GMME1 tested by qRT-PCR. (B) Reduction of pro-inflammatory cytokines in the serum of RA mice treated with GMME1 tested by ELISA. (C) Reduction of pro-inflammatory cytokines released by splenocytes derived from RA mice treated with GMME1 and stimulated with bovine type II collagen.

Analyses of various other cytokines in cells extracted from the joint infiltrates of RA mice treated with GMME1 demonstrated a blockade of the secretion of TNF-α, IFN-γ, IL17, and IL6 as opposed to the presence of these cytokines in the untreated RA mice (FIG. 18A). Plasma of RA mice in disease remission based on their treatment with GMME1 showed a systemic increase of detectable GMME1 as measured with a CCL2 ELISA. The GMME1 increase correlated negatively with levels of TNF-α and IL17 in the circulation (FIG. 18B). As a measure for the intensity of immune responses in RA mice, their splenocytes were collected and re-stimulated in vitro with increasing concentrations of CII. Contrary to untreated RA mice, splenocytes of GMME1 treated RA mice demonstrated a significant reduction of pro-inflammatory cytokines such as IFN-γ, TNF-α, IL17 and IL6 as detected in Elispot analyses.

Figure 19:
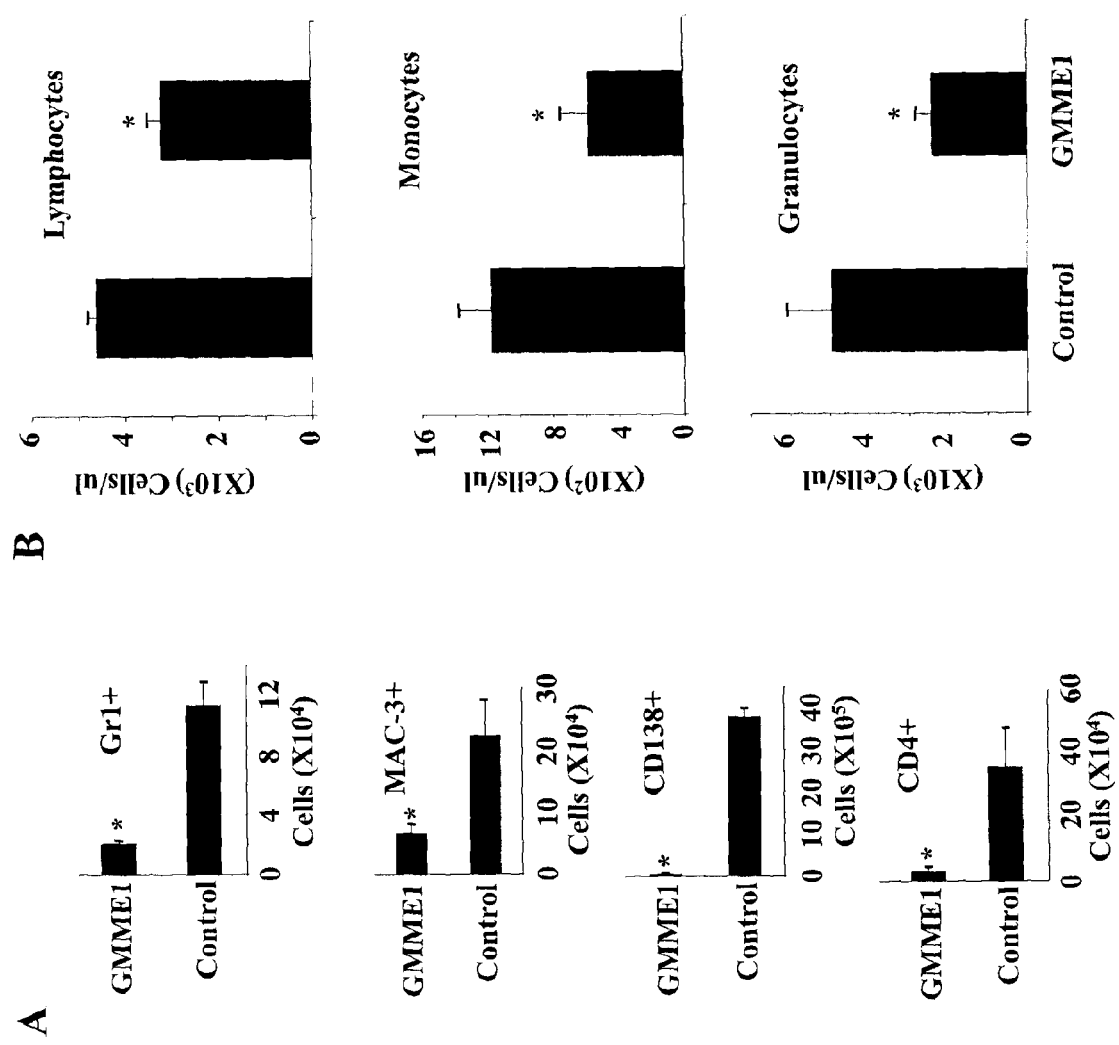
FIG. 19 shows the in vitro analysis of the effects of GMME1 on disease parameters. (A) Reduction of leukocyte infiltration (granulocytes, CD4 T cells, macrophages, and plasma cells) in the joint of RA mice treated with GMME1 tested by flow cytometry. (B) Reduction of serum leukocytes (lymphocytes, monocytes, and granulocytes) in RA mice treated with GMME1 tested by flow cytometry.

As a further confirmation of these observations, analyses of joint infiltrates demonstrated a decrease in absolute cell numbers of granulocytes, macrophages, CD4 T-cell as well as plasma cells (FIG. 19A). In addition, it was observed that absolute numbers of circulating lymphocytes, monocytes as well as granulocytes decreased significantly (FIG. 19B).

Figure 20:
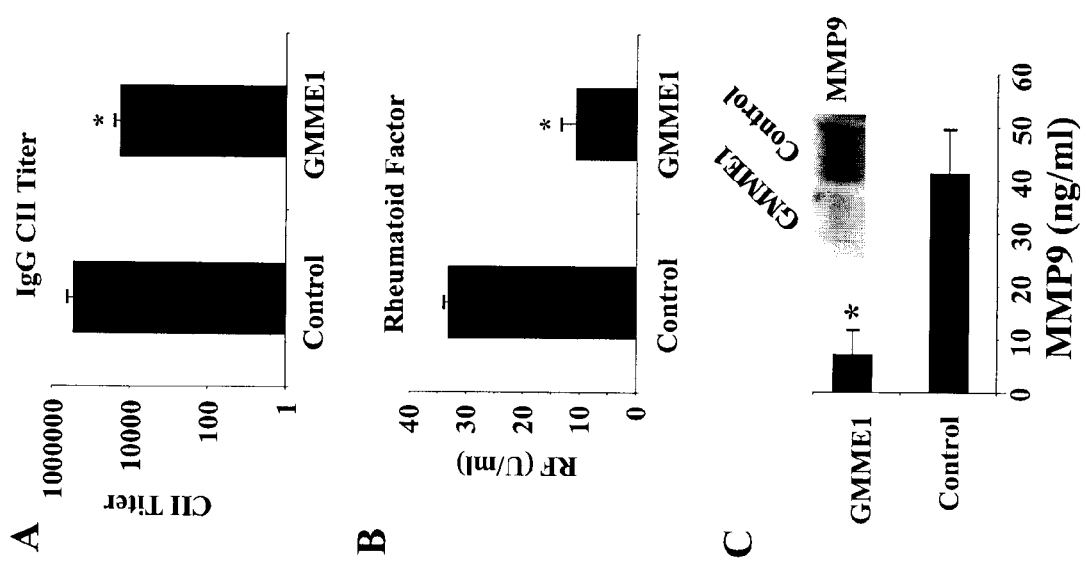
FIG. 20 shows the in vitro analysis of the effects of GMME1 on disease parameters. (A) Reduction of collagen type II specific IgG antibody titres in the serum by GMME1. (B) Reduction of rheumatoid factor (RF) units by GMME1. (C) Reduction of the tissue degrading MMP9 protein by GMME1.
Figure 21:
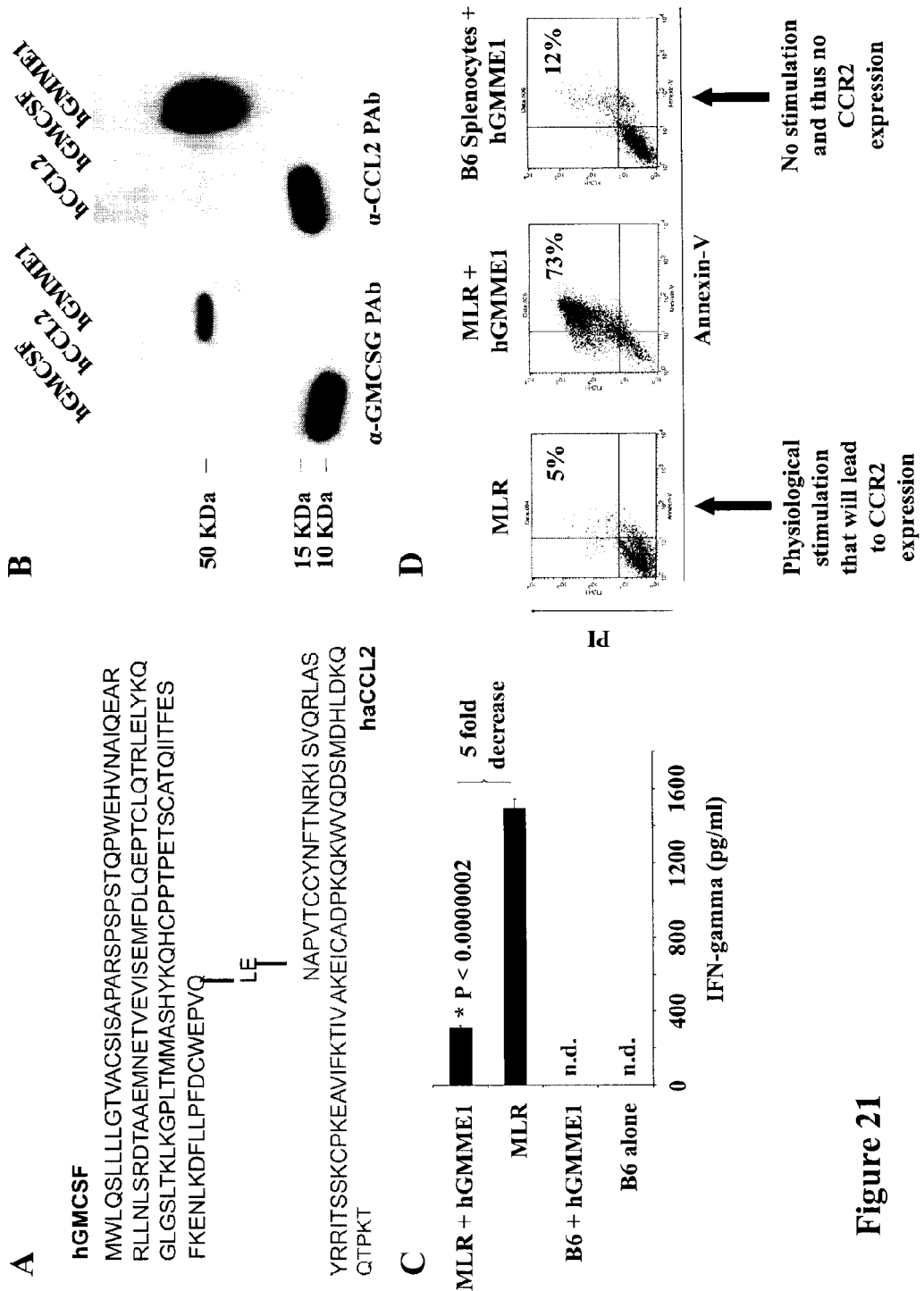
FIG. 21 shows the construction and expression of human GMME1 (hGMME1). (A) Schematic representation of the hGMME1 amino acid sequence (SEQ ID NO:4). (B) Expression of hGMME1 in conditioned media (CM) collected from transiently transfected HeLa cells and demonstrated by denaturing immunoblotting and detection by anti-huCCL2 and anti-huGM-CSF polyclonal antisera. HGM-CSF and hCCL2 were used as positive control. (C) hGMME1 does not affect CCR2$^{-/-}$ cells in a 1 and 2 way mixed lymphocyte reaction (MLR). IFN-gamma was tested by ELISA.

Since an important component of RA pathogenesis is humoral mediated, CII-specific antibody titres were analysed. A robust decrease was only detected in the GMME1 treated group (FIG. 20A). The plasma levels of RF (Rheumatoid Factor) were also significantly diminished in case of the GMME1 treated RA mice (FIG. 20B). Amongst the secreted factors implicated in the pathophysiology of RA, tissue-degrading enzymes, such as MMPs are induced and participate in cartilage digestion and bone deformation. Due to its significant role in RA pathogenesis, MMP9 was investigated and found to be highly induced by CII restimulation as detected both by ELISA and western blotting.

Differentiation of CCL2KO-MSC Expressing GMME1 into Adipocytes

Figure 22:
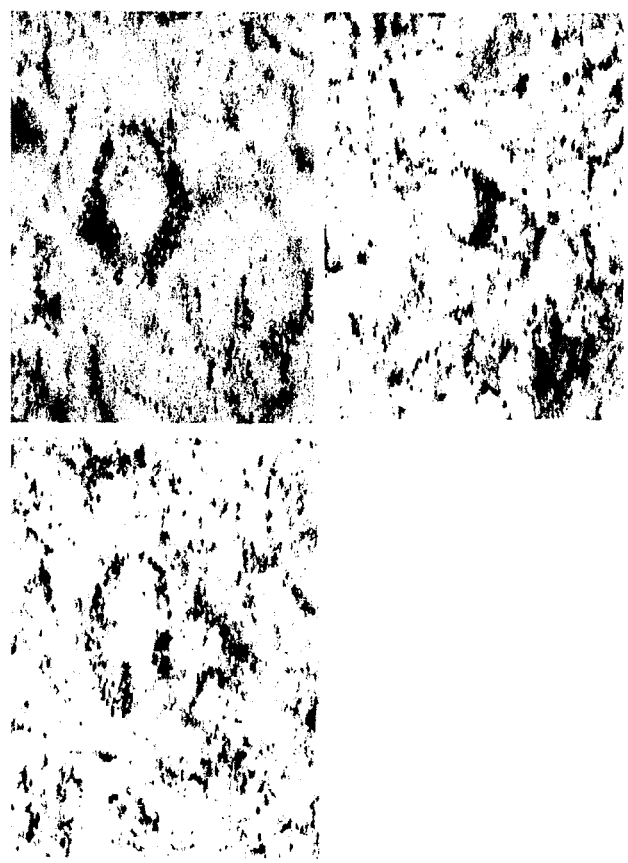
FIG. 22 shows the differentiation of CCL2KO-MSC expressing GMME1 into adipocytes.

CCL2KO-MSCs were grown in adipocytic milieu for about 3 weeks or until vesiculous cells appeared. The cells were then stained using a dye (oil red) that stains fat vesicles (no antibody used). Shown in FIG. 22 are 3 representative pictures of the cells.

Weight Reducing Effect of GMME1 in Mice Fed on Continually High Fat Diet

Figure 23:
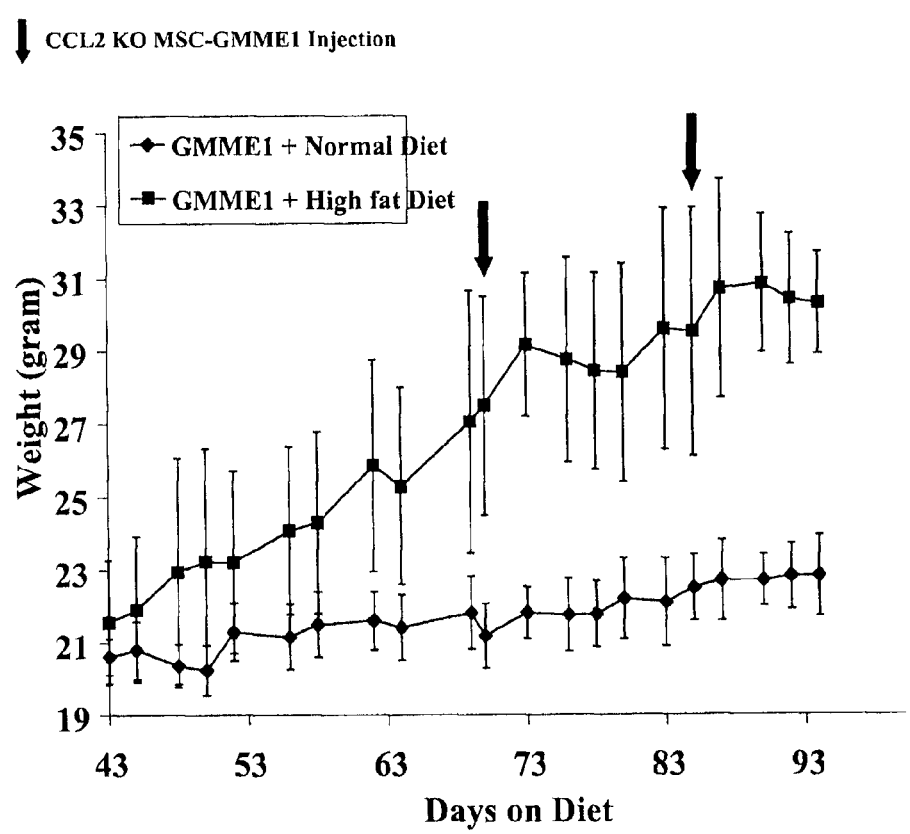
FIG. 23 shows the weight reducing effect of GMME1 in mice fed on continually high fat diet.

C57Bl/6 mice were fed a high fat diet. 4×10$^6$ CCL2KO-MSC expressing GMME1 were injected IP (according to the arrows) in these animals and weight was monitored every 48 hrs. Results show that injecting GMME1-MSCs IP to B6 mice on high fat diet stabilizes or slows down their increase in weight (FIG. 23).

Figure 24:
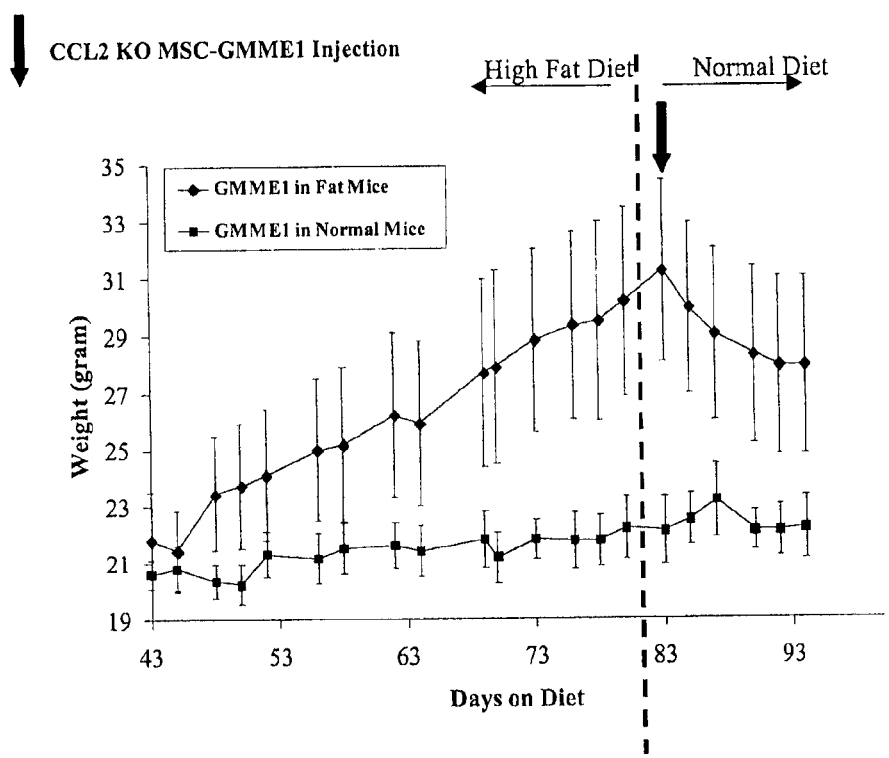
FIG. 24 shows the weight reducing effect of GMME1 in mice fed a high fat diet, returning to a normal diet and the lack of any effect of GMME1 on mice on a normal diet.

Weight Reducing Effect of GMME1 in Mice Fed a High Fat Diet, Returning to a Normal Diet and the Lack of any Effect of GMME1 on Mice on a Normal Diet Two groups of mice were used. One group was on a normal diet (lower one) and the second (upper) group was on a high fat diet until the cut off line. The effect of GMME1 on weight of mice was measured (FIG. 24). At the cut off line, the diet was changed from high to normal then the mice were given GMME1.

Figure 25:
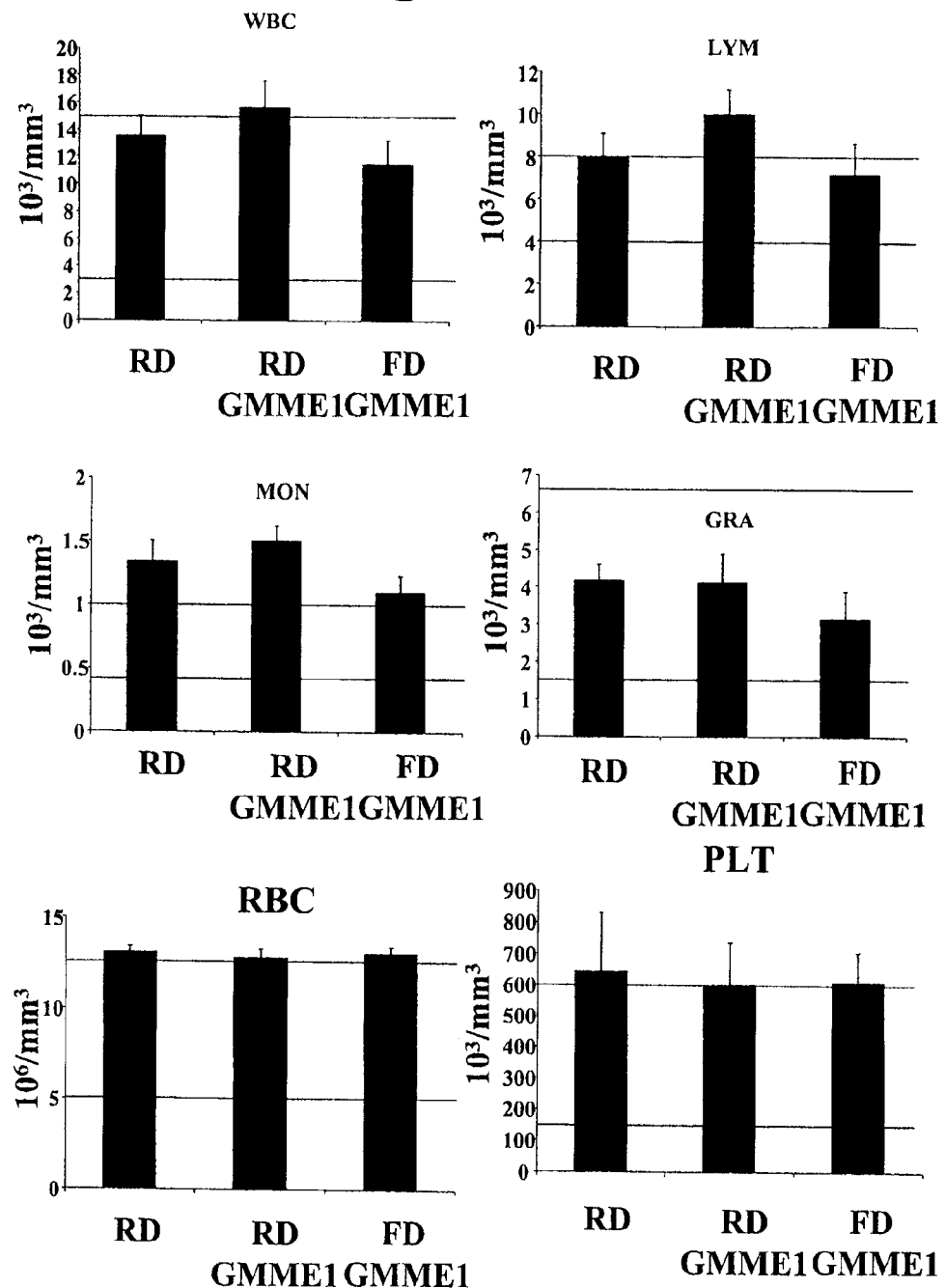
FIG. 25 shows a blood analysis in mice on a normal diet injected with GMME1 expressing CCL2KO-MSC.

Blood Analysis in Mice on a Normal Diet Injected with GMME1 Expressing CCL2KO-MSC The immune/haematological system is unaffected in these mice as shown by analysis of white blood cells, lymphocytes, monocytes, granulocytes, red blood cells and platelets (FIG. 25).

DISCUSSION

The present strategy enables the direct targeting of GPCR. CCR2 was chosen due to its wide involvement in various pathologies and expression profile on target effector cells. The developed novel fusokine, GMME1, is capable of specifically targeting CCR2 in various cell types both in vitro and in vivo. More specifically, GMME1 stimulation of HEK293T-cells transfected to express CCR2 triggered strong intracellular $Ca^{2+}$ influx. This biochemical response is usually followed by pro-caspase 3 cleavage and apoptosis (Van Raam et al. 2008), observations that were confirmed by the use of HEK293T-cells expressing CCR2.

GMME1 is capable of specifically targeting CCR2 on activated T-cells or macrophages leading to their cell death or the inhibition of antibody production by plasma cells. In addition, GMME1 can actively compete for CCR2 in the presence of its ligand CCL2 demonstrating a high capacity for competitive antagonism leading to a blockade in inflammatory cytokine secretion.

Tyrosine kinases are known to participate in GPCRs signalling (Mellado et al. 2001). Upon rCCL2 binding to CCR2, JAK2 kinase is recruited to the receptor to phosphorylate the tyrosine 139 residue promoting receptor homodimerization for consequent downstream signalling (Mellado et al. 2001). The initial $Ca^{2+}$ observation led the present inventors to investigate more in depth the outcome of GMME1 interaction with CCR2. Bioluminescence resonance energy transfer (BRET) became an increasingly popular technique allowing the distinction of random (nonspecific) from true oligomeric protein interactions (Bacart et al. 2008). As such, it would be possible to study the dynamic interaction taking place between the ligand of interest and the receptor, or the receptor and various recruited intracellular proteins (Gandia et al. 2008). The BRET data clearly demonstrate that GMME1 blocks the homodimerization of CCR2 upon binding at very low concentration as opposed to rCCL2. Such outcome can either lead to abnormal signalling or recruit other proteins known to target the receptor for degradation. rCCL2, on the other hand, leads to the opposite outcome. Such differential response, prompted the investigation of the recruitment of β-arrestin 2, a protein recruited to activated GPCRs mediating receptor internalization for rapid desensitization of the cell to external stimuli (Defea 2007). Without wishing to be bound by any theory, it is hypothesized that CCR2 is not recycled or targeted for degradation since a decrease in the BRET signal is obtained upon the addition of GMME1, suggesting a blockade of 1-arrestin recruitment. Overall, the BRET analysis suggests that GMME1 has the potential to bind CCR2 while blocking homodimerization, recruiting specific G proteins involved in $Ca^{2+}$ amplification while inhibiting receptor recycling.

The MAPK, AKT and JAK-STAT pathways are important for the induction of EAE pathologies. The sum of the unheralded biochemical effects of GMME1 demonstrate an asymmetrical signalling taking place in the MAPK pathway in addition to the complete inhibition of AKT and the activation of JAK-STAT leading to cellular apoptosis in a caspase-3 dependent manner.

In addition, apoptosis was also triggered by GMME1 on primary $CD3^+$ T-cells, $CD19^+$ B-cells as well as peritoneal macrophages. However, GMME1 activities seem to be CCR2 specific since C57Bl/6 CCR2−/− splenocytes stimulated with fixed allogeneic BALB/c splenocytes induced a strong IFN-gamma response. The addition of rCCL2 or mpCCL2 had no effects on CCR2−/− cells compared to the positive control. The fact that GMME1 pharmacological effects are lost on CCR2−/− cells suggest high target selectivity. Binding to and signalling through other CCR receptors could not have been invoked. Such selective GPCR modulation strategy demonstrates that GMME1 is not affected by chemokine receptor redundancy limiting therefore its potential toxicity.

In light of the potent depletion of CCR2-expressing lymphomyeloid cells induced by GMME1 in vitro, its effect was tested in vivo whether it could lead to EAE recovery in C57BL/6 mice. Within a fortnight, GMME1 led to near full recovery from symptomatic pre-established EAE. In addition, spleen atrophy observed at week 2 post GMME1 administration is consistent with lymphomyeloid depletion and is also completely reversible as demonstrated in the spleen of mice on long-term GMME1 following implant removal.

Compared to previously-reported antagonistic CCL2 derivatives behaving as passive dominant negative competitive inhibitors, GMME1 exhibits novel CCR2-driven signalling diametrically opposite to that of native CCL2. Indeed, GMME1 usurps CCR2 signal transduction machinery and induces the apoptotic cascade. The post translational derivative MCP-1 (9-76) or the 7ND mutant of CCL2 are considered decoys capable of preventing cells from responding to chemokines, blocking the induction of adhesion molecules, or changes in cytoskeleton. Another CCL2 mutant, P8A-MCP-1, acts as an antagonist by binding to CCR2 without triggering any biochemical response and thus by down-regulating the MAPK pathway.

The maladaptive interplay of immune cells involved in RA pathophysiology is a complex process and is known to implicate a cascade of reactions. It is believed that, following activation of B-cells—by an unknown mechanism—immunoglobulins and RFs are induced and deposited in synovial tissues. This subsequently leads to complement activation and recruitment of phagocytic cells, which further exacerbates synovial inflammation leading to edema, vasodilatation and infiltration of activated CD4 T-cells. Upon entry into the synovium, CD4 T-cells are reactivated by resident APCs leading to the secretion of pro-inflammatory factors including IFN-γ, TNF-α, IL6, and IL17. As a result, granulation occurs at the edges of the synovial lining (pannus) with extensive angiogenesis and production of MMPs that cause tissue damage. The synovium thickens and the cartilage underlying the bone begins to disintegrate leading to deformation. It is therefore very unlikely that targeting of any one inflammatory cytokine or cell population involved in disease ontogeny will bear meaningful clinical results. In this context, CCR2—as a therapeutic target—is of great interest since it is widely expressed on immune effector cells and predominantly on monocytes/macrophages. In fact, inflammatory monocytes in circulation are characterized as $CCR2^{hi} CX3CR1^{low}$, whereas $CCR2^{low} CX3CR1^{hi}$ cells are defined as resident monocytes. This further confirms the importance of CCR2 in inflammation due to the ubiquitous presence of monocytes and their focused migration within the host in response to CCL2 and other chemokines. Previous clinical studies using inhibitors or neutralizing antibodies for CCR2 in RA showed limited amelioration for various reasons. For example, the administration of the therapeutic antibody MLN102 failed due to its inefficiency in fully covering the entire CCR2 repertoire. A small molecule inhibitor of CCR2, MK0812, failed due to poorly tolerated off-target effects. More specifically, this inhibitor targeted CCR2 but also possessed a higher affinity for CCR5, a CCR2 homologous receptor. This lack of specificity is detrimental to RA since CCR5 is also expressed on Tregs and may therefore lead to their depletion explaining the lack of efficacy observed during phase II arthritis trial. In this respect, the observed CCR2-specific pro-apoptotic effect of GMME1 could be exploited as a new alternative to deplete pathogenic lymphomyeloid cells implicated in RA. The fusion of the CCL2 fragment 6-76 to GMCSF resulted in a fusion protein that induced different changes in the CCR2 conformation compared to CCL2 or mpCCL2, suggesting that GMME1 induced different downstream signalling. In addition, GMME1 did not lead to g-arrestin 2 recruitment, implicated in receptor down-regulation/recycling. As a result, the cells received various abnormal signalling such as strong $Ca^{2+}$ influx, hyperphosphorylation of p38, BAX induction and caspase-3 activation. In addition, the fusokine acquired the capacity to compete for CCR2 in the presence of the native ligand CCL2 as opposed to the parental 6-76 variant form of the chemokine.

As proof of the therapeutic potency of GMME1, the fusokine was expressed in $CCL2^{−/−}$ MSCs implanted as a neo-organoid in order to increase and prolong the bioavailability and test the pharmacokinetic properties of GMME1 in an RA mouse model. This methodology also allows the surgical removal of the implant at any time point especially if the ailment is resolved. Indeed, GMME1 was detected systemically in recovered mice in addition to a substantial decrease in levels of lymphomyeloid cells in circulation. Moreover, almost no immune cells were detected in the joints of GMME1-treated mice clearly demonstrating the potency of the fusokine in eradicating pathological immune cells. LIX is believed to play substantial roles in mediating polymorphonuclear cells joint infiltration and exacerbation of the inflammatory process. The minimal amount of LIX from host-derived cells found within joints of treated mice additionally confirms the therapeutic efficacy of GMME1.

Chemokine redundancy represents a major barrier in the development or rational design of therapies directed towards a specific G-coupled receptor. The specificity of GMME1 for CCR2 as demonstrated in the EAE study, demonstrates that it has a great advantage over many other experimental therapies since no off-target toxicities were observed. In summary, by targeting and selectively depleting CCR2-expressing lymphomyeloid cells, disease progression was completely inhibited and the production of most, if not all, pro-inflammatory factors identified so far in RA pathogenesis was markedly repressed. Thus, GMME1 is the lead member of a new class of drugs which may be of substantial clinical interest for RA and related ailments.

Human cells are considered xenogeneic to immunocompetent C57Bl/6 mice and would be incapable of growing due to cellular rejection by MHC-independent NK cells. In light of the remarkable effects induced by GMME1 in vitro, it was tested whether its expression could protect a xenograft from rejection in immunocompetent recipient animals. As proof of concept, null or GMME1-expressing HeLa cells were grafted in C57Bl/6 mice. The anticipated rejection of null HeLa cells was observed within a month whereas all GMME1 grafts were accepted. The continual outgrowth of the implants led to detectable amounts of GMME1 in the serum of grafted mice without affecting the levels of circulating WBCs. However, GMME1-induced cell death seems to occur mostly in the spleen since a significant decrease of both T and B lymphocytes percentage was observed. This lymphocyte-depletion is probably the cause of the permissive outgrowth of the graft and the increase of GMME1 release in circulation.

Triggering apoptosis in tumor cells is highly valuable for cancer therapies. The human multiple myeloma cell line U266 is known to express CCR2 and depend on autocrine hIL6 secretion for its own growth. The MTT assay using rCCL2 show that the normal ligand to CCR2 has no effect on these cells whereas mpCCL2 seems to help promoting proliferation while inhibiting hIL6 production. GMME1, at low quantities, completely blocked hIL6 secretion and led to no metabolically active cells following a 3 day treatment. The impediment of U266 growth by GMME1 adds another therapeutic utility for the fusokine as part of a local cancer therapy.

Obesity is state of chronic, low grade inflammation that is characterized by increased infiltration of macrophages, suggesting that these latter cells are an important source of inflammation in obese adipose tissue. Mesenchymal stem cells taken from CCL2 knock-out mice expressing GMME1 can still differentiate into adipocytes in vitro which suggests that the reduction of body weight induced by GMME1 does not involve the inhibition of the generation of new adipocytes. In addition, the haematological analysis demonstrates that monocytes, the pre-stage of macrophages infiltrating tissues, are not affected by GMME1. However, GMME1 might act via the interference with the activation of tissue controlling macrophages in the visceral fat tissue.

Taken together, the experiments demonstrate that GMME1 possesses novel biochemical properties that are distinct from both rCCL2 and mpCCL2, its MMP-derived antagonist derivatives, or their equimolar combination with rGMCSF since GMME1 disrupts normal CCR2 behaviour, triggers strong $Ca^{2+}$ influx, and leads to caspase-3 activation and subsequent apoptosis. The sum of these effects create a permissive state allowing the engraftment of xenogeneic cells in immunocompetent mice, can selectively kill tumor cel$^{ls}$ expressing CCR2, and leads to selective and potent apoptosis of CCR2-expressing lymphomyeloid cells and consequent immune suppression.

Methods

Animals, Cell Lines, Recombinant Proteins, Antibodies, and ELISA kits.

All used female mice were 6-8 weeks old (Jackson Laboratory, Bar Harbor, Me.). The Hela and U266 cell lines were cultured in DMEM (Wisent Technologies, Rocklin, Calif.) supplemented with 10% FBS (Wisent Technologies) and 50 U/ml of Pen/Strep (Wisent Technologies). Recombinant proteins (rGMCSF/rCCL2), their antibodies and $^a$nti-human CCL2 antibody were purchased form R&D systems (Minneapolis, Minn.). The α-tubulin specific antibody was purchased from Santa Cruz Biotechnology (Santa Cruz, Calif.). Antibodies directed against cleaved caspase 3, $p^{44}/42$, p38, p38, AKT, BAX and STAT5 were purchased from Cell Signalling Technology (Danvers, Mass.). rhMMP1 was purchased from Sigma-Aldrich (Oakville, ON, Canada). Anti-mouse Fcγ III/II, CD3, CD19, CD44, CD45, CD73, CD105, CD138 or isotype control antibodies for flow cytometry were purchased from BD Biosciences (San Diego, Calif.). ELISPOTS, CCR2 primers, apoptosis detection kits, ELISAs for mouse CCL2, mouse IFN-γ, mouse IL2/IL4/IL13/IL17, MMP9 reagents, mouse CXCL5 and mouse TNF-α were purchased from R&D systems. ELISAs for hIL6 were purchased from BD Biosciences. The Premo™ Cameleon Calcium Sensor was purchased from Invitrogen (Burlington, ON, Canada). All flow cytometry antibodies and bovine collagen type-II were purchased from BD Biosciences (San Diego, Calif.). AllPrep DNA/RNA Mini Kit was purchased from Qiagen (Alabama, USA). RNA extraction kit was purchased from Qiagen (Mississauga, ON, CANADA). CD3/CD28 beads and CFSE dye were purchased from Invitrogen (Burlington, ON, CANADA). Contigen was purchased from Bard Urological Division (Covington, Ga., USA). The $MOG_{35-55}$ was synthesized by Sheldon Biotech Center (McGill University, Montreal, Qc, Canada). Complete Freund's Adjuvant and Rheumatoid factor (RF) ELISA were obtained from Cedarlane (Montreal, Qc, Canada). The pertussis toxin was purchased from Sigma Aldrich (Oakville, ON, Canada). CD4 and CD8 T-cell enrichment kits were purchased from StemCell Technologies (Vancouver, BC, Canada) and a CD4 migration kit was obtained from Chemicon (Ontario, Canada). Inflammatory qRT-PCR arrays were purchased from SABiosciences (Frederick Md., USA) and used according to manufacturer's instructions. The 5-76 variant of mouse CCL2 (CCL2 5-76) was synthesized by Geneecust (Dudelange, Luxembourg). The regular mouse chow and the high fat feeding were purchased by Harlan Tekland, Madison, Wis.).

Fusokine Design and Expression

The fusokine is composed of 2 entities. mCCL2 was amplified by PCR in order to generate a 5-amino acid (aa) truncation at the N-terminus (without the mCCL2 secretion peptide (SP)) and subsequently cloned in frame with the cDNA encoding mGMCSF into the mammalian expression vector pCMV. As such, the chimeric transgene was expressed as a single open reading frame (pGMME1). HeLa cells were seeded at 65-80% confluency and transiently transfected using Polyfect (Qiagen, Mississauga, ON, Canada) and supernatant was tested by western-blot. Three days later, the supernatant was collected, concentrated using AMICONS (Millipore (Cambridge, Ontario, Canada) and tested by western-blot. HeLa cells were also transfected with a pGMME1 vector and selected with G418 for a total period of 3 weeks to generate stable expression of the fusokine. GMME1 expression levels were subsequently assessed using anti-CCL2 ELISA kit.

Prediction of Fusokine 3-Dimensional Model

The structural models of CCR2 and GMME1 were obtained by homology modeling using MODELLER 9v3 (University of California at San Francisco). The crystal structure of human $β_2$ adrenergic G-protein-coupled receptor (PDB entry: 2R4R) is used as a template for CCR2. For the fusion protein GMME1, crystal structures of human GM-CSF (PDB entry: 2 gmf) and CCL2 (PDB entry: 2nz1) are used as the templates for residues 21-190 in GMME1. Fold recognition method as implemented in PROSPECT 2.0 (Oak Ridge National Laboratory, Oak Ridge, Tenn.) was subsequently employed. The crystal structure of photosystem I protein (PDB entry: 1 pse) was identified as a template. Based on templates 2 gmf, 2nz1 and 1 pse, 100 structure models of GMME1 were generated and the one with lowest objective function was selected for further analysis.

Transfection of HEK293T-Cells for BRET Assays

HEK293T-cells were maintained in Dulbecco's modified Eagle's medium (DMEM) supplemented with 10% fetal bovine serum, and 100 units/ml penicillin and streptomycin. 24 h before transfection, cells were seeded at a confluency of 65-80% in 10 cm dishes. Transient transfections were performed using Polyfect according to manufacturer's instructions (Qiagen). In general, 8 μg of CCR2, or 0.1 μg of CCR2-RLuc transfected alone or with increasing quantities of YFP-tagged CCR2. For the β-arrestin recruitment assay, Rluc-tagged β-arrestin 2 was transfected, alone or with of YFP-tagged CCR2. After overnight incubation, transfection medium was replaced with fresh Dulbecco's modified Eagle's medium for 24 h to allow cell recovery. Transfected cells were then seeded in 96-well white plates (with clear bottoms that had been pre-treated with poly-D-lysine) and left in culture for 24 h before being processed for BRET assay.

Calcium Mobilization Assay by BRET

The mix of Premo™ cameleon calcium sensor reagent was used according to manufacture's instructions. Briefly, prepared solution was added on adherent HEK293T-cells expressing CCR2, as confirmed by flow cytometry, and incubated at room temperature for 2-4 hr with gentle rocking. Media was then replaced by complete media including Premo™ enhancer and cells incubated for an extra 2 hours at 37° C. Next, the enhancer medium was replaced with normal growth medium and returned to 37° C. for >16 hours to allow expression of the cameleon sensor. The following day, cells were trypsinized and plated in 96 well flat-bottomed assay plate and left at 37° C. for 12 hrs to allow cell adhesion before the addition of $Ca^{2+}$ mobilizing ligands and assessment by BRET. The stimulations were performed over 2 min.

BRET Measurements

For BRET measurements, cells were washed once with PBS 36 to 48 h after transfection. Readings were then collected using a multidetector plate reader MITHRAS LB940 (Berthold Technologies, Bad Wildbad, Germany) allowing the sequential integration of the signals detected in the 480±20 nm and 530±20 nm windows for luciferase and YFP light emissions respectively. The BRET signal is determined by calculating the ratio of the light intensity emitted by the Receptor-YFP over the light intensity emitted by the Receptor-RLuc. The values were corrected by subtracting the background BRET signal detected when the Receptor-RLuc construct was expressed alone. To assess the effects of ligands, 293T CM alone or inoculated with rMCP-1, and 293T-GMME1 CM were added and incubated at 37° C. for 5 min before BRET reading.

Flow Cytometry and Western Analysis

Antibody staining was performed according to manufacturer's instructions. For cleaved caspase 3 analysis by western blot, whole-cell lysate from sorted HEK293T-CCR2 or macrophages treated with the different test conditions were separated on 4-20% gradient SDS-PAGE (Invitrogen, Burlington, ON, Canada) and blotted with appropriate antibodies according to manufacturer's instructions.

Apoptosis Analysis

For apoptosis assays, $10^6$ HEK293T-cells expressing CCR2 or peritoneal macrophages cultured for 24 hrs with equimolar concentrations of rGMCSF, rCCL2, mpCCL2, rGMCSG/rCCL2, rGMCSF/mpCCL2, rGMCSF/mpCCL2, or GMME1 were lysed and whole cell lysate was loaded on a 4-20% gradient gel and probed with anti-cleaved caspase-3 according to manufacturer's instructions. The result obtained with GMME1 was confirmed by PI and annexin-V staining. Staining for purified CD4 and CD8 T-cells was performed similarly. It was then analyzed by flow cytometry with a Becton-Dickinson FACScan. To generate antagonist mpCCL2 in vitro, 10 ng of pure rhMMP1 was added directly to 50 µg pure rCCL2 in PBS for a period of 4 hrs at 37° C. mpCCL2 MMP-processed CCL2 was directly used in assays without further modifications. For cleaved caspase 3 analysis by western blot, CCR2-transiently transfected HEK283T cells were sorted, stimulated with the cytokine conditions then whole-cell lysates was and blotted with caspase-3 antibodies.

Purified RA CD4 T-cells were cultured for a period of 48 hrs in the presence of equimolar concentration of rCCL2 or GMME1 and analysed for the expression of BAX.

Mixed Lymphocyte Reaction (MLR)

The supernatant of co-cultured $10^5$ splenocytes-derived from BALB/c or C57Bl/6 mice for 72 hrs with equimolar concentrations of chemokines was centrifuged and used to detect IFN-gamma secretion by ELISA. For the MLR assay using CCR2-/- C57Bl/6 splenocytes, $10^5$ splenocytes of BALB/c were fixed with paraformaldehyde prior to their addition to C57Bl/6 splenocytes. After 3 days of culture with the test conditions, IFN-gamma levels were assessed by ELISA. As the human CCL2 is not species specific, i.e. it interacts with murine CCR2, and the human GMCSF does not seem to be involved in binding but rather in steric hindrance of CCR2, human GMME1 and murine GMME1 could be used interchangeably in a purely murine MLR.

OVA Immunization and ELISPOT Assay

BALB/c mice were immunized with 1 µg of rOVA per animal (n=5) twice at an interval of 2 weeks. ELISPOT assays were then performed using their splenocytes according to manufacturer's instructions. Briefly, rOVA-coated ELISPOT plates (Millipore, Cambridge, Ontario, Canada) were washed 3× with PBS, blocked with 1% BSA before the addition of cells under different test conditions. Following 3 washes with PBS, secondary anti-mouse alkaline phosphatase-labelled antibodies were added for 4 hrs at 4° C. before development and counting of spots.

Xenogenic HeLa Transplantations

Xenogeneic transplantations were performed by injecting $10^6$ live HeLa-null or GMME1 cells, secreting 92 pg/$10^6$/24 hr, in immunocompetent C57Bl/6 mice. Implants survival and growth were followed over time. For white blood cell counts, 20 µl of blood was collected at day 16 and the level of circulating GMME1 and WBC count was analyzed using the Z2 coulter Particle Count and Size analyzer (BD Biosciences). For spleen analysis, animals were sacrificed and their spleen was removed and measured for size before preparing a single cell suspension to assess the level of CD3e and CD19 lymphocytes. The same transplantation was performed in NOD-SCID mice.

GMME1 Effects on U266 and EG7

Biochemical Analysis

To test the proliferative property of GMME1, the mouse lymphoma EG7 or human multiple myeloma U266 cell lines were plated at a density of $10^5$ cells/well in a 96-well plate and treated with increasing concentrations of cytokines for 72 hours. The reaction was read at 570 nm after adding 20 µL of 3-(4,5-dimethylhiazol-2-yl)-2,5-diphenyltetrazolium bromide (MIT). For Apoptosis analysis, the mouse EG7 or human U266 cell lines were cultured for 48 hrs with equimolar concentrations (1.5 pmol) of CCL2 (1-76), CCL2 (5-76), or GMME1 then analyzed by PI/Annexin-V. The results were confirmed by western-blotting performed on the lysate-derived from treated cell lines probed with anti-BAX antibodies. For hIL6 secretion assessment by U266, the level of this cytokine was quantified by ELISA following the different cytokine treatments. For signalling analysis, a sandwich ELISA for mouse/human STAT3 was performed.

Cancer Induction and Treatments

For the study of the locoregional effect of GMME1 on tumor development, 2×$10^6$ MSC-GFP were co-implanted with $10^6$ EG7 cells subcutaneously (sc) in immunocompetent C57Bl/6. For the analysis of a systemic efficacy of the fusokine, $10^6$ EG7 cells were injected sc in immunocompetent C57Bl/6 mice on one side, and a sc implant of contigen-embedded gene-engineered MSCs (2×$10^6$ cells per implant)

was injected on the opposite flank as previously described (Eliopolous et al. 2008). Tumor appearance and volume were assessed every 48 hrs. To investigate the levels of circulating GMME1 in treated mice, the sera were collected at week 3 post-implantation of the neo-organoid and screened by CCL2 ELISA to detect the CCL2 moiety of the fusokine according to manufacturer's instructions.

Induction of CCR2 Expression in stimulated CD4 T cells and the effects of GMME1

For CCR2 induction, CD4 T-cells were purified with a Spinsep kit and cultured in 1:1 ratio with anti-CD3/CD28 beads in 96 well plates for 72 hrs. Cells were washed and analyzed for CCR2 expression by RT-PCR and flow cytometry. For in vitro proliferation assays, CD4 T-cells were labelled with 5 ug/ml CFSE for 8-10 min at 37° C. and then washed once with complete medium and three times with PBS. To assess the proliferation induced by the CD3/CD28 beads in the presence of the fusokine over time, cells were treated with GMME1 and analysed daily by flow cytometry. Supernatants were collected daily and assessed by ELISA for IL2 levels.

qRT-PCR on Stimulated Splenocytes

RNA was extracted from mouse cells using Qiagen (Mississauga, ON) RNeasy minikit and Qiashredder columns according to the manufacturer's instructions. 1 μg of RNA was reverse transcribed using $RT^2$ First Strand Kit and applied to PCR array plates, both from SABiosciences (Frederick, Md.). Plates were processed in an Applied Biosystems 7500 Fast Real-Time PCR System, using automated baseline and threshold cycle detection. Data was interpreted by using SABiosciences' web-based PCR array data analysis tool.

Biochemical Responses and Signalling Analysis

For signalling analysis, EAE-derived CD4 T-cells were purified and treated for 5 min with 1 pmol of rCCL2 or GMME1 then lysed using ice-cold cell lysis buffer before their sonication. The activation of p38, p44/42, pAKT, and pSTAT3 were probed by WB using 4-20% gradient SDS-PAGE gels and appropriate antibodies.

To investigate the effect of GMME1 at the molecular level, RA-derived CD4 T-cells were stimulated with rCCL2 or GMME1 for 10 min and both NF-κB and p38 were analyzed.

APC Assays

To analyse the effect of GMME1 on CD4 T-cells during antigen presentation, APC assays were performed using peritoneal macrophages collected from retired breeder C57Bl/6 mice. Upon binding and washing from non-adherent cells, macrophages were treated with $MOG_{35-55}$ and CII, respectively, for 24 hrs, washed and fixed using 2% paraformaldehyde before the addition of enriched CD4 T-cells specific for $MOG_{35-55}$ and CII under different treatment conditions. Supernatants were collected and centrifuged 72 hrs later for IFN-γ and IL17 analysis by ELISA. For IL17 intracellular staining, CD4 T-cells were collected from the assay, washed, and labelled with CD4 before fixation. After the wash, stained cells were permeabilized, stained with anti-IL17A antibody and subsequently analyzed by flow cytometry.

Gene Engineering MSC to Express GMME1

Whole bone marrow from femurs and tibias of $CCL2^{-/-}$ C57BL/6 mice was harvested and placed in culture in complete media until the appearance of a homogeneous MSC polyclonal population, which was later on phenotyped by flow cytometry while their plasticity tested by inducing them to differentiate into osteoblasts and adipocytes. The GMME1 cDNA was cloned in the AP2 retroviral plasmid and retropracticles generated as shown previously (Ansari et al. 2007). Concentrated retroparticles were then used to gene modify $CCL2^{-/-}$ C57Bl/6 MSCs. Secretion and expression levels of GMME1 by MSCs were analyzed by WB and CCL2 ELISA respectively. For CCR2 expression on MSCs, RT-PCR was performed on extracted RNA using purchased primers.

It was previously demonstrated that wild-type MSCs could generate in a paracrine fashion truncated CCL2 (5-76) capable of antagonizing CCR2-expressing cells (Rafei et al. 2009b). Therefore, $CCL2^{-/-}$ MSCs were used in this study to avoid any confounding effects arising from endogenous MSC production of CCL2 and derivatives. The generation and concentration of green fluorescent protein (GFP) or GMME1 retroparticles using the bicistronic AP2 vector were generated as previously reported (Rafei et al. 2009a). The level of GMME1 expression was analyzed through the assessment of GFP by flow cytometry, while GMME1 secretion level was quantified using a CCL2 ELISA.

EAE Induction and $CCL2^{-/-}$ MSC-GMME1Contigen Implantation

The synthetic $MOG_{35-55}$ peptide was emulsified in Complete Freund's Adjuvant and injected subcutaneously (sc) at the base of the tail. Animals also received pertussis toxin immediately after the sc injection by IP injections, repeated two days later. Mice were clinically scored every 2 days as follows: 0, no disease; 1, floppy tail; 2, hind limb weakness; 3, partial hind limb paralysis; 4, complete hind limb paralysis; 5, moribund stage. Following the appearance of EAE symptoms, all groups were normalized to possess a grade 2 average before receiving a subcutaneous implant of contigen-embedded MSCs as a neo-organoid as previously described by our group (Coffield et al. 2003). Contigen implants contained $CCL2^{-/-}$ MSCs gene-engineered to express GMME1 or null $CCL2^{-/-}$ MSC ($2 \times 10^6$ cells per implant).

Hematological Analysis

To investigate the levels of circulating pro-inflammatory cytokines, mice sera were collected weekly from treated EAE-mice 1 week following MSC implantation and tested by ELISA. For antibody titer, ELISA plates were coated with 1 mg/ml of MOG peptide then screened using diluted sera to calculate final titres. White blood cell (WBC) count was performed using the Z2 coulter Particle Count and Size analyzer (BD Biosciences). This count was applied in the analyses of the autoimmune and the obesity models.

Histological Analysis

For histological analysis, EAE mice were perfused with PBS and their spinal cords removed. For H&E staining, spinal cords were fixed, embedded and cut. For CD4 and CD8 immunohistology, sections were frozen before cutting and staining.

Paws of sick or treated RA mice were removed, fixed in 4% formalin and decalcified for a week before performing Hematoxylin and Eosin (H&E) or masson's trichrome stainings. These sections were then used to analyze synovial inflammation and cartilage erosion using the following score: 0 for no change; 1 for partial change; 2 for moderate change; and 3 for massive change.

Induction of Mouse Arthritis

CII was emulsified in Complete Freund's Adjuvant (Cedarlane, Montreal, Qc, Canada) containing *Mycobacterium tuberculosis* H35RA (Difco Laboratories, Detroit, Mich., USA) and injected subcutaneously (sc) at the base of the tail. The same injection was repeated 3 weeks later. Mice were clinically scored every week. Following the appearance of RA symptoms, all groups were normalized to possess a total average grade of 4 before receiving $CCL2^{-/-}$ MSCs expressing GMME1 as part of a contigen neo-organoid implanted subcutaneously ($5 \times 10^6$ cells per implant). Grading consisted of giving a score of 0-4 for each paw and adding all obtained scores for each mouse for a maximum of 12 per mouse with scores of 0: no signs; 1: slight swelling; 2: moderate swelling; 3: pronounced edema with limited joint usage; and 4: excess edema with joint rigidity. Mice were bled for systemic cytokine analysis and assessment of circulating lymphomyeloid cells.

Migration Assays in RA-Derived CD4 T-Cells

After the purification of RA CD4 T-cells by SpinSep, lymphocytes were used in a migration assay using rCCL2 as the chemoattractant with a consistent dose of 1 pmol at the bottom chamber. To investigate the anti-chemotactic ability of the fusokine, an increasing concentration of GMME1 was added on the cells at the top chamber starting at 0.01 pmol and increasing by 2 fold. The migration was set-up over 12 hrs and cells at the bottom chamber were lysed, stained and read using a fluorescence reader.

In Vitro Recall Response Assays in RA-Joint Infiltrates

After removal of fat and muscle, joints from RA mice were minced into small pieces with scissors, which were resuspended in 0.5% trypsin solution for about 1 hour at 37° C. Tissues were then washed and incubated with a collagenase solution (2 ug/ml) for another hour. The obtained cell suspension was centrifuged and resuspended in splenocytes media for further analysis. To induce an in vitro proliferation response, collected cells were cultured in the presence of increasing concentrations of bovine CII and proliferation assessed by 3-(4,5-Dimethylthiazol-2-yl)-2,5-diphenyltetrazolium bromide (MTT; Sigma-Aldrich, Oakville, ON, Canada).

Cells collected from joint infiltrates were plated for 48 hrs in splenocytes media and supernatant analyzed by ELISA. All remaining cytokines were analyzed by RT-PCR using RNA extracted from collected cells. The remaining cells were stained and analyzed by flow cytometry for the assessment of immune infiltrates.

To analyse the systemic immune response, cell proliferation was assessed in splenocytes derived from sick or treated RA mice and cultured in in the presence of increasing concentrations CII for 3 days.

Splenocytes derived from sick or treated RA mice were used in ELISPOT assays to detect the presence of IFN-γ, TNF-α, IL17 and IL6. Supernatants were analyzed for MMP9 by ELISA and western blot.

Humoral Response in RA Sera

The induction of the humoral response in RA mice was assessed by ELISA. Plates were coated with 1 mg/ml of CII and sera from sick or treated RA mice were analysed for the CII specific titres. The sera were analysed for the detection of RF levels according to the manufacturer's instructions.

Adipocyte Differentiation

CCL2KO-MSCs were grown in adipocytic milieu for about 3 weeks or until vesiculous cells appeared and stained with oil red as described in Eliopoulos et al. (2005).

Statistical Analysis

P values were calculated by paired Student t-test.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosures as come within known or customary practice within the art to which the disclosure pertains and as may be applied to the essential features herein before set forth, and as follows in the scope of the appended claims.

TABLE OF SEQUENCES:

MOUSE GMME1

DNA Sequence (SEQ ID NO: 1)

ATGTGGCTGCAGAATTTACTTTTCCTGGGCATTGTGGTCTACAGCC
TCTCAGCACCCACCCGCTCACCCATCACTGTCACCCGGCCTTGGAA
GCATGTAGAGGCCATCAAAGAAGCCCTGAACCTCCTGGATGACATG
CCTGTCACGTTGAATGAAGAGGTAGAAGTCGTCTCTAACGAGTTCT
CCTTCAAGAAGCTAACATGTGTGCAGACCCGCCTGAAGATATTCGA
GCAGGGTCTACGGGGCAATTTCACCAAACTCAAGGGCGCCTTGAAC
ATGACAGCCAGCTACTACCAGACATACTGCCCCCCAACTCCGGAAA
CGGACTGTGAAACACAAGTTACCACCTATGCGGATTTCATAGACAG
CCTTAAAACCTTTCTGACTGATAACGCCCCACTCACCTGCTGCTAC
TCATTCACCAGCAAGATGATCCCAATGAGTAGGCTGGAGAGCTACA
AGAGGATCACCAGCAGCAGGTGTCCCAAAGAAGCTGTAGTTTTTGT
CACCAAGCTCAAGAGAGAGGTCTGTGCTGACCCCAAGAAGGAATGG
GTCCAGACATACATTAAAAACCTGGATCGGAACCAAATGAGATCAG
AACCTACAACTTTATTTAAAACTGCATCTGCCCTAAGGTCTTCAGC
ACCTTTGAATGTGAAGTTGACCCGTAAATCTGAAGCTAATGCATCC
ACTACCTTTTCCACAACCACCTCAAGCACTTCTGTAGGAGTGACCA
GTGTGACAGTGAACTAGTGTGACTCGGACTGTGATGCCTTGCTAG

Amino-acid Sequence (SEQ ID NO: 2)

MWLQNLLFLGIVVYSLSAPTRSPITVTRPWKHVEAIKEALNLLDDM
PVTLNEEVEVVSNEFSFKKLTCVQTRLKIFEQGLRGNFTKLKGALN
MTASYYQTYCPPTPETDCETQVTTYADFIDSLKTFLTDDNAPLTCC
YSFTSKMIPMSRLESYKRITSSSRCPKEAVVFVTKLKREVCADPKK
EWVQTYIKNLDRNQMRSEPTTLFKTASALRSSAPLNVKLTRKSEAN
ASTTFSTTTSSTSVGTVTSVTVN

Human GMME1

DNA Sequence (SEQ ID NO: 3)

ATGTGGCTGCAGAGCCTGCTGCTCTTGGGCACTGTGGCCTGCAGCA
TCTCTGCACCCGCCCGCTCGCCCAGCCCCAGCACGCAGCCCTGGGA
GCATGTGAATGCCATCCAGGAGGCCCGGCGTCTCCTGAACCTGAGT
AGAGACACTGCTGCTGAGATGAATGAAACAGTAGAAGTCATCTCAG
AAATGTTTGACCTCCAGGAGCCGACCTGCCTACAGACCCGCCTGGA
GCTGTACAAGCAGGGCCTGCGGGGCAGCCTCACCAAGCTCAAGGGC
CCCTTGACCATGATGGCCAGCCACTACAAGCAGCACTGCCCTCCAA
CCCCGGAAACTTCCTGTGCAACCCAGATTATCACCTTTGAAAGTTT
CAAAGAGAACCTGAAGGACTTTCTGCTTGTCATCCCCTTTGACTGC
TGGGAGCCAGTCCAGCTCGAGGCCCTTCTGTGCCTGCTGCTCATAG
CAGCCACCTTCATTCCCCAAGGGCTCGCTCAGCCAGATGCAATCAA
TGCCCCAGTCACCTGCTGCTATAACTTCACCAATAGGAAGATCTCA
GTGCAGAGGCTCGCAAGCTATAGAAGAATCACCAGCAGCAAGTGTC
CCAAAGAAGCTGTGATCTTCAAGACCATTGTGGCCAAGGAGATCTG
TGCTGACCCCAAGCAGAAGTGGGTTCAGGATTCCATGGACCACCTG
GACAAGCAAACCCAAACTCCGAAGACTTGAACACTCACTCCACAAC
CCAAGAATCTGCAGCTAG

Amino-acid Sequence (SEQ ID NO: 4)

MWLQSLLLLGTVACSISAPARSPSPSTQPWEHVNAIQEARRLLNLS
RDTAAEMNETVEVISEMFDLQEPTCLQTRLELYKQGLRGSLTKLKG
PLTMMASHYKQHCPPTPETSCATQIITFESFKENLKDFLLPFDCWE
PVQLENAPVTCCYNFTNRKISVQRLASYRRITSSKCPKEAVIFKTI
VAKEICADPKQKWVQDSMDHLDKQTQTPKT

REFERENCES

Ansari A W, Heiken H, Moenkemeyer M, Schmidt R E. Dichotomous effects of C-C chemokines in HIV-1 pathogenesis. *Immunol Lett.* 2007 May 15; 110(1):1-(2007).

Bacart J, Corbel C, Jockers R, Bach S, Couturier C. The BRET technology and its application to screening assays. Biotechnol J. 3(3):311-24 (2008).

Campbell, J. J. & Butcher, E. C. Chemokines in tissue-specific and microenvironment-specific lymphocyte homing. *Curr. Opin. Immunol.* 12, 336-341 (2000).

Cheung P F, Wong C K, Lam C W. Molecular mechanisms of cytokine and chemokine release from eosinophils activated by IL-17A, IL-17F, and IL-23: implication for Th17 lymphocytes-mediated allergic inflammation. J. Immunol. 180 (8):5625-35 (2008)

Coffield V M, Jiang Q, Su L. A genetic approach to inactivating chemokine receptors using a modified viral protein. Nat. Biotechnol. 21(11):1321-7 (2003)

Defea K. Beta-arrestins and heterotrimeric G-proteins: collaborators and competitors in signal transduction. Br J. Pharmacol. 153 Suppl 1:S298-309 (2007)

Demetri G D, Griffin J D. Granulocyte colony-stimulating factor and its receptor. *Blood.;* 78: 2791-808 (1991).

Dranoff G, Jaffee E, Lazenby A, Golumbek P, Levitsky H, Brose K, Jackson V, Hamada H, Pardoll D, Mulligan R C. Vaccination with irradiated tumor cells engineered to secrete murine granulocyte-macrophage colony-stimulating factor stimulates potent, specific, and long-lasting anti-tumor immunity. *Proceedings of the National Academy of Sciences.* 90: 3539-43 (1993).

Eliopoulos N, Lejeune L, Martineau D, Galipeau J. Human-compatible collagen matrix for prolonged and reversible systemic delivery of erythropoietin in mice from gene-modified marrow stromal cells. Mol. Ther. 2004; 10(4): 741-8.

Eliopoulos N, Stagg J, Lejeune L, Pommey S, Galipeau J Allogeneic marrow stromal cells are immune rejected by MHC class I- and class II-mismatched recipient mice. Blood. 2005 Dec. 15; 106(13):4057-65

Eliopoulos N, Francois M, Boivin M N, Martineau D, Galipeau J. Neo-organoid of marrow mesenchymal stromal cells secreting interleukin-12 for breast cancer therapy. Cancer Res. 2008; 68(12):4810-8.

Engel B C, Bauer G, Pepper K A, Bockstoce D C, Yu X J, Chen S Y, Kohn D B. Intrakines—evidence for a transcellular mechanism of action. Mol. Ther. 165-70 (2000)

Fife, B. T., Huffnagle, G. B., Kuziel, W. A. & Karpus, W. J. CC chemokine receptor 2 is critical for induction of experimental autoimmune encephalomyelitis. *J. Exp. Med.* 192, 899-906 (2000). samedi Gandia J, Lluis C, Ferré S, Franco R, Ciruela F. Light resonance energy transfer-based methods in the study of G protein-coupled receptor oligomerization Bioessays. 30(1):82-9 (2008).

Gillies S D, Lan Y, Brunkhorst B, Wong W K, Li Y, Lo K M Bi-functional cytokine fusion proteins for gene therapy and antibody-targeted treatment of cancer. *Cancer Immunology Immunotherapy.* 51: 449-460 (2002).

Huang D R, Wang J, Kivisakk P, Rollins B J, Ransohoff R M. Absence of monocyte chemoattractant protein 1 in mice leads to decreased local macrophage recruitment and antigen-specific T helper cell type 1 immune response in experimental autoimmune encephalomyelitis. *J Exp Med.* 193(6):713-26 (2001).

Irvine K R, Rao J B, Rosenberg S A, Restifo N P. Cytokine enhancement of DNA immunization leads to effective treatment of established pulmonary metastases. *Journal of Immunology.* 156: 238-45 (1996).

Israel F. Charo, Mark B. Taubman. Chemokines in the Pathogenesis of Vascular Disease. *Circulation Research.* 95:858-866 (2004)

Kucic T, Copland I B, Cuerquis J, Coutu D L, Chalifour L E, Gagnon R F, et al. Mesenchymal stromal cells genetically engineered to overexpress IGF-I enhance cell-based gene therapy of renal failure-induced anemia. Am J Physiol Renal Physiol. 2008; 295(2):F488-96.

Lee I, Wang L, Wells A D, Ye Q, Han R, Dorf M E, Kuziel W A, Rollins B J, Chen L, Hancock W W. Blocking the monocyte chemoattractant protein-1/CCR2 chemokine pathway induces permanent survival of islet allografts through a programmed death-1 ligand-1-dependent mechanism. J. Immunol. 171(12):6929-35 (2003).

Loberg R D, Ying C, Craig M, Day L L, Sargent E, Neeley C, Wojno K, Snyder L A, Yan L, Pienta K J. Targeting CCL2 with systemic delivery of neutralizing antibodies induces prostate cancer tumor regression in vivo. *Cancer Res.* 67(19):9417-24 (2007).

Luini W, Sozzani S, Van Damme J, Mantovani A. Species-specificity of monocyte chemotactic protein-1 and -3. Cytokine. 1994; 6(1):28-31.

Luther S A, Cyster J G. Chemokines as regulators of T cell differentiation. *Nat. Immunol.* (2):102-7 (2001)

McQuibban G A, Gong J H, Wong J P, Wallace J L, Clark-Lewis I, Overall C M. Matrix metalloproteinase processing of monocyte chemoattractant proteins generates CC chemokine receptor antagonists with anti-inflammatory properties in vivo. Blood. 100(4):1160-7 (2002)

Mellado M, Rodríguez-Frade J M, Vila-Coro A J, Fernandez S, Martin de Ana A, Jones D R, Torán J L, Martinez-A C. Chemokine receptor homo- or heterodimerization activates distinct signaling pathways. EMBO J. 20(10):2497-507 (2001)

Onai N, Zhang Y, Yoneyama H, Kitamura T, Ishikawa S, Matsushima K. Impairment of lymphopoiesis and myelopoiesis in mice reconstituted with bone marrow-hematopoietic progenitor cells expressing SDF-1-intrakine. Blood. 96(6):2074-80 (2000)

Prevost G P, Lonchampt M O, Holbeck S, Attoub S, Zaharevitz D, Alley M, Wright J, Brezak M C, Coulomb H, Savola A, Huchet M, Chaumeron S, Nguyen Q D, Forgez P, Bruyneel E, Bracke M, Ferrandis E, Roubert P, Demarquay D, Gespach C, Kasprzyk P G. Anticancer activity of BIM-46174, a new inhibitor of the heterotrimeric Galpha/Gbetagamma protein complex. Cancer Res. 66(18):9227-34 (2006).

Rafei M, Wu J H, Annabi B, Lejeune L, Francois M, Galipeau J. A GMCSF and IL-15 fusokine leads to paradoxical immunosuppression in vivo via asymmetrical JAK/STAT signaling through the IL-15 receptor complex. Blood. 109 (5):2234-42. (2006).

Rafei M, Hsieh J, Fortier S, Li M, Yuan S, Birman E, Former K, Boivin M N, Doody K, Tremblay M, Annabi B, Galipeau J. Mesenchymal stromal cell-derived CCL2 suppresses plasma cell immunoglobulin production via STAT3 inactivation and PAX5 induction. Blood. 112(13): 4991-8 (2008)

Rafei M, Campeau P M, Wu J H, Birman E, Former K, Boivin M N, et al. Selective inhibition of CCR2 expressing lymphomyeloid cells in experimental autoimmune encephalomyelitis by a GM-CSF-MCP1 fusokine. J Immunol. 2009a; 182(5):2620-7.

Rafei M, Campeau P M, Aguilar-Mahecha A, Buchanan M, Williams P, Birman E, et al. Mesenchymal stromal cells ameliorate experimental autoimmune encephalomyelitis by inhibiting CD4 Th17 T cells in a CC chemokine ligand 2-dependent manner. J Immunol. 2009b; 182(10):5994-6002.

Sallusto, F., Mackay, C. R. & Lanzavecchia, A. The role of chemokine receptors in primary, effector, and memory immune responses. *Annu. Rev. Immunol.* 18, 593-620 (2000).

Shahrara S, Proudfoot A E, Park C C, Volin M V, Haines G K, Woods J M, Aikens C H, Handel T M, Pope R M. Inhibition of monocyte chemoattractant protein-1 ameliorates rat adjuvant-induced arthritis. J. Immunol. 180(5):3447-56 (2008)

Stagg J, Wu J H, Bougamin N, Galipeau J. Granulocyte-macrophage colony stimulating factor and interleukin-2 fusion cDNA for cancer gene therapy. *Cancer Research.* 64: 8795-99 (2004).

Terwey T H, Kim T D, Kochman A A, Hubbard V M, Lu S, Zakrzewski J L, Ramirez-Montagut T, Eng J M, Muriglan S J, Heller G, Murphy G F, Liu C, Budak-Alpdogan T, Alpdogan O, van den Brink M R. CCR2 is required for CD8-induced graft-versus-host disease. Blood. 106(9):3322-30 (2005).

Uguccioni M, Gionchetti P, Robbiani D F, Rizzello F, Peruzzo S, Campieri M, Baggiolini M. Increased expression of IP-10, IL-8, MCP-1, and MCP-3 in ulcerative colitis. Am J. Pathol. 155(2):331-6 (1999)

van Raam B J, Drewniak A, Groenewold V, van den Berg T K, Kuijpers T W. Granulocyte colony-stimulating factor delays neutrophil apoptosis by inhibition of calpains upstream of caspase-3. Blood. 112(5):2046-54 (2008).

Xie T X, Huang F J, Aldape K D, Kang S H, Liu M, Gershenwald J E, et al. Activation of stat3 in human melanoma promotes brain metastasis. Cancer Research. 2006; 66:3188-96.

The invention claimed is:

1. A conjugate protein comprising:

a. GM-CSF or a N-terminal fragment thereof lacking the last 11 carboxy terminal amino acids of GM-CSF linked to b. truncated CCL2, wherein the truncated CCL2 has the first 5 amino acids removed and acts as an antagonist as compared to full length CCL2, wherein the conjugate protein inhibits CCR2 homodimerization.

2. The conjugate protein according to claim 1 wherein the GM-CSF or N-terminal fragment thereof is linked to the truncated CCL2 by a peptide linker.

3. The conjugate protein according to claim 1 which has the sequence shown in SEQ ID NO:2 or 4.

4. A method of suppressing an immune response of CCR2-expressing cells comprising administering an effective amount of the conjugate protein according to claim 1 to an animal or cell in need thereof.

5. The method according to claim 4 for treating an autoimmune disease.

6. A pharmaceutical composition comprising an effective amount of the conjugate protein according to claim 1 in admixture with a suitable diluent or carrier.

* * * * *

SEQUENCE LISTING

```
<160> NUMBER OF SEQ ID NOS: 4

<210> SEQ ID NO 1
<211> LENGTH: 781
<212> TYPE: DNA
<213> ORGANISM: Artificial Sequence
<220> FEATURE:
<223> OTHER INFORMATION: Mouse Gmme1

<400> SEQUENCE: 1
atgtggctgc agaatttact tttcctgggc attgtggtct acagcctctc agcacccacc      60
cgctcaccca tcactgtcac ccggccttgg aagcatgtag aggccatcaa agaagccctg     120
aacctcctgg atgacatgcc tgtcacgttg aatgaagagg tagaagtcgt ctctaacgag     180
ttctccttca agaagctaac atgtgtgcag acccgcctga agatattcga gcagggtcta     240
cggggcaatt tcaccaaact caagggcgcc ttgaacatga cagccagcta ctaccagaca     300
tactgccccc caactccgga aacggactgt gaaacacaag ttaccaccta tgcggatttc     360
atagacagcc ttaaaacctt tctgactgat aacgcccac tcacctgctg ctactcattc     420
accagcaaga tgatcccaat gagtaggctg gagagctaca agaggatcac cagcagcagg     480
tgtcccaaag aagctgtagt ttttgtcacc aagctcaaga gagaggtctg tgctgacccc     540
aagaaggaat gggtccagac atacattaaa aacctggatc ggaaccaaat gagatcagaa     600
cctacaactt tatttaaaac tgcatctgcc ctaaggtctt cagcaccttt gaatgtgaag     660
ttgacccgta atctgaagc taatgcatcc actaccttt ccacaaccac ctcaagcact     720
tctgtaggag tgaccagtgt gacagtgaac tagtgtgact cggactgtga tgccttgcta     780
g                                                                    781

<210> SEQ ID NO 2
<211> LENGTH: 251
<212> TYPE: PRT
<213> ORGANISM: Artificial Sequence
<220> FEATURE:
<223> OTHER INFORMATION: Mouse Gmme1

<400> SEQUENCE: 2

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60
```

-continued

```
Lys Leu Thr Cys Val Gln Thr Arg Leu Lys Ile Phe Glu Gln Gly Leu
 65                  70                  75                  80

Arg Gly Asn Phe Thr Lys Leu Lys Gly Ala Leu Asn Met Thr Ala Ser
                 85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Asp Asn Ala Pro Leu Thr Cys Cys Tyr Ser Phe Thr Ser Lys
    130                 135                 140

Met Ile Pro Met Ser Arg Leu Glu Ser Tyr Lys Arg Ile Thr Ser Ser
145                 150                 155                 160

Arg Cys Pro Lys Glu Ala Val Val Phe Val Thr Lys Leu Lys Arg Glu
                165                 170                 175

Val Cys Ala Asp Pro Lys Lys Glu Trp Val Gln Thr Tyr Ile Lys Asn
            180                 185                 190

Leu Asp Arg Asn Gln Met Arg Ser Glu Pro Thr Thr Leu Phe Lys Thr
        195                 200                 205

Ala Ser Ala Leu Arg Ser Ser Ala Pro Leu Asn Val Lys Leu Thr Arg
    210                 215                 220

Lys Ser Glu Ala Asn Ala Ser Thr Thr Phe Ser Thr Thr Thr Ser Ser
225                 230                 235                 240

Thr Ser Val Gly Val Thr Ser Val Thr Val Asn
                245                 250
```

```
<210> SEQ ID NO 3
<211> LENGTH: 754
<212> TYPE: DNA
<213> ORGANISM: Artificial Sequence
<220> FEATURE:
<223> OTHER INFORMATION: Human Gmme1

<400> SEQUENCE: 3
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga tgaaacagtg agaagtcatc     180
tcagaaatgt ttgacctcca ggagccgacc tgcctacaga cccgcctgga gctgtacaag     240
cagggcctgc ggggcagcct caccaagctc aagggccct tgaccatgat ggccagccac     300
tacaagcagc actgccctcc aaccccggaa acttcctgtg caaccagat atcacctt      360 gaaagtttca aagagaacct gaaggacttt ctgcttgtca tccctttga ctgctgggag      420 ccagtccagc tcgaggccct tctgtgcctg ctgctcatag cagccacctt cattccccaa     480
gggctcgctc agccagatgc aatcaatgcc ccagtcacct gctgctataa cttcaccaat     540
aggaagatct cagtgcagag gctcgcgagc tatagaagaa tcaccagcag caagtgtccc     600
aaagaagctg tgatcttcaa gaccattgtg gccaaggaga tctgtgctga ccccaagcag     660
aagtgggttc aggattccat ggaccacctg acaagcaaa cccaaactcc gaagacttga     720
acactcactc cacaacccaa gaatctgcag ctag                                 754
```

```
<210> SEQ ID NO 4
<211> LENGTH: 214
<212> TYPE: PRT
<213> ORGANISM: Artificial Sequence
<220> FEATURE:
<223> OTHER INFORMATION: Human Gmme1
```

-continued

```
<400> SEQUENCE: 4

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Pro Phe Asp Cys Trp Glu Pro Val Gln Leu Glu Asn
    130                 135                 140

Ala Pro Val Thr Cys Cys Tyr Asn Phe Thr Asn Arg Lys Ile Ser Val
145                 150                 155                 160

Gln Arg Leu Ala Ser Tyr Arg Arg Ile Thr Ser Ser Lys Cys Pro Lys
                165                 170                 175

Glu Ala Val Ile Phe Lys Thr Ile Val Ala Lys Glu Ile Cys Ala Asp
            180                 185                 190

Pro Lys Gln Lys Trp Val Gln Asp Ser Met Asp His Leu Asp Lys Gln
        195                 200                 205

Thr Gln Thr Pro Lys Thr
    210
```